US010480031B2

(12) United States Patent
Bharti et al.

(10) Patent No.: US 10,480,031 B2
(45) Date of Patent: Nov. 19, 2019

(54) METHOD FOR GENERATING RETINAL PIGMENT EPITHELIUM (RPE) CELLS FROM INDUCED PLURIPOTENT STEM CELLS (IPSCS)

(71) Applicant: THE UNITED STATES OF AMERICA, as represented by the Secretary, Department of Health and Human Services, Bethesda, MD (US)

(72) Inventors: Kapil Bharti, Potomac, MD (US); Janine Davis, Baltimore, MD (US)

(73) Assignee: The United States of America, as represented by the Secretary, Department of Health and Human Services, Bethesda, MD (US)

(*) Notice: Subject to any disclaimer, the term of this patent is extended or adjusted under 35 U.S.C. 154(b) by 0 days.

(21) Appl. No.: 15/969,686

(22) Filed: May 2, 2018

(65) Prior Publication Data
US 2018/0291448 A1 Oct. 11, 2018

Related U.S. Application Data

(63) Continuation of application No. 14/764,959, filed as application No. PCT/US2014/014160 on Jan. 31, 2014, now abandoned.

(60) Provisional application No. 61/759,988, filed on Feb. 1, 2013.

(51) Int. Cl.
C12N 5/079 (2010.01)
C12Q 1/6881 (2018.01)
G01N 33/50 (2006.01)
G01N 33/569 (2006.01)

(52) U.S. Cl.
CPC ......... *C12Q 1/6881* (2013.01); *C12N 5/0621* (2013.01); *G01N 33/5058* (2013.01); *G01N 33/56966* (2013.01); *C12N 2501/115* (2013.01); *C12N 2501/16* (2013.01); *C12N 2501/41* (2013.01); *C12N 2501/415* (2013.01); *C12N 2501/999* (2013.01); *C12N 2506/45* (2013.01); *C12Q 2600/158* (2013.01); *C12Q 2600/16* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 2009/0274667 | A1 | 11/2009 | Temple et al. |
| 2010/0105137 | A1 | 4/2010 | Takahashi et al. |
| 2011/0002897 | A1 | 1/2011 | Snyder |
| 2011/0027333 | A1 | 2/2011 | Idelson et al. |
| 2011/0274662 | A1 | 11/2011 | Malcuit et al. |
| 2013/0195806 | A1 | 8/2013 | Gay et al. |
| 2013/0224156 | A1 | 8/2013 | Takahashi et al. |
| 2015/0175964 | A1 | 6/2015 | Clegg et al. |

FOREIGN PATENT DOCUMENTS

| | | |
|---|---|---|
| EP | 2 383 333 A1 | 11/2011 |
| WO | WO 2008/129554 | 10/2008 |
| WO | WO 2009/051671 | 4/2009 |
| WO | WO 2009/134681 | 11/2009 |
| WO | WO 2011/028524 | 3/2011 |
| WO | WO 2011/043592 | 4/2011 |
| WO | WO 2011/063005 | 5/2011 |
| WO | WO 2013/184809 | 12/2013 |

OTHER PUBLICATIONS

Huang et al, (PNAS, 106(40: 16978-16983, 2009) (Year: 2009).*
Jeon et al, (Stem Cell Research, p. 1-14, 2017) (Year: 2017).*
Nazari et al (Oncotarget, 7(16): 1-39, 2016) (Year: 2016).*
Adijanto et al., "$CO_2$-induced ion fluid transport in human retinal pigment epithelium," *Journal of General Physiology* 133(6): 603 (2008).
Bharti et al., "The new paradigm: retinal pigment epithelium cells generated from embryonic or induced pluripotent stem cells," *Pigment Cell Melanoma Research* 24: 21-34 (Sep. 15, 2010).
Borooah et al., "Using human induced pluripotent stem cells to treat retinal disease," *Progress in Retinal Eye Research* 37:163-181 (2013).
Hambright et al., "Long-term survival and differentiation of retinal neurons derived from human embryonic stem cell lines in un-immunosuppressed mouse retina," *Molecular Vision* 18: 920-936 (Apr. 12, 2012).
Idelson et al., Directed differentiation of human embryonic stem cells into functions retinal pigment epithelium cells, *Cell Stem Cell* 5: 396-408 (Oct. 2, 2009).
International Search Report from parent PCT Application No. PCT/US2014/014160, 7 pages (dated Oct. 28, 2014).
Kokkinaki et al., "Human iPS-derived retinal pigment epithelium (RPR) cells exhibit ion transport, membrane potential, polarized VEGF secretion and gene expression pattern similar to native RPE," *Stem Cells* 29(5): 825-835 (May 1, 2011).
Maminishkis et al., "Confluent monolayers of cultured human fetal retinal pigment epithelium exhibit morphology and physiology of native tissue," Investigative Opththalm & Visual Science 47(8): 3612-3624 (Aug. 2006).

(Continued)

Primary Examiner — Anoop K Singh
Assistant Examiner — Magdalene K Sgagias
(74) Attorney, Agent, or Firm — Klarquist Sparkman, LLP

(57) ABSTRACT

High efficiency methods for producing retinal pigment epithelial cells from induced pluripotent stem cells (iPSCs) are disclosed herein. The iPSCs are produced from somatic cells, including retinal pigment epithelial (RPE) cells, such as fetal RPE stem cells. In some embodiments, the iPSC include a tyrosinase promoter operably linked to a marker. Methods are disclosed for using the RPE cells, such as for treatment. Methods for screening for agents that affect RPE differentiation are also disclosed.

27 Claims, 43 Drawing Sheets
Specification includes a Sequence Listing.

(56) References Cited

OTHER PUBLICATIONS

Miyagishma et al., "In pursuit of authenticity: Induced pluripotent stem cell-derived retinal pigment epithelium for clinical applications," *Stem Cells Translation Medicine* 5: 1562-1574 (2016).
Peixoto et al., "Quantification of multiple gene expression in individual cells," *Genome Research* 14(10a): 1938-1947 (2004).
Rowland et al., "Pluripotent human stem cells for the treatment of retinal disease," *Journal of Cell Physiology* 227:457-466 (2012).
Singh et al., "iPS cell modeling of Best disease: insights into the pathophysiology of an inherited macular designation," *Human Molecular Genetics* 22(3): 593-607 (published online Nov. 8, 2012).
Wang, "Wnt/Planar cell polarity: A new paradigm for cancer therapy," *Molecular Cancer Therapy* 8(8): 2103-2109 (published online Aug. 11, 2009).
Wollmann et al., "Voltage-dependent ion channels in the mouse RPE: comparison with Norrie disease mice," *Vision Research* 46: 688-698 (2006).
Written Opinion from parent PCT Application No. PCT/US2014/014160, 9 pages (dated Oct. 28, 2014).

\* cited by examiner

FIG. 4

| Gene | Fold change |
|---|---|
| Transcription factors | |
| MITF | 36.8 |
| PAX6 | 16.0 |
| TFEC | 39.4 |
| OTX2 | 21.1 |
| Visual cycle genes | |
| RLBP1 | 34.3 |
| RPE65 | 2.6 |

| Gene | Fold change |
|---|---|
| Pigmentation genes | |
| TYRP1 | 111.4 |
| DCT | 128.0 |
| TYR | 55.7 |
| PMEL | 36.8 |
| OCA2 | 9.2 |

| Gene | Fold change |
|---|---|
| Structural proteins | |
| CLDN19 | 29.9 |
| CLDN16 | 3.2 |
| CSPG5 | 3.2 |
| Channel genes | |
| TRPM1 | 59.7 |
| TRPM3 | 21.1 |
| BEST1 | 9.2 |
| CFTR | 3.5 |

FIG. 5A GFP negative cells

FIG. 5B GFP positive cells

➢ When FACS purified GFP positive and negative cells were re-seeded on to culture plates, only GFP positive cells grew to form homogenous pigmented cultures. This proves that GFP expression truly represents RPE fate in this iPS cell line.

FIG. 8

| Changes in Medium 1 | Fold change in Pax6 expression for cells that are in medium 1 for 1 week as compared to day 0 cultures/embryoid bodies |
|---|---|
| FGF2 (5ng/ul) | 141x |
| FGF2 (5ng/ul) + Noggin (100ng/ul) | 160x |
| FGF2 (0.5ng/ul) | 163x |
| FGF2 (0.5ng/ul) + Noggin (100ng/ul) | 155x |
| NO FGF2 | 127x |
| NO FGF2 + Noggin (100ng/ul) | 123x |
| NO FGF2 + PD 0325901 (10mM) | 192x |
| NO FGF2 + PD 0325901 (10mM) + Noggin (100ng/ul) | 168x |
| NO FGF2 + PD 0325901 (10mM) + Noggin (50ng/ul) | 186x |
| NO FGF2 + PD 0325901 (10mM) + Noggin (50ng/ul) +DKK1 | 242x |

FIG. 9

| Changes in Medium 1 | Fold change in Pax6 expression for cells that are in medium 1 for 2 weeks as compared to day 0 cultures/embryoid bodies |
|---|---|
| FGF2 (5ng/ul) | - 180x |
| FGF2 (5ng/ul) + Noggin (100ng/ul) | - 281x |
| FGF2 (0.5ng/ul) | - 221x |
| FGF2 (0.5ng/ul) + Noggin (100ng/ul) | - 324x |
| NO FGF2 | - 289x |
| NO FGF2 + Noggin (100ng/ul) | - 254x |
| NO FGF2 + PD 0325901 (10mM) | - 434x |
| NO FGF2 + PD 0325901 (10mM) + Noggin (100ng/ul) | - 574x |
| NO FGF2 + PD 0325901 (10mM) + Noggin (50ng/ul) | - 527x |
| NO FGF2 + PD 0325901 (10mM) + Noggin (50ng/ul) +DKK1 | - 609x |

FIG. 10

Changes in Medium 1 — Fold change in Pax6 expression for cells that are in medium 1 for 3 weeks as compared to day 0 cultures/embryoid bodies FGF2 (5ng/ul) — 180x
FGF2 (5ng/ul) + Noggin (100ng/ul) — 289x
FGF2 (0.5ng/ul) — 435x
FGF2 (0.5ng/ul) + Noggin (100ng/ul) — 372x
NO FGF2 — 386x
NO FGF2 + Noggin (100ng/ul) — 717x
NO FGF2 + PD 0325901 (10mM) — 546x
NO FGF2 + PD 0325901 (10mM) + Noggin (100ng/ul) — 922x
NO FGF2 + PD 0325901 (10mM) + Noggin (50ng/ul) — 929x
NO FGF2 + PD 0325901 (10mM) + Noggin (50ng/ul) +DKK1 — 942x

FIG. 11

Changes in Medium 1 — Fold change in MITF expression for cells that are in medium 1 for 1 week as compared to day 0 cultures/embryoid bodies

| | |
|---|---|
| FGF2 (5ng/ul) | - 0.2x |
| FGF2 (5ng/ul) + Noggin (100ng/ul) | - 0.07x |
| FGF2 (0.5ng/ul) | - 3.8x |
| FGF2 (0.5ng/ul) + Noggin (100ng/ul) | - 0.34x |
| NO FGF2 | - 0.6x |
| NO FGF2 + Noggin (100ng/ul) | - 0.5x |
| NO FGF2 + PD 0325901 (10mM) | - 8.2x |
| NO FGF2 + PD 0325901 (10mM) + Noggin (100ng/ul) | - 4.1x |
| NO FGF2 + PD 0325901 (10mM) + Noggin (50ng/ul) | - 4.5x |
| NO FGF2 + PD 0325901 (10mM) + Noggin (50ng/ul) +DKK1 | - 4.7x |

MITF expression should start to increase around week 3 of differentiation, when the cells are getting to the optic vesicle stage

FIG. 12

Changes in Medium 1 — Fold change in MITF expression for cells that are in medium 1 for 2 weeks as compared to day 0 cultures/embryoid bodies

| | |
|---|---|
| FGF2 (5ng/ul) | − 16.3x |
| FGF2 (5ng/ul) + Noggin (100ng/ul) | − 2.5x |
| FGF2 (0.5ng/ul) | − 3.1x |
| FGF2 (0.5ng/ul) + Noggin (100ng/ul) | − 1.2x |
| NO FGF2 | − 5.3x |
| NO FGF2 + Noggin (100ng/ul) | − 0.4x |
| NO FGF2 + PD 0325901 (10mM) | − 3.6x |
| NO FGF2 + PD 0325901 (10mM) + Noggin (100ng/ul) | − 4.2x |
| NO FGF2 + PD 0325901 (10mM) + Noggin (50ng/ul) | − 1.2x |
| NO FGF2 + PD 0325901 (10mM) + Noggin (50ng/ul) +DKK1 | − 5.5x |

FIG. 13

| Changes in Medium 1 | — | Fold change in MITF expression for cells that are in medium 1 for 3 weeks as compared to day 0 cultures/embryoid bodies |

FGF2 (5ng/ul) — 3.6x
FGF2 (5ng/ul) + Noggin (100ng/ul) — 1.6x
FGF2 (0.5ng/ul) — 5.3x
FGF2 (0.5ng/ul) + Noggin (100ng/ul) — 2.8x
NO FGF2 — 11.1x
NO FGF2 + Noggin (100ng/ul) — 3.0x
NO FGF2 + PD 0325901 (10mM) — 2.8x
NO FGF2 + PD 0325901 (10mM) + Noggin (100ng/ul) — 6.6x
NO FGF2 + PD 0325901 (10mM) + Noggin (50ng/ul) — 2.5x
NO FGF2 + PD 0325901 (10mM) + Noggin (50ng/ul) +DKK1 — 48.4x MITF expression should start to increase around week 3 of differentiation, when the cells are getting to the optic vesicle stage

FIG. 14

| Changes in Medium 1 | % GFP at the end of 6 weeks of culture |
|---|---|
| FGF2 (5ng/ul) | 9% |
| FGF2 (5ng/ul) + Noggin (100ng/ul) | 16% |
| FGF2 (0.5ng/ul) | 24% |
| FGF2 (0.5ng/ul) + Noggin (100ng/ul) | 14% |
| NO FGF2 | 11% |
| NO FGF2 + Noggin (100ng/ul) | 16% |
| NO FGF2 + PD 0325901 (10mM) | 29% |
| NO FGF2 + PD 0325901 (10mM) + Noggin (100ng/ul) | 18% |
| NO FGF2 + PD 0325901 (10mM) + Noggin (50ng/ul) | 35% |
| NO FGF2 + PD 0325901 (10mM) + Noggin (50ng/ul) +DKK1 | 50% |

FIG. 20 iPS cell-derived RPE, NAW treated (92% GFP positive)

FIG. 21

TFEC – 0.1X
PAX6 – 0.2x
SOX2 – 0.2x
KLF4 – 0.2X

SNAIL1 – 0.3x
SNAIL2 – 0.1x

Cadherin 1 – 2X
Cadherin 3 – 1.7x

TRPM1 – 1.8x
TRPM3 – 2.2X

MYRIP – 2.1x
TYR – 4.7x
TYRP1 – 1.6x

FIG. 23
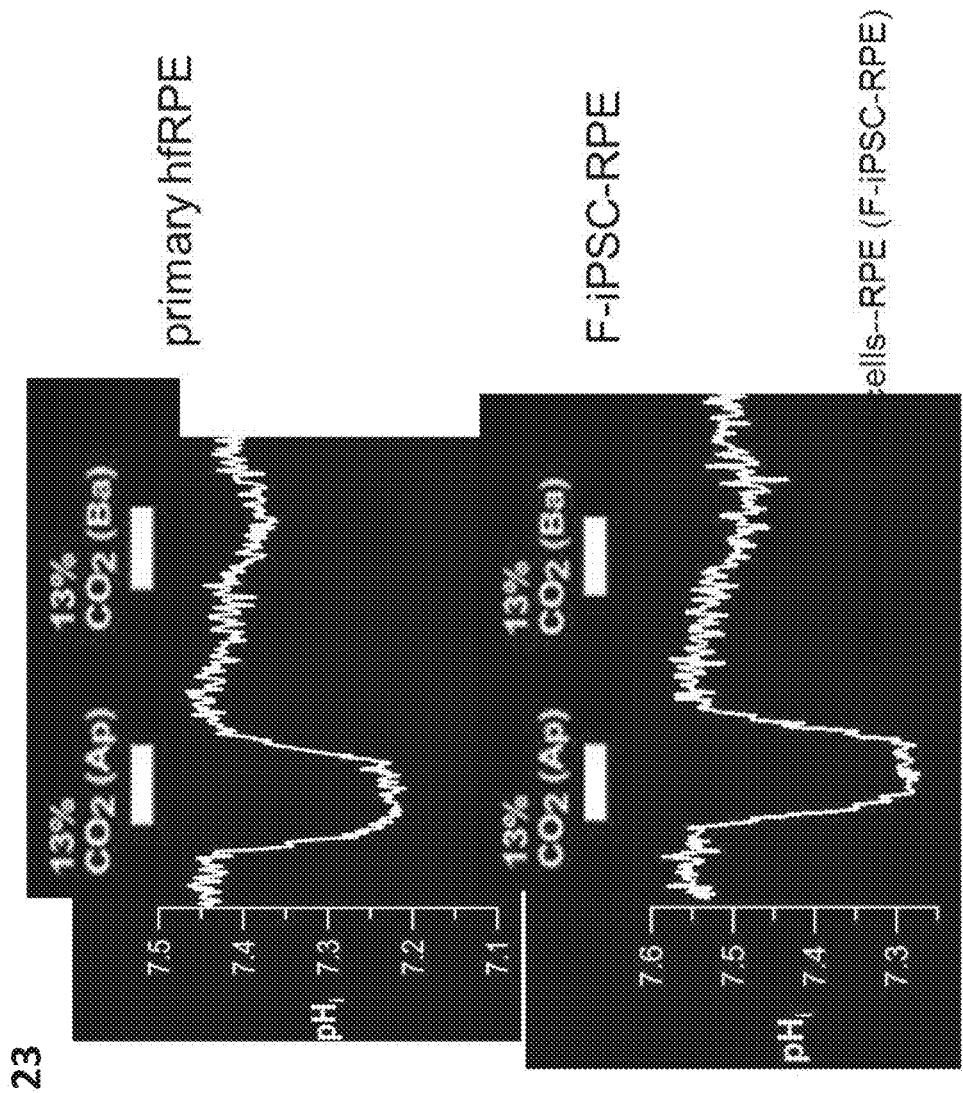
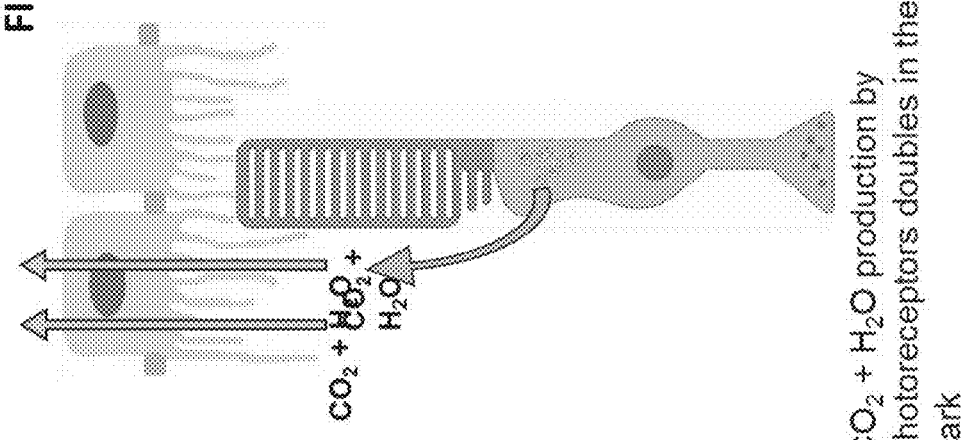

Immunostaining of iPSC-RPE

Transmission electron microscopy of iPSC-RPE

FIG. 27A Day 1

Probes used for the multiplex assay

| Gene name | Accession # | mRNA length (bases) | Probed region (bases) |
|---|---|---|---|
| SOX2 | NM_003106 | 2520 | 920-1452 |
| PAX6 | NM_001604 | 6913 | 131-546* |
| RPE65 | NM_000329 | 2608 | 1120-1576 |
| RDH5 | NM_002905 | 1354 | 262-841* |
| CSPG5 | NM_006574 | 2175 | 436-896* |
| TRPM1 | NM_002420 | 5724 | 1872-2291 |
| BEST1 | NM_004183 | 2690 | 1746-2174* |
| TYROSINASE | NM_000372 | 2082 | 790-1414 |
| HPRT1 | NM_000194 | 1435 | 102-646 |
| B2M | NM_004048 | 987 | 585-828 |

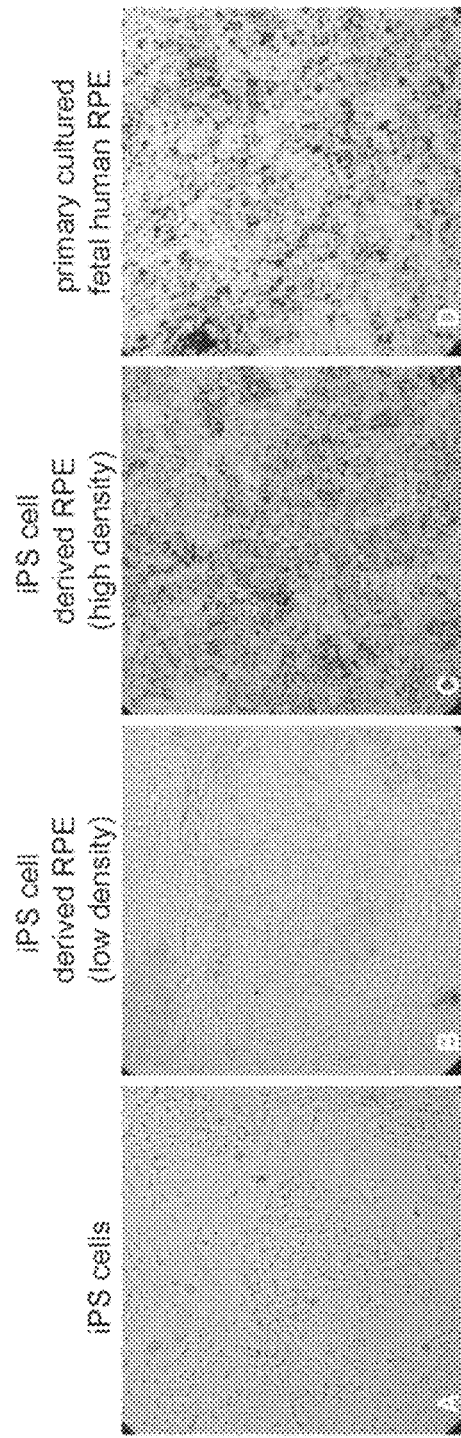

fold change in gene expression in iPS cell derived RPE as compared to primary fetal RPE cultures

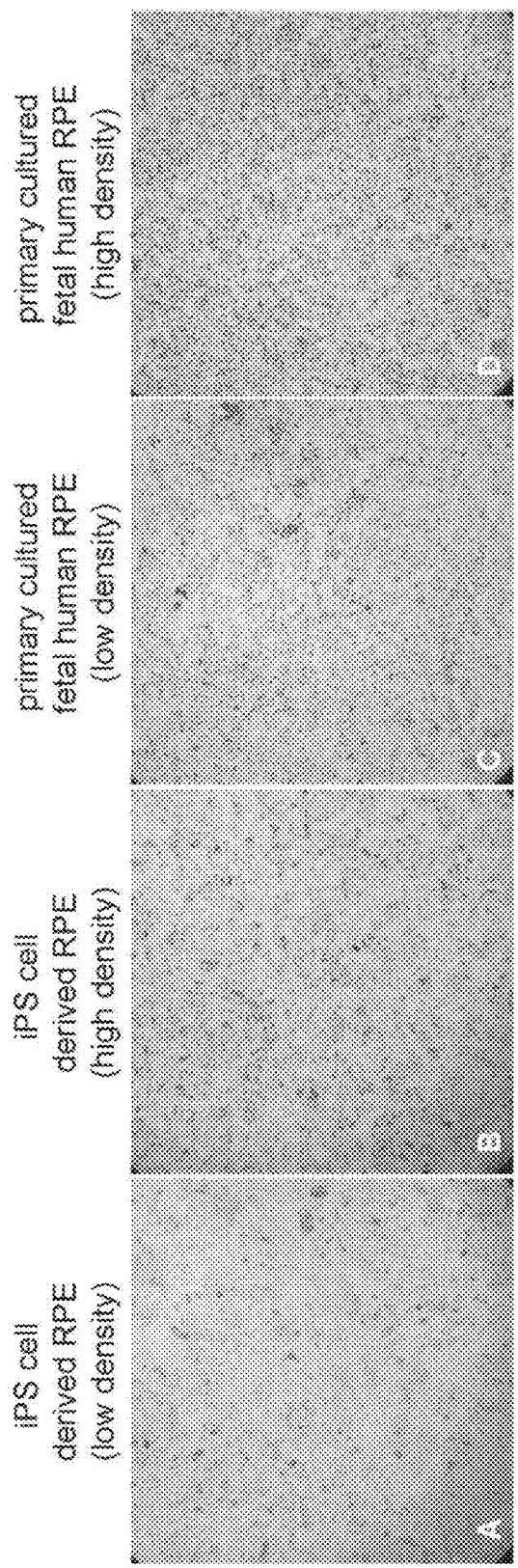

fold change in gene expression in iPS cell derived RPE as compared to primary fetal RPE cultures (half the number of beads)

METHOD FOR GENERATING RETINAL PIGMENT EPITHELIUM (RPE) CELLS FROM INDUCED PLURIPOTENT STEM CELLS (IPSCS)

CROSS REFERENCE TO RELATED APPLICATIONS

This is a continuation of U.S. patent application Ser. No. 14/764,959, filed on Jul. 30, 2015, which is the U.S. National Stage of International Application No. PCT/US2014/014160, filed Jan. 31, 2014, which was published in English under PCT Article 21(2), which claims the benefit of U.S. Patent Application No. 61/759,988, filed Feb. 1, 2013. The prior applications are incorporated herein by reference in their entirety.

FIELD OF THE DISCLOSURE

This disclosure is related to the field of retinal pigment epithelium (RPE) cells, and specifically to methods for producing RPE cells from stem cells.

BACKGROUND

The retina is a layer of specialized light sensitive neural tissue located at the inner surface of the eye of vertebrates. Light reaching the retina after passing the cornea, the lens and the vitreous humor is transformed into chemical and electrical events that trigger nerve impulses. The cells that are responsible for transduction, the process for converting light into these biological processes are specialized neurons called photoreceptor cells.

The retinal pigment epithelium (RPE) is a polarized monolayer of densely packed hexagonal cells in the mammalian eye that separates the neural retina from the choroid. The cells in the RPE contain pigment granules and perform a crucial role in retinal physiology by forming a blood-retinal barrier and closely interacting with photoreceptors to maintain visual function by absorbing the light energy focused by the lens on the retina. These cells also transport ions, water, and metabolic end products from the subretinal space to the blood and take up nutrients such as glucose, retinol, and fatty acids from the blood and deliver these nutrients to photoreceptors.

RPE cells are also part of the visual cycle of retinal: Since photoreceptors are unable to reisomerize all-trans-retinal, which is formed after photon absorption, back into 11-cis-retinal, retinal is transported to the RPE where it is reisomerized to 11-cis-retinal and transported back to the photoreceptors.

Many ophthalmic diseases, such as (age-related) macular degeneration, macular dystrophies such as Stargardt's and Stargardt's-like disease, Best disease (vitelliform macular dystrophy), and adult vitelliform dystrophy or subtypes of retinitis pigmentosa, are associated with a degeneration or deterioration of the retina itself or of the RPE. It has been demonstrated in animal models that photoreceptor rescue and preservation of visual function could be achieved by subretinal transplantation of RPE cells (Coffey et al. Nat. Neurosci. 2002:5, 53-56; Lin et al. Curr. Eye Res. 1996:15, 1069-1077; Little et al. Invest. Ophthalmol. Vis. Sci. 1996: 37, 204-211; Sauve et al. Neuroscience 2002:114, 389-401). There is a need to find ways to produce RPE cells, such as from human stem cells, that can be used for the treatment of retinal degenerative diseases and injuries.

SUMMARY OF THE DISCLOSURE

High efficiency methods for producing retinal pigment epithelial cells from induced pluripotent stem cells (iPSCs) are disclosed herein. The iPSCs are produced from somatic cells, including retinal pigment epithelial cells, such as fetal retinal pigment epithelial stem cells.

In some embodiments, the method for producing human retinal pigment epithelial cells includes producing embryoid bodies from human induced pluripotent stem cells. The embryoid bodies are cultured in a first medium comprising two Wnt pathway inhibitors and a Nodal pathway inhibitor. The embryoid bodies are plated on a tissue culture substrate in a second medium. In certain embodiments, the second medium (a) does not include basic fibroblast growth factor (bFGF) (b) includes a basic fibroblast growth factor (bFGF) inhibitor, the two Wnt pathway inhibitors, and the Nodal pathway inhibitor; (c) includes about 20 to about 90 ng of Noggin; and (d) includes about 1 to about 3% knock out serum replacement to form differentiating retinal pigment epithelial cells. The differentiating retinal pigment epithelial cells are then cultured in a third medium comprising ACTIVAN A and WNT3a. The cells are then cultured in retinal pigment epithelial cell (RPE) medium that includes about 5% fetal serum, a canonical WNT inhibitor, a non-canonical WNT inducer, and inhibitors of the Sonic and FGF pathway to produce human retinal pigment epithelial cells.

In additional embodiments, methods are disclosed for detecting RPE cells, or confirming that a cell is a RPE cell. In yet other embodiments, methods are disclosed for determining if a test agent affects the production of RPE cells from an iPSC. In further embodiments, methods are provided to identify a test agent that increases gene expression and can be used as a therapeutic agent. In yet other embodiments, methods are provided to identify a test agent that increases RPE survival in response to a proteotoxic insult or stress.

The foregoing and other features and advantages of the invention will become more apparent from the following detailed description of a several embodiments, which proceeds with reference to the accompanying figures.

BRIEF DESCRIPTION OF THE FIGURES

FIG. 4 is a table of results from FACS purified GFP positive cells, showing the cells are enriched for expression of early RPE genes. GFP positive cells and negative cells from the same dish were purified by FACS and the expression of RPE-specific markers was compared in the two populations. GFP positive cells are several fold enriched in the expression of RPE-specific genes.

FIGS. 8-10 are tables showing the fold change in PAX6 expression with different culture conditions.

FIGS. 11-13 are tables showing the fold change in MITF expression using different culture conditions. MITF expression should start to increase around week 3 of differentiation, when the cells are getting to the optic vesicle stage.

FIG. 14 is a table showing the percent GFP positive cells (representing cells of the RPE fate) using different culture conditions.

FIG. 17 is a set of digital images and plots showing WNT3a significantly increases the number of GFP positive cells in differentiating iPSC cultures. The upper panel shows GFP positive and RFP positive cells in a dish. The lower panel shows FACS analysis for the GFP signal. For these experiments, MEDIUM 2 (FGF2–0.5 ng/ml)+MEDIUM 3 (NA or NAW), wherein NA=Nicotinamide & ACTIVIN, NAW=Nicotinamide, ACTIVIN & WNT3a.

Medium 2—NO FGF2+PD 0325901 (10 mM)+Noggin (50 ng/ul)+DKK1

Medium 3—Activin A (150 ng/ml)+WNT3a (100 ng/ml)

Medium 4—See the examples section below.

Figure 19:

FIG. 19 is a digital image showing that WNT3a generates RPE cells with homogenous pigmentation. Cells from these dishes were trypsinized and replated into T-25 flasks. For these experiments, MEDIUM 2 (FGF2–0.5 ng/ml)+MEDIUM 3 (NA or NAW), wherein NA=Nicotinamide & ACTIVIN, NAW=Nicotinamide, ACTIVIN & WNT3a.]

Figure 20:
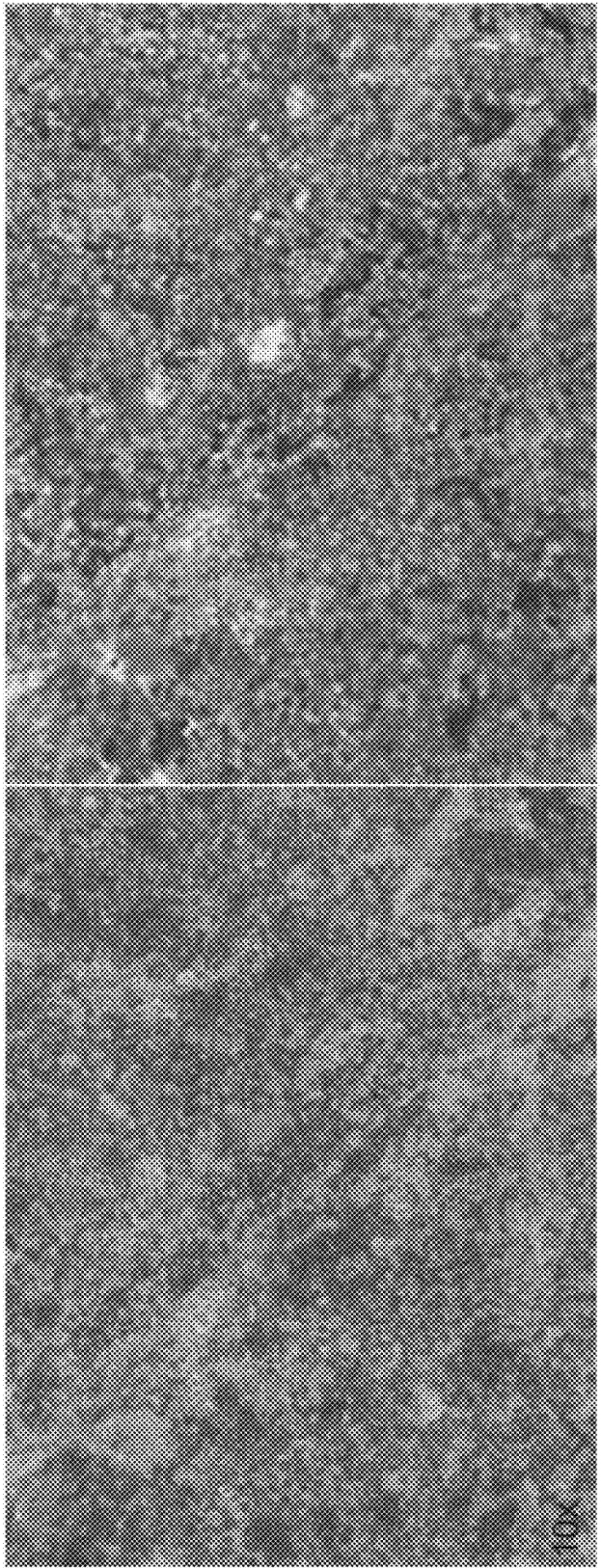

FIG. 20 is a digital image of iPSC-derived RPE, NAW treated (92% GFP positive). At higher resolution these cells look quite homogenous in terms of RPE morphology, GFP expression, and pigmentation.

FIG. 21 is a table showing that inhibition of endogenous pathways (WNT, FGF, SONIC) in iPSC-RPE produces fully-mature RPE cultures Medium #4–5% RPE medium+ inhibitors of WNT, FGF, SONIC. WNT inhibitors include DKK1 and non-canonical WNT (WNT5a), FGF inhibitor SU5042, and SONIC inhibitor Cyclopamine.

Figure 22:
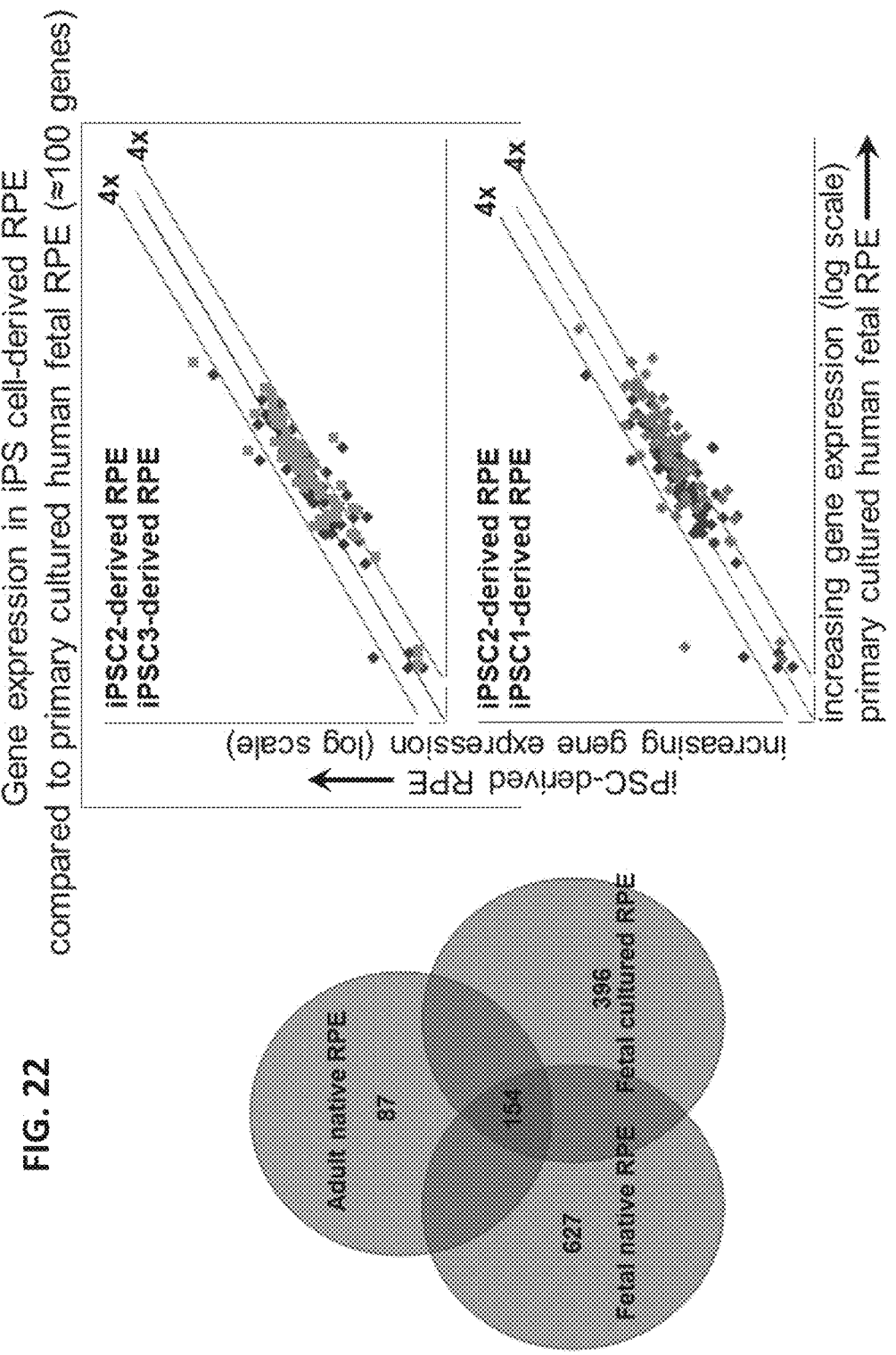

FIG. 22 is a set of graphs and a Venn diagram illustrating RPE gene expression is iPSC-RPE. The expression of a total 384 genes was evaluated (Strunnikova et al., *Hum Mol Genet.* 2010 Jun. 15; 19(12):2468-86). The top 350 genes were selected; 34 genes were controls. A custom 384-well plate was developed to analyze the expression of all these genes by real-time PCR. This plate/array can be used to authenticate iPSC-RPE cells. They include RPE gene signature, fetal-RPE enriched genes, and adult-RPE enriched genes. A comparison of ~100 fetal-RPE enriched genes among three iPSC lines derived RPE is shown.

FIG. 23 is a schematic diagram and graphs evidencing the physiology of iPSC derived RPE. Selective $CO_2$ permeability of the apical surface of RPE cells is shown (Adijanto et al., J Gen Physiol. 2009 June; 133(6):603-22). Photoreceptors secrete $CO_2$ towards the apical surface of RPE cells. Therefore, this surface has been evolutionarily selected to trap $CO_2$. This function can be measured in vitro by changing $CO_2$ concentrations in the apical or the basal baths of RPE cells growing in transwells. If RPE cells trap $CO_2$, they respond by a reduction in pH, which can be measured by a ratio-metric dye. iPSC-derived RPE function similar to the native RPE for differential $CO_2$ uptake only on the apical side.

Figure 24:
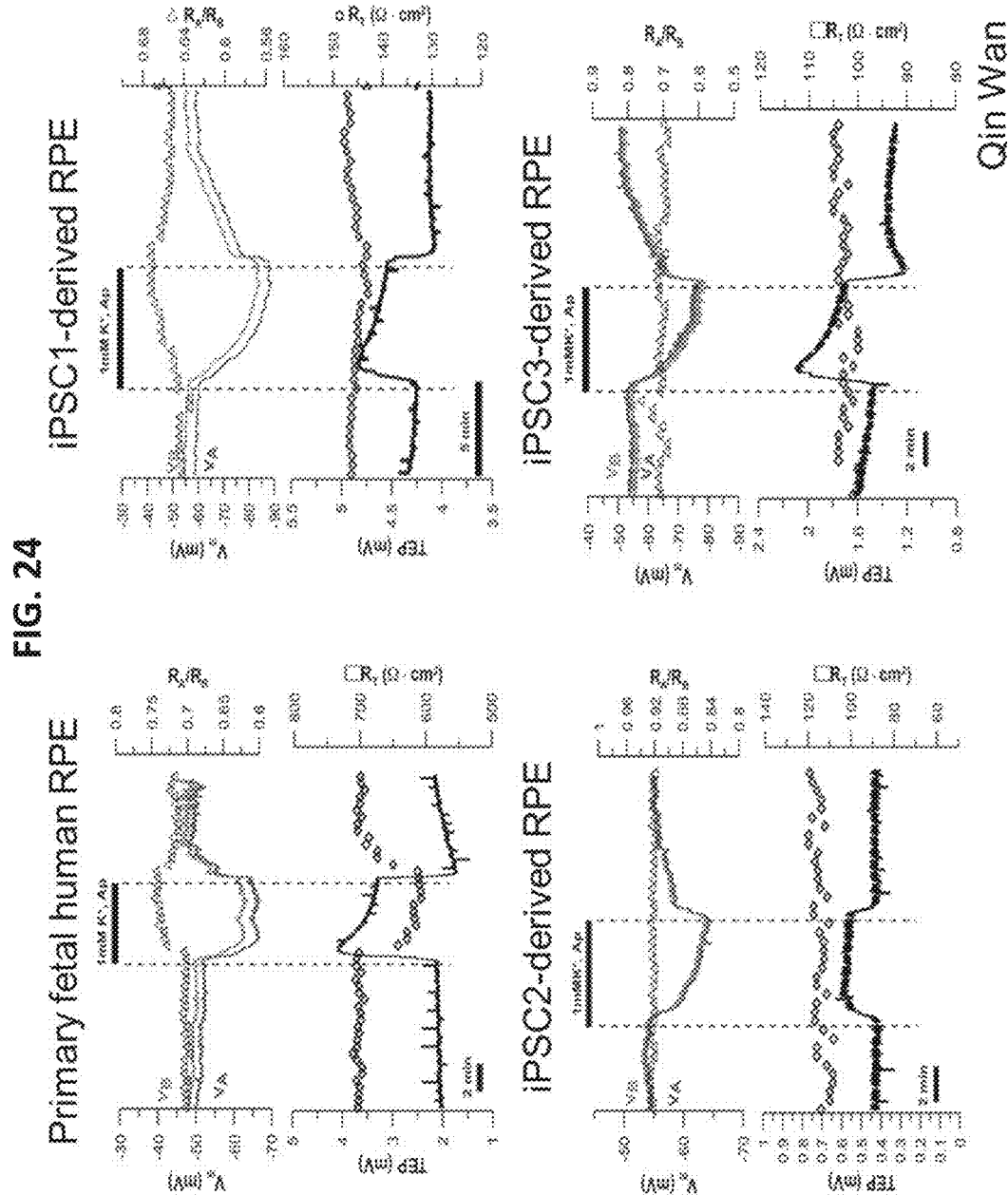

FIG. 24 is a set of graphs showing changes in electrophysiological properties of iPSC-derived RPE cells by changes in extracellular ionic concentrations. When light hits the photoreceptors, they depolarize by shutting down their potassium (K) channels. This reduces the concentration of K-ions in between photoreceptors and RPE (subretinal space) from 5 mM to 1 mM. RPE cells respond to this changing concentration by hyperpolarizing and opening their K channels to increase the subretinal K concentration back to 5 mM.

FIGS. 25A-25D are schematic diagrams, digital images and graphs. (A) Schematic of the step-wise protocol for differentiation of iPSCs into RPE, authentication of RPE cells, and their use for a multiplex screening. The different type of media used throughout the process and the timeline of the process are shown. (B) Characterization of the iPSC line used for generating RPE for screening. Fully confluent iPSCs were stained with antibodies against indicated pluripotency markers. Cells express high levels of all these markers. Bright field images show iPSC colony morphology. (C) qRT-PCR analysis of pluripotency markers NANOG, OCT4, SOX2, c-MYC, and KLF4 in iPSC line used for RPE differentiation. Fibroblasts and embryonic stem cell RNA are used for comparison. (D) Immunostaining of iPSCs spontaneously differentiated in vitro after bFGF withdrawal. iPSCs are able to generate cells from the three germ layers (AFP=endoderm; TUJ1=ectoderm; SMA=mesoderm). The bar represents 50 microns. KSR—knockout serum replacement containing medium, NIC—nicotinamide.

FIGS. 26A-26D show authentication of iPSC-derived RPE. RPE cells were grown on semi-permeable transwells until fully confluent and characterized by immunostaining for RPE markers (A), electron microscopy (B), intracellular calcium responses (C), electrophysiological responses (D). (A) RPE cells were stained with antibodies against EZRIN, DCT, SLC16A1, CLCN2 (grey) and ZO1 (bright lines). (B) Electron micrograph of a section of RPE growing on a semi-permeable transwell. Cells show several features typical of RPE including extensive apical process, apically localized pigmented melanosomes (me), and tight-junctions (tj) between adjoining cells. (C) Similar to primary fetal RPE cells, iPSC-derived RPE show a baseline calcium concentration of 110 nM. Addition of ATP to the apical bath activates apical P2Y2 receptors resulting in a spike in intracellular calcium concentration. (D) Apical and basal membrane resting potentials were measured in response to changing potassium (K) and ATP concentrations in the apical bath. Similar to the primary cultures of human RPE, these cells hyperpolarize when K concentration is reduced to 1 mM and depolarize when ATP is added to the apical bath.

Figure 27C:
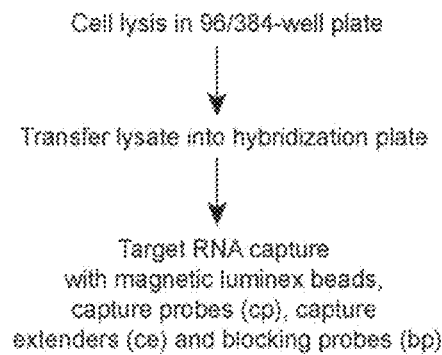
Figure 27B:
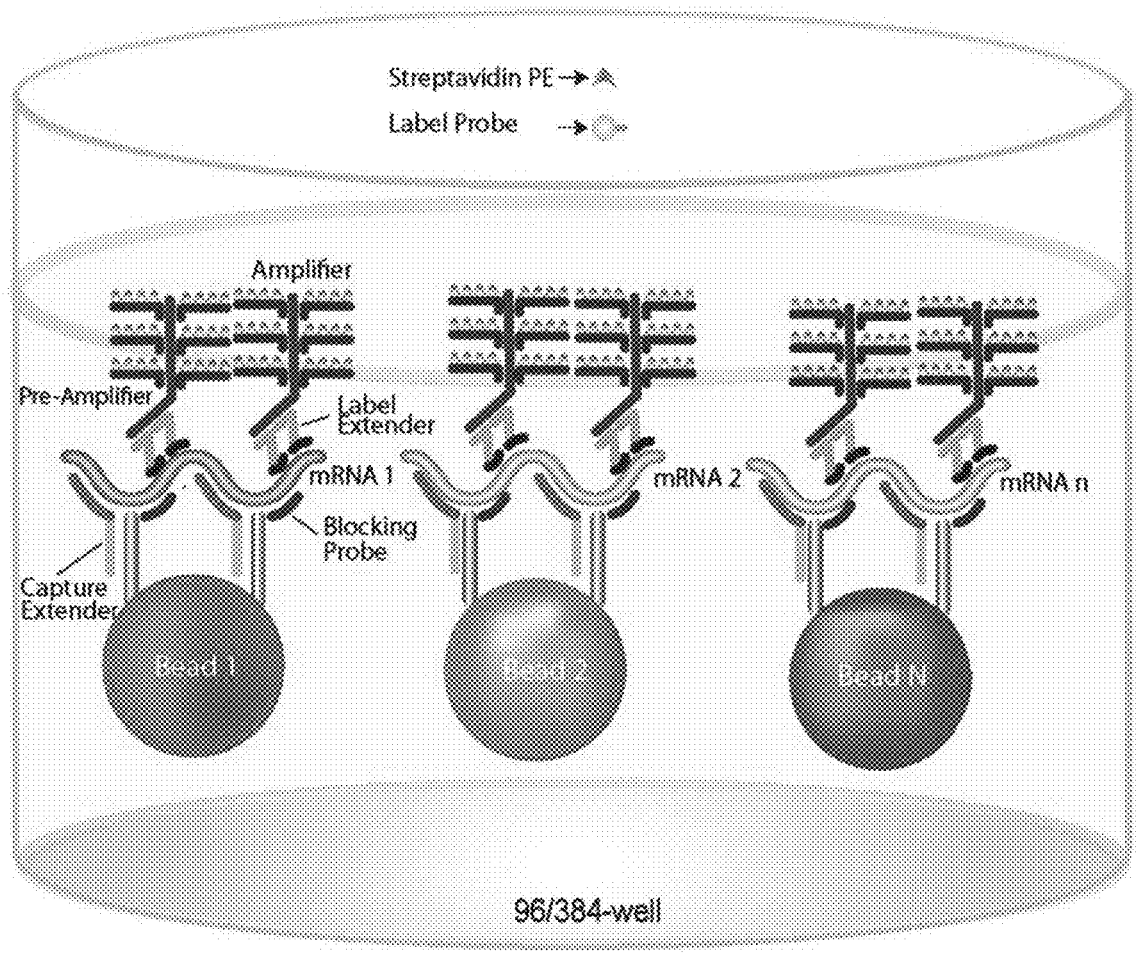

FIGS. 27A-27C show a schematic of the multiplex assay performed in a 96/384-well plate format. (A) Brief summary and the time line for the multiplex assay performed using iPSC-derived RPE. Assay can be performed in a day and a half with full automation. (B) Magnetic beads labeled with a unique fluorophores capture specific mRNAs through anti-sense oligo-nucleotide interactions of capture probe (CP) and multiple capture extenders (CEs). CE is a branched oligo-nucleotide; one side of it is anti-sense to CP and the other side has variable sequence that it anti-sense to the specific mRNA. Label extender (LE) also a branched oligo-nucleotide that binds to different regions of the mRNA and allows the binding of pre-amplifier and amplifier oligos through anti-sense interactions. Biotin containing label probes and streptavidin-conjugated phycoerythrin (SAPE) bind to amplifier oligos and are detected using the Luminex flow reader. (C) Table summarizes mRNA detected in this assay, their accession numbers, length, and the region where capture extenders and label extenders bind.

FIGS. 28A-28H show proof of principle for multiplex gene expression assay in 96-well plates. (A-D) Bright field images of iPSCs and RPE cells growing in a 96-well plate. (A) iPSCs (28B, C) iPSC-derived RPE seeded at two different cell densities (25,000 cells/well and 50,000 cells/well) (D) Primary human fetal RPE (50,000 cells/well). (E-H) Results obtained in the multiplex assay. (E, G) Expression of indicated genes was normalized to geomean of HPRT1 and B2M genes. Results are show as fold change in gene expression in iPSC-derived RPE seeded at lower cell density (white bar) and seeded at higher cell density (black bar) normalized either to undifferentiated iPSCs (28E) or to the primary fetal RPE (G). (F, H) Pearson's correlation analysis between gene expression results obtained from the qRT-PCR assay and the results obtained from the multiplex gene expression assay performed in 96-well plates. The correlation is significant for iPSCs (r=0.687) and highly significant for primary RPE cells (r=0.751).

Figure 29:
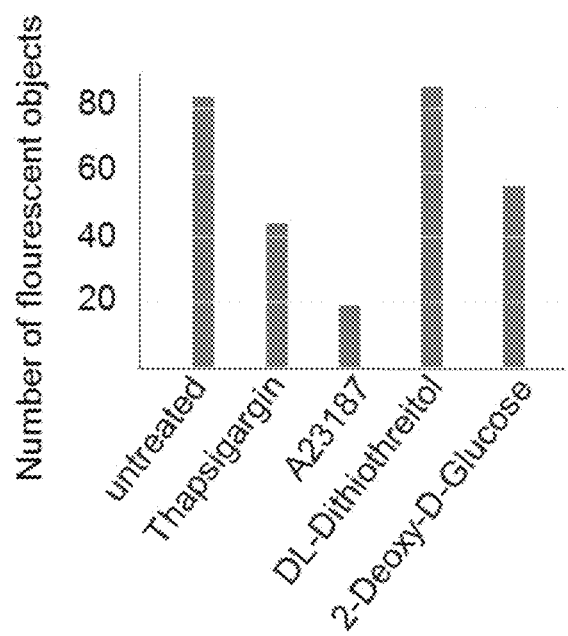

FIG. 29 is a bar graph showing the sensitivity of iPSC-derived RPE cells to various proteotoxic stressors. RPE cells differentiated from the reporter iPS cell line were grown in 384-well plates and treated with indicated stressors (conc. 10 µM). GRP signals were measured four days after the treatment. Thapsigargin, A23187, and 2-Deoxy-D-Glucose affected RPE phenotype.

Figure 30:
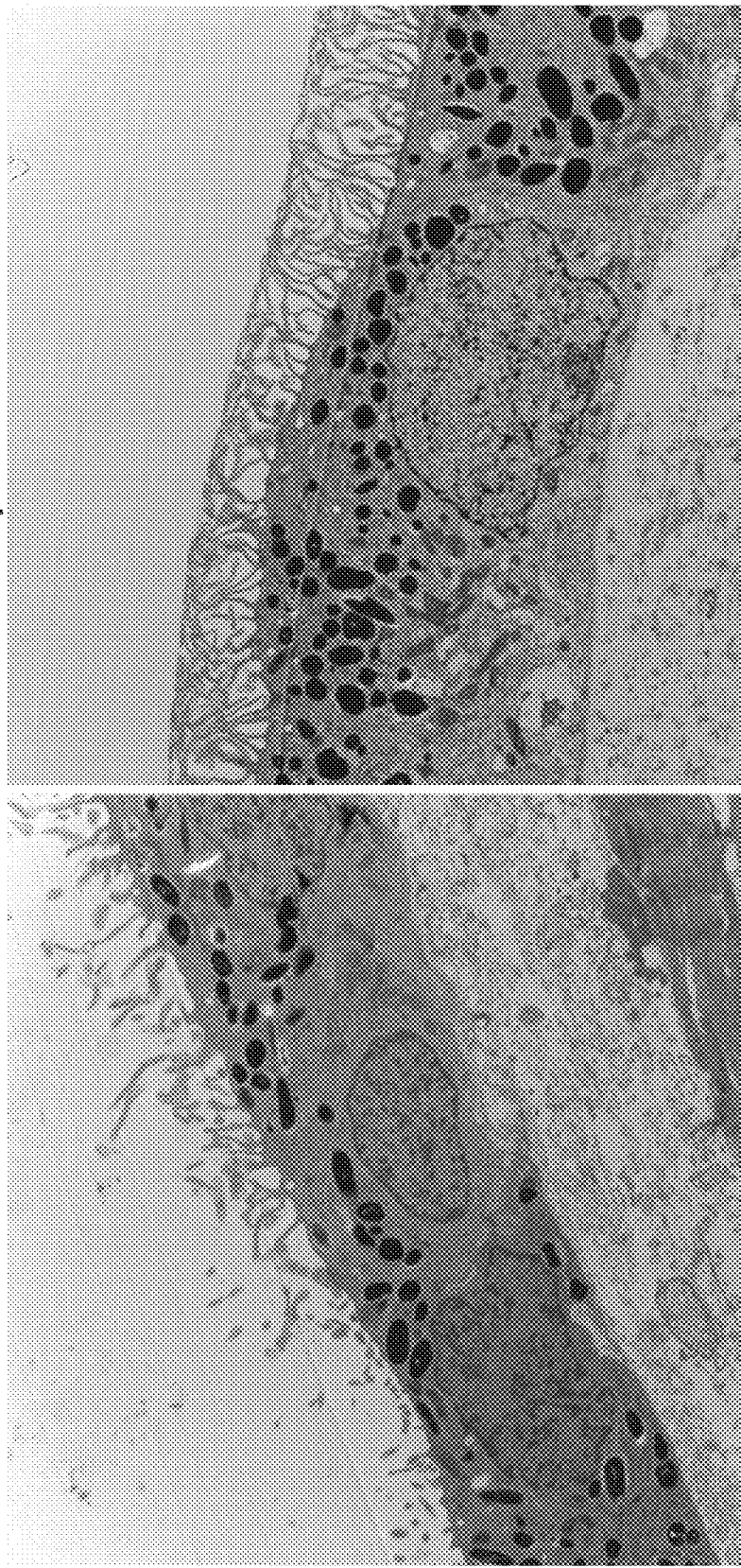

FIG. 30 is a digital image showing that aphidicolin treatment generates polarized retinal pigment epithelia cells. The retinal pigment epithelial cells treated with aphidicolon treatment have more extensive apical process as compared to non-treated cells.

Figure 31:
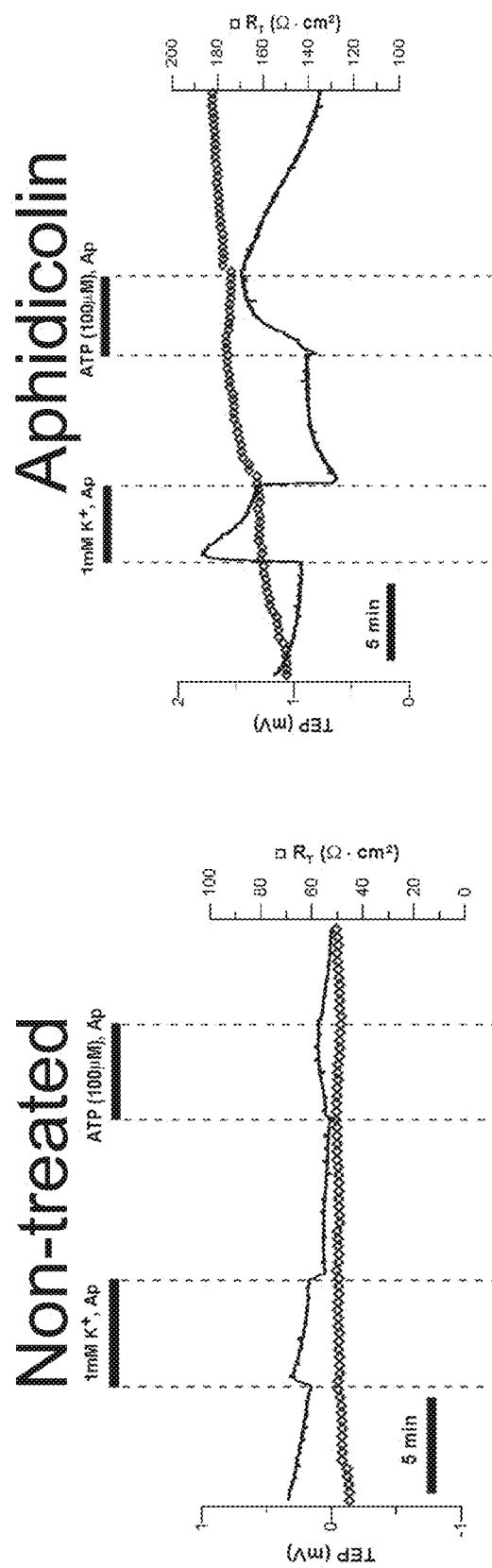
Figure 32A:
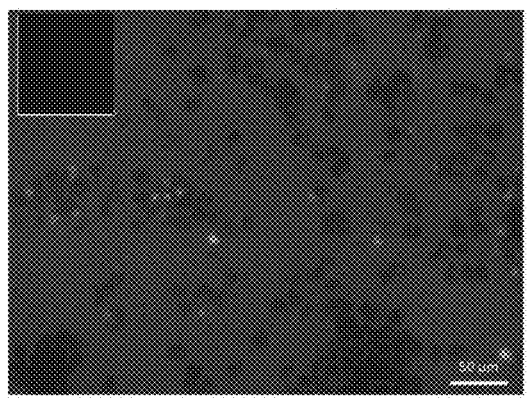
Figure 32B:
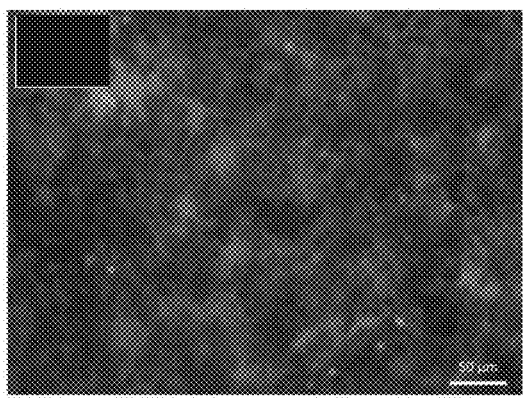
Figure 32C:
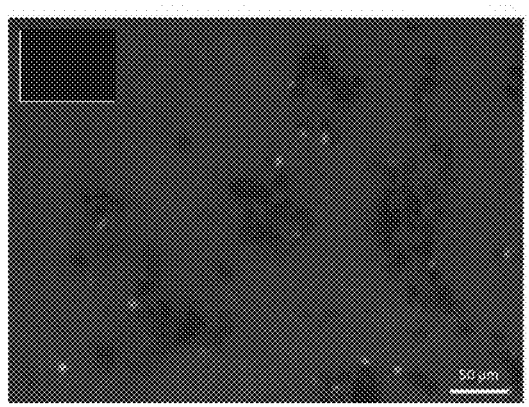
Figure 32D:
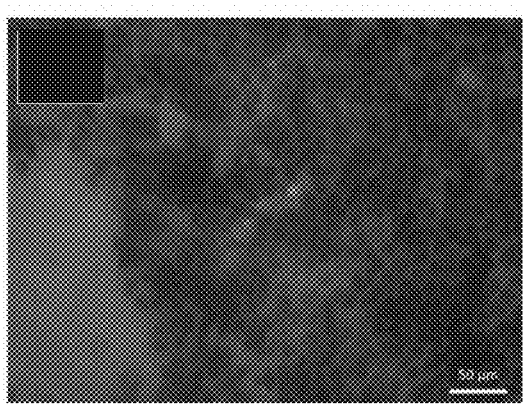

FIG. 31 is a set of graphs showing that aphidicolin treatment improves the function of iPSC derived retinal pigment epithelial cells. RPE cells treated with aphidicolin have higher transepithelial resistance, membrane potential, and show better physiological responses such as the ability to hyperpolarize in response to low potassium concentration or ATP application on the apical side.

FIGS. 32A-32D are digital images showing alginate coating enhances cell viability and reduces cell detachment during cryopreservation. Cell death assessed by ethidium homodimer-1 staining (grey). (A) Monolayer cryopreserved without alginate treatment using CRYOSTOR® CS10 solution. (B) Monolayer cryopreserved with alginate coating using CRYOSTOR® CS10 solution. (C) Monolayer cryopreserved without alginate coating using 10% DMSO media. (D) Monolayer cryopreserved with alginate coating using 10% DMSO media.

Figure 33:
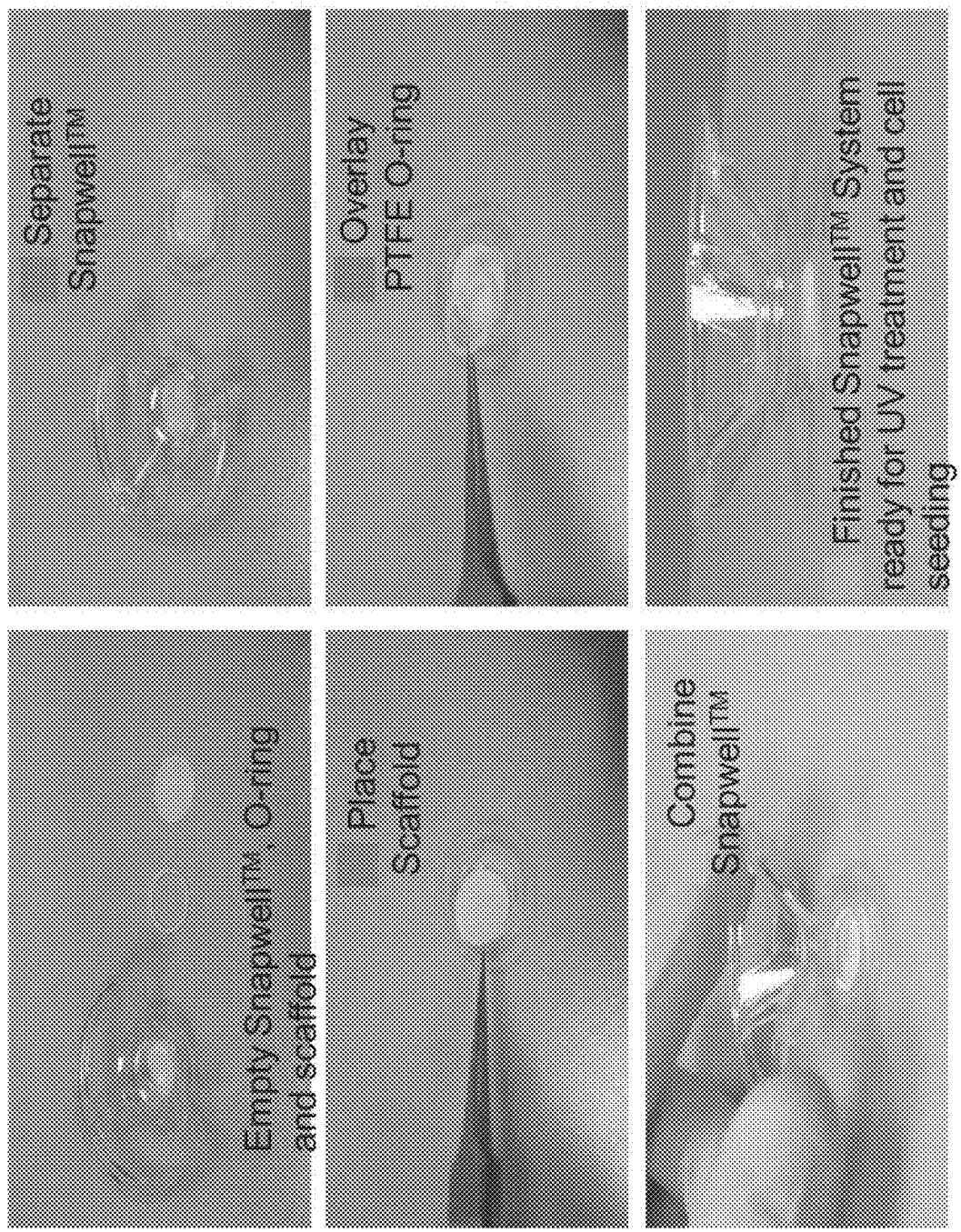

FIG. 33 is a set of digital images showing the protocol for growing iPSC-derived RPE on an artificial biodegradable scaffold using a SNAPWELL™ system.

Figures 34A, 34B:
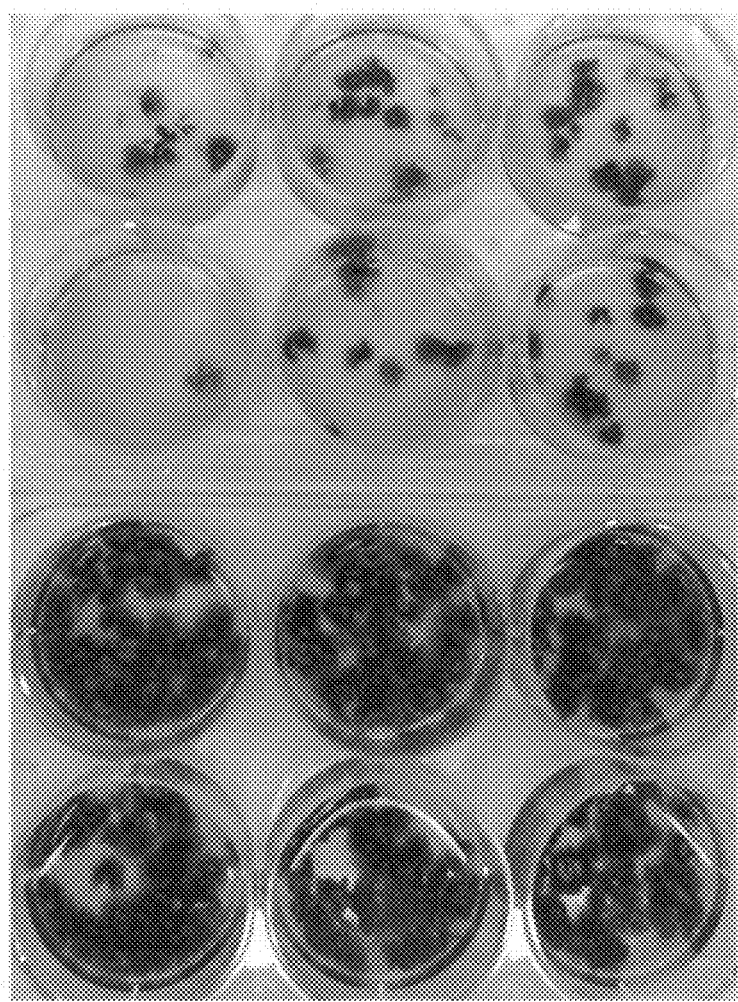
Figure 35E:
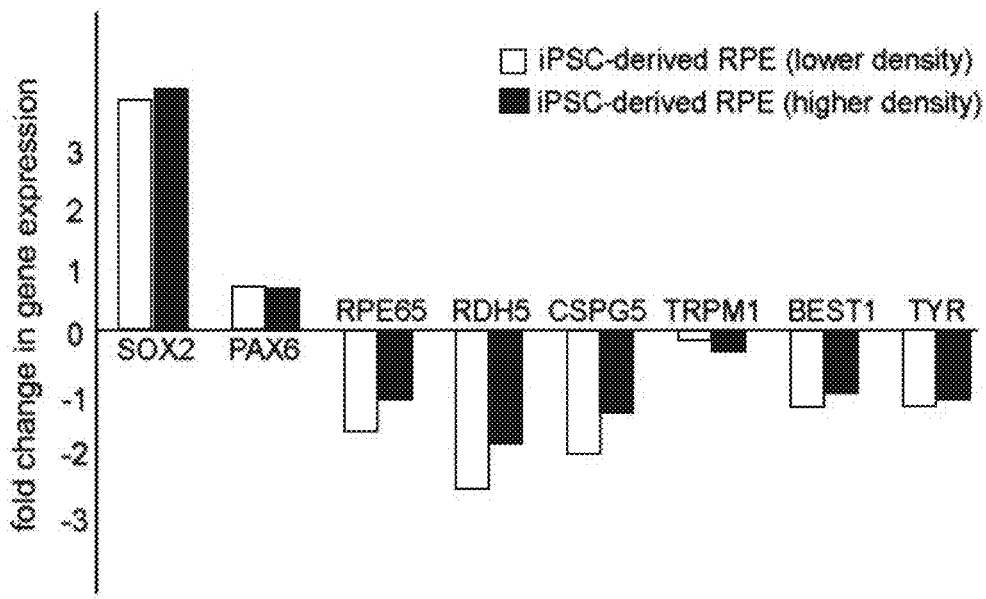
Figure 35F:
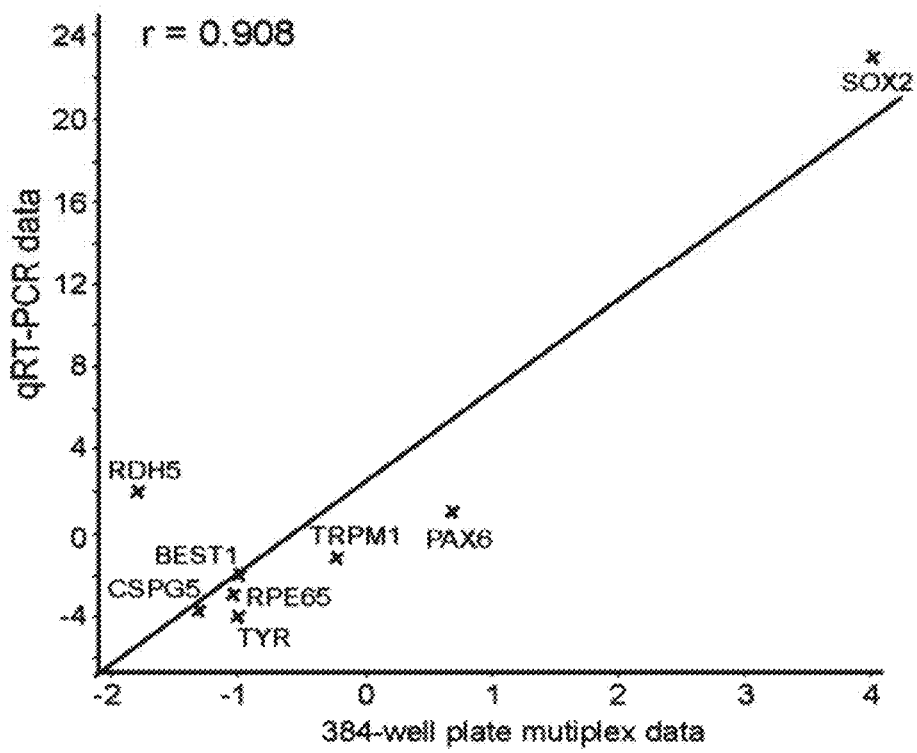
Figure 35G:
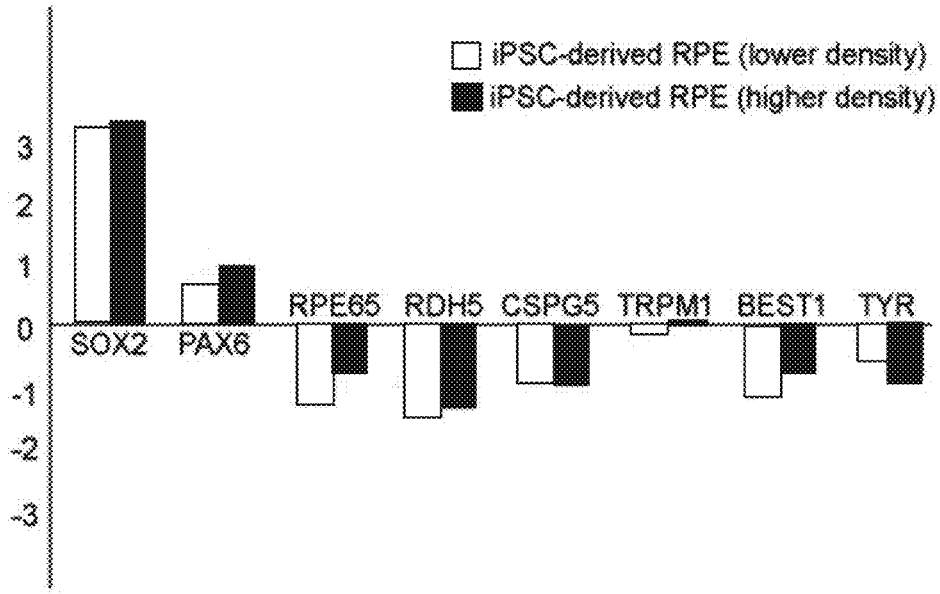
Figure 35H:
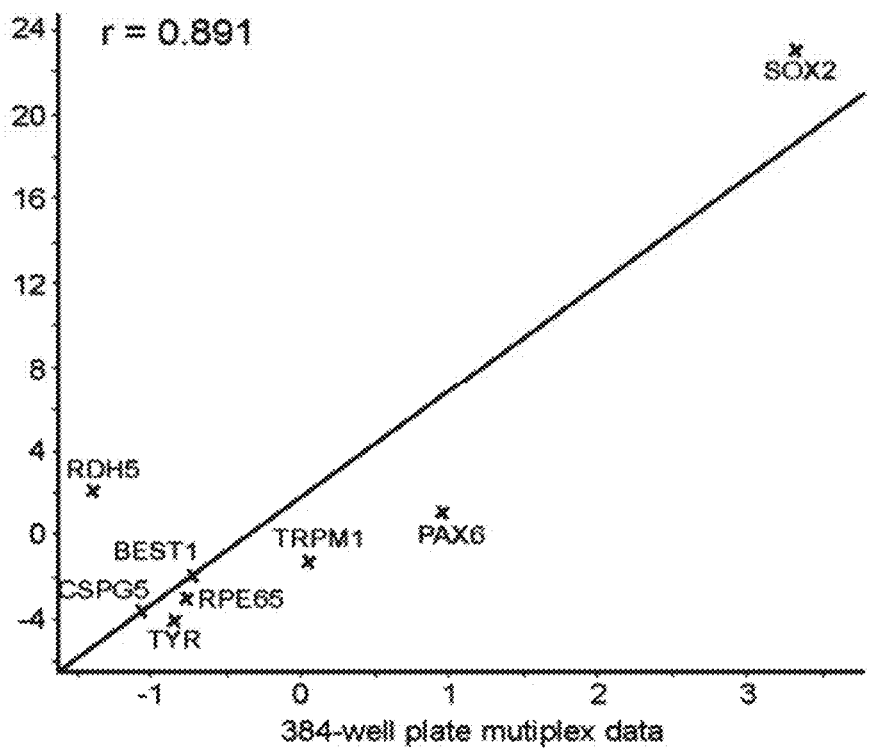
Figure 36A:
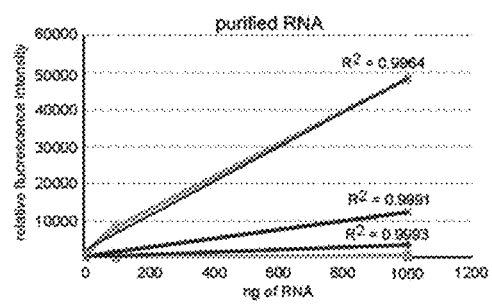
Figure 36B:
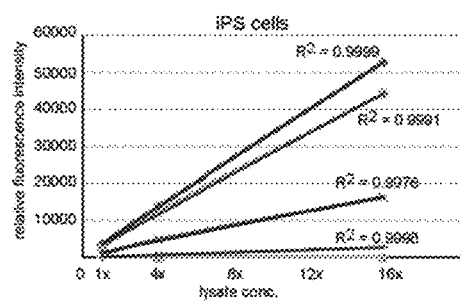
Figure 36C:
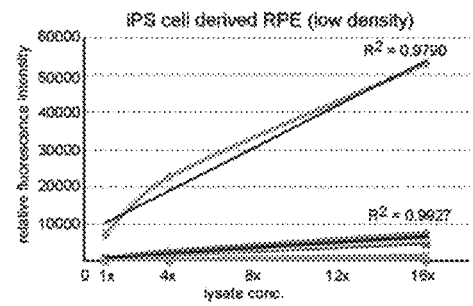
Figure 36D:
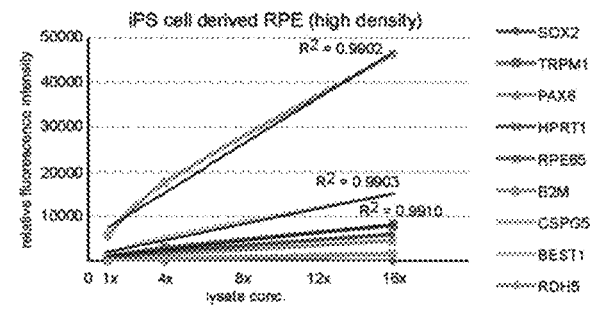
Figure 36E:
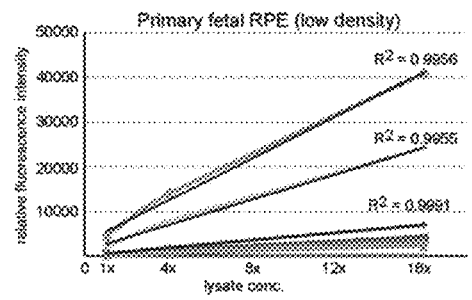
Figure 36F:
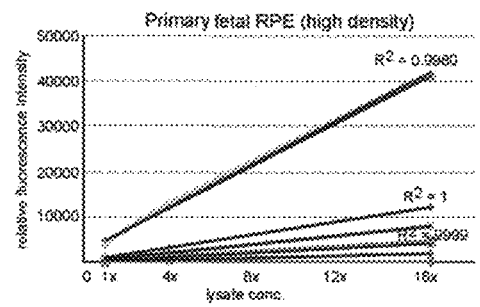

FIGS. 34A-34B are digital images showing pigmentation following culture of iPSCs in 10% (A) or 1.5% KOSR in RDM for the first 3 weeks of the differentiation protocol and photographed after 16 weeks in culture.

FIGS. 35A-35H show the proof of principle for multiplex gene expression assay in 384-well plates. Bright field images of iPSC-derived RPE (A, B) and human fetal RPE (C, D) seeded at two different cell densities growing in 384-well plates. (E, G) Fold change in gene expression in iPSC-derived RPE seeded at lower cell density (white bar) and seeded at higher cell density (black bar) normalized to the higher cell density of primary fetal RPE. Expression of indicated genes was normalized to geomean of HPRT1 and B2M housekeeping genes. Almost identical results were obtained with high bead number (E) and low bead number (G). Pearson's correlation analysis shows a very high correlation between results obtained from the qRT-PCR assay and the results obtained from 384-well multiplex gene expression assay. The coefficient values are r=0.908 and r=0.891 respectively for different number of beads.

FIGS. 36A-36F show the detection range of probes used for the multiplex assay. Four fold serial dilution of (A) purified human RPE, (B) iPSCs, (C) iPSC-derived RPE (low density), (D) iPSC-derived RPE (high density), (E) primary fetal RPE (low density), and (F) primary fetal RPE (high density) were used to determine range of detection of probe sets used for the multiplex assay. R2 value for each probe was more than 0.9 suggesting a linear range of detection over 16-fold dilution of the lysates.

SEQUENCE LISTING

The Sequence Listing is submitted as an ASCII text file 4239-89784-16_Sequence_Listing.txt, May 2, 2018, 8.05 KB], which is incorporated by reference herein.

The nucleic and amino acid sequences are shown using standard letter abbreviations for nucleotide bases, and one or three letter code for amino acids, as defined in 37 C.F.R. 1.822. Only one strand of each nucleic acid sequence is shown, but the complementary strand is understood as included by any reference to the displayed strand.

SEQ ID NO: 1 is the nucleic acid sequence of an exemplary human tyrosinase enhancer.

SEQ ID NO: 2 is an exemplary promoter sequence.

DETAILED DESCRIPTION OF SEVERAL EMBODIMENTS

High efficiency methods for producing retinal pigment epithelial cells from induced pluripotent stem cells (iPSCs) are disclosed herein. The iPSCs are produced from somatic cells, including retinal pigment epithelial cells, such as fetal retinal pigment epithelial stem cells. In some embodiments, the cells are human.

The methods disclosed herein are used to produce large numbers of differentiated RPE cells for use in screening assays, to study the basic biology of the RPE, and as therapeutics. The RPE cells can include a tyrosinase enhancer operably linked to a nucleic acid encoding a marker. In some embodiments, RPE cells produced using the methods disclosed herein can be formulated and used to treat retinal degenerative diseases. Thus, compositions are disclosed that include RPE cells, including substantially purified preparations of RPE cells. Screening assays are also disclosed for the identification of agents that modulate RPE cell proliferation and/or alter RPE cell differentiation. Agents identified using such screening assays may be used in vitro or in vivo.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Activin: Members of the transforming growth factor beta (TGF-beta) superfamily which participate in regulation of several biological processes, including cell differentiation and proliferation. Activin A is a member of this family that mediates its biological effects through a complex of transmembrane receptor serine/threonine kinases, and binds to specific Activin A receptors. It is a dimer composed of two subunits. Activin A participates in regulation of stem cell maintenance, via SMAD-dependent activation transcription of marker of pluripotency like POU class 5 homeobox 1 (Oct-3/4), nanog, nodal, and nodal-signaling regulators, Left-right determination factor 1 and 2 (Lefty-B and Lefty-A). Activin A also stimulates transcription of several hormones such as Gonadotropin-releasing hormone. An exemplary sequence for Activin A is provided in GENBANK® Accession No. NM_002192.

Agent: Any protein, nucleic acid molecule (including chemically modified nucleic acids), compound, small molecule, organic compound, inorganic compound, or other molecule of interest. Agent can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject).

Agonist or Inducer: An agent that binds to a receptor of a cell or a ligand of such a receptor and triggers a response by that cell, often mimicking the action of a naturally occurring substance. In one embodiment, a Frizzled (Fzd) agonist binds to a Fzd receptor and potentiates or enhances the Wnt/beta-catenin signaling pathway.

Alter: A change in an effective amount of a substance or parameter of interest, such as a polynucleotide, polypeptide or a property of a cell. An alteration in polypeptide or polynucleotide or enzymatic activity can affect a physiological property of a cell, such as the differentiation, proliferation, or senescence of the cell. The amount of the substance can be changed by a difference in the amount of the substance produced, by a difference in the amount of the substance that has a desired function, or by a difference in the activation of the substance. The change can be an increase or a decrease. The alteration can be in vivo or in vitro. In several embodiments, altering is at least about a 50%, 60%, 70%, 80%, 90%, 95%, 96%, 97%, 98%, 99%, or 100% increase or decrease in the effective amount (level) of a substance, the proliferation and/or survival of a cells, or the activity of a protein, such as an enzyme.

Amplification: of a nucleic acid molecule (e.g., a DNA or RNA molecule) refers to use of a technique that increases the number of copies of a nucleic acid molecule in a sample. An example of amplification is polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques.

Other examples of amplification include quantitative real-time polymerase chain reaction (qPCR), strand displacement amplification, as disclosed in U.S. Pat. No. 5,744,311; transcription-free isothermal amplification, as disclosed in U.S. Pat. No. 6,033,881; repair chain reaction amplification, as disclosed in PCT publication WO 90/01069; ligase chain reaction amplification, as disclosed in European patent publication EP-A-320,308; gap filling ligase chain reaction amplification, as disclosed in U.S. Pat. No. 5,427,930; and NASBA RNA transcription-free amplification, as disclosed in U.S. Pat. No. 6,025,134.

Animal: Living multi-cellular vertebrate organisms, a category that includes, for example, mammals and birds. The term mammal includes both human and non-human mammals. Similarly, the term "subject" includes both human and veterinary subjects, for example, non-human primates, dogs, cats, horses, rabbits, pigs, mice, rats, and cows.

Antagonist or Inhibitor: An agent that blocks or dampens a biochemical or biological response when bound to a receptor or a ligand of the receptor. Antagonists mediate their effects through receptor interactions by preventing agonist-induced responses. In one embodiment, a Frizzled (Fzd) antagonist binds to a Fzd receptor or to a Fzd ligand (such as Wnt) and inhibits the Wnt/beta-catenin signaling pathway.

Antibody: A polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Differentiation: Refers to the process whereby relatively unspecialized cells (such as embryonic stem cells or other stem cells) acquire specialized structural and/or functional features characteristic of mature cells. Similarly, "differentiate" refers to this process. Typically, during differentiation, cellular structure alters and tissue-specific proteins appear.

Embryoid Bodies: Three-dimensional aggregates of pluripotent stem cells. These cells can undergo differentiation into cells of the endoderm, mesoderm and ectoderm. In contrast to monolayer cultures, the spheroid structures that are formed when pluripotent stem cells aggregate enables the non-adherent culture of EBs in suspension, which is useful for bioprocessing approaches. The three-dimensional structure, including the establishment of complex cell adhesions and paracrine signaling within the EB microenvironment, enables differentiation and morphogenesis.

Embryo: A cellular mass obtained by one or more divisions of a zygote or an activated oocyte with an artificially reprogrammed nucleus without regard to whether it has been implanted into a female. A "morula" is the preimplantation embryo 3-4 days after fertilization, when it is a solid mass, generally composed of 12-32 cells (blastomeres). A "blastocyst" refers to a preimplantation embryo in placental mammals (about 3 days after fertilization in the mouse, about 5 days after fertilization in humans) of about 30-150 cells. The blastocyst stage follows the morula stage, and can be distinguished by its unique morphology. The blastocyst is generally a sphere made up of a layer of cells (the trophectoderm), a fluid-filled cavity (the blastocoel or blastocyst cavity), and a cluster of cells on the interior (the inner cell mass, ICM). The ICM, consisting of undifferentiated cells, gives rise to what will become the fetus if the blastocyst is implanted in a uterus.

Embryonic stem cells: Embryonic cells derived from the inner cell mass of blastocysts or morulae, optionally that have been serially passaged as cell lines. The term includes cells isolated from one or more blastomeres of an embryo, preferably without destroying the remainder of the embryo. The term also includes cells produced by somatic cell nuclear transfer. "Human embryonic stem cells" (hES cells) includes embryonic cells derived from the inner cell mass of human blastocysts or morulae, optionally that have been serially passaged as cell lines. The hES cells may be derived from fertilization of an egg cell with sperm or DNA, nuclear transfer, parthenogenesis, or by means to generate hES cells with homozygosity in the HLA region. Human ES cells can be produced or derived from a zygote, blastomeres, or blastocyst-staged mammalian embryo produced by the fusion of a sperm and egg cell, nuclear transfer, parthenogenesis, or the reprogramming of chromatin and subsequent incorporation of the reprogrammed chromatin into a plasma membrane to produce an embryonic cell. Human embryonic stem cells include, but are not limited to, MAO1, MAO9, ACT-4, No. 3, H1, H7, H9, H14 and ACT30 embryonic stem cells. Human embryonic stem cells, regardless of their source or the particular method use to produce them, can be identified based on (i) the ability to differentiate into cells of all three germ layers, (ii) expression of at least Oct-4 and alkaline phosphatase, and (iii) ability to produce teratomas when transplanted into immunocompromised animals.

Expand: A process by which the number or amount of cells in a cell culture is increased due to cell division. Similarly, the terms "expansion" or "expanded" refers to this process. The terms "proliferate," "proliferation" or "proliferated" may be used interchangeably with the words "expand," "expansion", or "expanded." Typically, during an expansion phase, the cells do not differentiate to form mature cells, but divide to form more cells.

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced.

Feeder layer: Non-proliferating cells (such as irradiated cells) that can be used to support proliferation of stem cells. Protocols for the production of feeder layers are known in the art, and are available on the internet, such as at the National Stem Cell Resource website, which is maintained by the American Type Culture Collection (ATCC).

Fetus: A developing mammal at an embryonic stage before birth. In humans, the fetal stage of prenatal development starts at the beginning of the 9th week after fertilization. In human eyes and RPE are already formed at 4 weeks from conception. RPE continues to mature for next several weeks.

Fibroblast growth factor (FGF): Any suitable fibroblast growth factor, derived from any animal, and functional fragments thereof, such as those that bind the receptor and induce biological effects related to activation of the receptor. A variety of FGFs are known and include, but are not limited to, FGF-1 (acidic fibroblast growth factor), FGF-2 (basic fibroblast growth factor, bFGF), FGF-3 (int-2), FGF-4 (hst/K-FGF), FGF-5, FGF-6, FGF-7, FGF-8, FGF-9 and FGF-98. "FGF" refers to a fibroblast growth factor protein such as FGF-1, FGF-2, FGF-4, FGF-6, FGF-8, FGF-9 or FGF-98, or a biologically active fragment or mutant thereof. The FGF can be from any animal species. In one embodiment, the FGF is mammalian FGF, including but not limited to, rodent, avian, canine, bovine, porcine, equine and human.

The amino acid sequences and method for making many of the FGFs are well known in the art.

The amino acid sequence of human bFGF and methods for its recombinant expression are disclosed in U.S. Pat. No. 5,439,818, herein incorporated by reference. The amino acid sequence of bovine bFGF and various methods for its recombinant expression are disclosed in U.S. Pat. No. 5,155,214, also herein incorporated by reference. When the 146 residue forms are compared, their amino acid sequences are nearly identical, with only two residues that differ. Recombinant bFGF-2, and other FGFs, can be purified to pharmaceutical quality (98% or greater purity) using the techniques described in detail in U.S. Pat. No. 4,956,455.

An FGF inducer includes an active fragment of FGF. In its simplest form, the active fragment is made by the removal of the N-terminal methionine, using well-known techniques for N-terminal methionine removal, such as a treatment with a methionine aminopeptidase. A second desirable truncation includes an FGF without its leader sequence. Those skilled in the art recognize the leader sequence as the series of hydrophobic residues at the N-terminus of a protein that facilitate its passage through a cell membrane but that are not necessary for activity and that are not found on the mature protein. Human and murine bFGF are commercially available.

Frizzled (Fzd): A family of seven-pass transmembrane mammalian proteins that have characteristics of G-protein-coupled receptors and that bind proteins of the Wnt family of lipoglycoproteins, secreted Frizzled-related proteins (sFRPs), R-spondin, and Norrin and activates downstream signaling. Frizzled proteins (also referred to as Frizzled receptors) contain a cysteine-rich domain (CRD) that binds its cognate ligands, a carboxy terminal PDZ (Psd-95/disc large/ZO-1 homologous)-binding domain, and various consensus sites for serine/threonine kinases and tyrosine kinases Amino acid hydropathy analysis indicates that the Frizzled proteins contain one extracellular amino terminus, three extracellular protein loops, three intracellular protein loops, and an intracellular carboxy terminus.

Frizzled proteins have an important regulatory role during embryonic development and have also been associated, in humans and in animal models, with a number of diseases, including various cancers, cardiac hypertrophy, familial exudative vitreoretinopathy, and schizophrenia.

There are at least 10 mammalian Frizzled proteins and the genes encoding the mammalian Frizzled proteins are related to the *Drosophila* frizzled genes. The human Frizzled proteins include Frizzled1 (Fzd1; GENBANK® Accession No. AB017363), Frizzled2 (Fzd2; GENBANK® Accession Nos. L37882/NM_001466), Frizzled3 (Fzd3; GENBANK® Accession No. AJ272427), Frizzled4 (Fzd4; GENBANK® Accession No. AB032417), Frizzled5 (Fzd5; GENBANK® Accession No. U43318), Frizzled6 (Fzd6; GENBANK® Accession No. AB012911), Frizzled7 (Fzd7; GENBANK® Accession No. AB010881), Frizzled8 (Fzd8; GENBANK® Accession No. AB043703), Frizzled9 (Fzd9; GENBANK® Accession Nos. U82169/NM_003508) and Frizzled10 (Fzd10; GENBANK® Accession No. AB027464). All of the GENBANK® entries are incorporated herein by reference as available on Jan. 1, 2013.

Growth factor: A substance that promotes cell growth, survival, and/or differentiation. Growth factors include molecules that function as growth stimulators (mitogens), factors that stimulate cell migration, factors that function as chemotactic agents or inhibit cell migration or invasion of tumor cells, factors that modulate differentiated functions of cells, factors involved in apoptosis, or factors that promote survival of cells without influencing growth and differentiation. Examples of growth factors are a fibroblast growth factor (such as FGF-2), epidermal growth factor (EGF), cilliary neurotrophic factor (CNTF), and nerve growth factor (NGF), and actvin-A.

Growth medium or expansion medium: A synthetic set of culture conditions with the nutrients necessary to support the growth (cell proliferation/expansion) of a specific population of cells. In one embodiment, the cells are stem cells, such as iPSCs. Growth media generally include a carbon source, a nitrogen source and a buffer to maintain pH. In one embodiment, growth medium contains a minimal essential media, such as DMEM, supplemented with various nutrients to enhance stem cell growth. Additionally, the minimal essential media may be supplemented with additives such as horse, calf or fetal bovine serum.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Isolated: An "isolated" biological component, such as a nucleic acid, protein or organelle that has been substantially separated or purified away from other biological components in the environment (such as a cell) in which the component naturally occurs, i.e., chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins. Similarly, an "isolated" cell has been substantially separated, produced apart from, or purified away from other cells of the organism in which the cell naturally occurs. Isolated cells can be, for example, at least 99%, at least 98%, at least 97%, at least 96%, 95%, at least 94%, at least 93%, at least 92%, or at least 90% pure.

Mammal: This term includes both human and non-human mammals. Examples of mammals include, but are not limited to: humans and veterinary and laboratory animals, such as pigs, cows, goats, cats, dogs, rabbits and mice.

Marker or Label: An agent capable of detection, for example by ELISA, spectrophotometry, flow cytometry, immunohistochemistry, immunofluorescence, microscopy, Northern analysis or Southern analysis. For example, a marker can be attached to a nucleic acid molecule or protein, thereby permitting detection of the nucleic acid molecule or protein. Examples of markers include, but are not limited to, radioactive isotopes, nitroimidazoles, enzyme substrates, co-factors, ligands, chemiluminescent agents, fluorophores, haptens, enzymes, and combinations thereof. Methods for labeling and guidance in the choice of markers appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

In some embodiments, the marker is a fluorophore ("fluorescent label"). Fluorophores are chemical compounds, which when excited by exposure to a particular wavelength of light, emits light (i.e., fluoresces), for example at a different wavelength. Fluorophores can be described in terms of their emission profile, or "color." Green fluorophores, for example Cy3, FITC, and Oregon Green, are characterized by their emission at wavelengths generally in the range of 515-540λ. Red fluorophores, for example Texas Red, Cy5 and tetramethylrhodamine, are characterized by their emission at wavelengths generally in the range of 590-690λ. In other embodiments, the marker is a protein tag recognized by an antibody, for example a histidine (His)-tag, a hemagglutinin (HA)-tag, or a c-Myc-tag.

Membrane potential: The electrical potential of the interior of the cell with respect to the environment, such as an external bath solution. One of skill in the art can readily assess the membrane potential of a cell, such as by using conventional whole cell techniques. The membrane potential can be assessed using many approaches, such as using conventional whole cell access, or using, for example, perforated-patch whole-cell and cell-attached configurations.

MicroRNA (miRNA): A single-stranded RNA molecule, which regulates gene expression. miRNAs are encoded by genes from whose DNA they are transcribed but miRNAs are not translated into protein; instead each primary transcript (a pri-miRNA) is processed into a short stem-loop structure called a pre-miRNA and finally into a functional miRNA. Mature miRNA molecules are either fully or partially complementary to one or more messenger RNA (mRNA) molecules, and their main function is to down-regulate gene expression. MicroRNAs can be encoded by independent genes, but also be processed (via the enzyme Dicer) from a variety of different RNA species, including introns, 3' UTRs of mRNAs, long noncoding RNAs, snoRNAs and transposons. As used herein, microRNAs also include "mimic" microRNAs which are intended to mean a microRNA exogenously introduced into a cell that have the same or substantially the same function as their endogenous counterpart.

Nodal: A secretory protein encoded by the NODAL gene that belongs to the Transforming Growth Factor (TGF-beta) superfamily During embryonic development, the left-right (LR) asymmetry of visceral organs in vertebrates is established through nodal signaling. Nodal is expressed in the left side of the organism in early development and it is highly conserved among deuterostomes. Exemplary Nodal sequences can be found as GENBANK® Accession Nos. NM_018055.4 and NP_060525.3, Jan. 6, 2013, which are incorporated by reference herein.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. It will be understood that when a nucleotide sequence is represented by a DNA sequence (i.e., A, T, G, C), this also includes an RNA sequence (i.e., A, U, G, C) in which "U" replaces "T."

"Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for example, rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns. In some examples, a nucleic acid encodes a disclosed antigen.

Noggin: A protein which is encoded by the NOG gene. Noggin inhibits TGF-β signal transduction by binding to TGF-β family ligands and preventing them from binding to their corresponding receptors. Noggin plays a key role in neural induction by inhibiting BMP4, along with other TGF-β signaling inhibitors such as chordin and follistatin. Exemplary sequences for Noggin are GENBANK® Accession Nos. NP_005441.1 and NM_005450.4, Jan. 13, 2013, which are incorporated herein by reference.

Oct-4: A protein also known as POU5-F1 or MGC22487 or OCT3 or OCT4 or OTF3 or OTF4, that is the gene product of the Oct-4 gene. The term includes Oct-4 from any species or source and includes analogs and fragments or portions of Oct-4 that retain the ability to be used for the production of iPSCs. The Oct-4 protein may have any of the known published sequences for Oct-4 which can be obtained from public sources such as GENBANK®. An example of such a sequence includes, but is not limited to, GENBANK® Accession No. NM_002701.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: Conventional pharmaceutically acceptable carriers are useful for practicing the methods and forming the compositions disclosed herein. *Remington's Pharmaceutical Sciences*, by E. W. Martin, Mack Publishing Co., Easton, Pa., 15th Edition, 1975, describes examples of compositions and formulations suitable for pharmaceutical delivery of the antimicrobial compounds herein disclosed.

In general, the nature of the carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pluripotent stem cells: Stem cells that: (a) are capable of inducing teratomas when transplanted in immunodeficient (SCID) mice; (b) are capable of differentiating to cell types of all three germ layers (e.g., can differentiate to ectodermal, mesodermal, and endodermal cell types); and (c) express one or more markers of embryonic stem cells (e.g., express Oct 4, alkaline phosphatase, SSEA-3 surface antigen, SSEA-4 surface antigen, nanog, TRA-1-60, TRA-1-81, SOX2, REX1, etc), but that cannot form an embryo and the extraembryonic membranes (are not totipotent).

Exemplary pluripotent stem cells include embryonic stem cells derived from the inner cell mass (ICM) of blastocyst stage embryos, as well as embryonic stem cells derived from one or more blastomeres of a cleavage stage or morula stage embryo (optionally without destroying the remainder of the embryo). These embryonic stem cells can be generated from embryonic material produced by fertilization or by asexual means, including somatic cell nuclear transfer (SCNT), parthenogenesis, and androgenesis. PSCs alone cannot develop into a fetal or adult animal when transplanted in utero because they lack the potential to contribute to all extraembryonic tissue (e.g., placenta in vivo or trophoblast in vitro).

Pluripotent stem cells also include "induced pluripotent stem cells (iPSCs)" generated by reprogramming a somatic cell by expressing or inducing expression of a combination of factors (herein referred to as reprogramming factors). iPSCs can be generated using fetal, postnatal, newborn, juvenile, or adult somatic cells. In certain embodiments, factors that can be used to reprogram somatic cells to pluripotent stem cells include, for example, Oct4 (sometimes referred to as Oct 3/4), Sox2, c-Myc, and Klf4, Nanog, and Lin28. In some embodiments, somatic cells are reprogrammed by expressing at least two reprogramming factors, at least three reprogramming factors, or four reprogramming factors to reprogram a somatic cell to a pluripotent stem cell. iPSCs are similar in properties to embryonic stem cells.

Polypeptide: A polymer in which the monomers are amino acid residues that are joined together through amide bonds. When the amino acids are alpha-amino acids, either the L-optical isomer or the D-optical isomer can be used, the L-isomers being preferred in nature. The term polypeptide is specifically intended to cover naturally occurring proteins, as well as those that are recombinantly or synthetically produced.

Substantially purified polypeptide as used herein refers to a polypeptide that is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative amino acid substitution tables providing functionally similar amino acids are well known to one of ordinary skill in the art. The following six groups are examples of amino acids that are considered to be conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

A non-conservative amino acid substitution can result from changes in: (a) the structure of the amino acid backbone in the area of the substitution; (b) the charge or hydrophobicity of the amino acid; or (c) the bulk of an amino acid side chain. Substitutions generally expected to produce the greatest changes in protein properties are those in which: (a) a hydrophilic residue is substituted for (or by) a hydrophobic residue; (b) a proline is substituted for (or by) any other residue; (c) a residue having a bulky side chain, e.g., phenylalanine, is substituted for (or by) one not having a side chain, e.g., glycine; or (d) a residue having an electropositive side chain, e.g., lysyl, arginyl, or histadyl, is substituted for (or by) an electronegative residue, e.g., glutamyl or aspartyl.

Variant amino acid sequences may, for example, be 80, 90 or even 95 or 98% identical to the native amino acid sequence. Programs and algorithms for determining percentage identity can be found at the NCBI website.

Prenatal: Existing or occurring before birth. Similarly, "postnatal" is existing or occurring after birth.

Primers: Short nucleic acid molecules, for instance DNA oligonucleotides 10-100 nucleotides in length, such as about 15, 20, 25, 30 or 50 nucleotides or more in length. Primers can be annealed to a complementary target DNA strand (such as a gene listed in Table 1 or Table A, or miRNA listed in Table 2) by nucleic acid hybridization to form a hybrid between the primer and the target DNA strand. Primer pairs can be used for amplification of a nucleic acid sequence, such as by PCR or other nucleic acid amplification methods known in the art.

Methods for preparing and using nucleic acid primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular primer increases with its length. Thus, for example, a primer including 30 consecutive nucleotides of molecule will anneal to a target sequence, such as another homolog of the designated molecule, with a higher specificity than a corresponding primer of only 15 nucleotides. Thus, in order to obtain greater specificity, primers can be selected that include at least 20, at least 25, at least 30, at least 35, at least 40, at least 45, at least 50 or more consecutive nucleotides of a nucleic acid sequence of interest.

Primer pairs: Two primers (one "forward" and one "reverse") that can be used for amplification of a nucleic acid sequence, for example by polymerase chain reaction (PCR) or other in vitro nucleic-acid amplification methods. The forward and reverse primers of a primer pair do not hybridize to overlapping complementary sequences on the target nucleic acid sequence.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified oligonucleotide preparation is one in which the oligonucleotide is more pure than in an environment including a complex mixture of oligonucleotides. A purified population of cells is greater than about 90%, 91%, 92%, 93%, 94%, 95%, 96%, 97%, 98%, 99% or 100% pure, or free other cell types.

Recombinant: A recombinant nucleic acid or polypeptide molecule is one that has a sequence that is not naturally occurring or has a sequence that is made by an artificial combination of two otherwise separated segments of sequence. This artificial combination can be accomplished by chemical synthesis of polypeptide or nucleic acid molecules, or by the artificial manipulation of isolated segments of nucleic acid molecules, such as by genetic engineering techniques.

Retinal pigment epithelial (RPE) cell: RPE cells can be recognized based on pigmentation, epithelial morphology, and apical-basal polarized cells. RPE cells express, both at the mRNA and protein level, one or more of the following: Pax6, MITF, RPE65, CRALBP, PEDF, Bestrophin and/or Otx2. In certain other embodiments, the RPE cells express, both at the mRNA and protein level, one or more of Pax-6, MitF, and tyrosinase. RPE cells do not express (at any detectable level) the embryonic stem cell markers Oct-4, nanog, or Rex-1. Specifically, expression of these genes is approximately 100-1000 fold lower in RPE cells than in ES cells or iPSC cells, when assessed by quantitative RT-PCR. Differentiated RPE cells also can be visually recognized by their cobblestone morphology and the initial appearance of pigment. In addition, differentiated RPE cells have trans epithelial resistance/TER, and trans epithelial potential/TEP across the monolayer (TER>100 ohms·cm$^2$; TEP>2 mV), transport fluid and $CO_2$ from apical to basal side, and regulate a polarized secretion of cytokines.

The terms "RPE cell" and "differentiated RPE cell" and "iPSC-derived RPE cell" and "human RPE cell" are used interchangeably throughout to refer to an RPE cell differentiated from a human iPSC using the methods disclosed herein. The term is used generically to refer to differentiated RPE cells.

Retinal Pigment Epithelium: The pigmented layer of hexagonal cells, present in vivo in mammals, just outside of the neurosensory retinal that is attached to the underlying choroid. These cells are densely packed with pigment granules, and shield the retinal from incoming light. The retinal pigment epithelium also serves as the limiting transport factor that maintains the retinal environment by supplying small molecules such as amino acid, ascorbic acid and D-glucose while remaining a tight barrier to choroidal blood borne substances.

Secreted Frizzled-related protein (sFRP): The sFRP family of proteins are approximately 32-40 kDa glycoproteins that were identified as antagonists of Wnt signaling (Rattner et al. (1997) *Proc. Natl. Acad. Sci. USA* 94:2859-63; Melkonyan et al. (1997) *Proc. Natl. Acad. Sci. USA* 94:13636-41; Finch et al. (1997) *Proc. Natl. Acad. Sci. USA* 94:6770-5; Uren et al. (2000) *J. Biol. Chem.* 275:4374-82; Kawano et al. (2003) *J. Cell. Sci.* 116:2627-34). In mammals, there are five sFRPs. The human sFRPs include sFRP1 (GENBANK® Accession No. AF001900.1), sFRP2 (GENBANK® Accession No. NM_003013.2), sFRP3 (GENBANK® Accession No. U91903.1), sFRP4 (GENBANK® Accession No. NM_003014.3), and sFRP5 (GENBANK® Accession No. NM_003015.3), as available on Jan. 1, 2013.

The sFRPs contain three structural units: an amino terminal signal peptide, a Frizzled type cysteine-rich domain (CRD), and a carboxy-terminal netrin (NTR) domain. The CRD spans approximately 120 amino acids, contains 10 conserved cysteine residues, and has 30-50% sequence similarity to the CRD of Fzd receptors. The netrin domain is defined by six cysteine residues and several conserved segments of hydrophobic residues and secondary structures. The biological activity of sFRPs is largely attributed to their role as regulators of Wnt function.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Huang, et al., *Computer Applications in the Biosciences* 8:155-165, 1992; Pearson et al., *Methods in Molecular Biology* 24:307-331, 1994; Tatiana et al., (1999), *FEMS Microbiol. Lett.*, 174:247-250, 1999. Altschul et al. present a detailed consideration of sequence-alignment methods and homology calculations (*J. Mol. Biol.* 215:403-410, 1990).

The National Center for Biotechnology Information (NCBI) Basic Local Alignment Search Tool (BLAST™, Altschul et al. *J. Mol. Biol.* 215:403-410, 1990) is available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the internet under the help section for BLAST™.

Sonic hedgehog (SHH): Sonic hedgehog (SHH) is one of three mammalian homologs of the *Drosophila* hedgehog signaling molecule and is expressed at high levels in the notochord and floor plate of developing embryos. SHH is known to play a key role in neuronal tube patterning (Echerlard et al., Cell 75:1417-30, 1993), the development of limbs, somites, lungs and skin. Moreover, overexpression of SHH has been found in basal cell carcinoma. Exemplary amino acid sequences of SHH is set forth in U.S. Pat. No. 6,277,820. An exemplary sequence for human Sonic is set forth as GENBANK Accession No. NG_007504.1 (Jan. 1, 2013), which is incorporated by reference herein.

Subject: An animal or human subjected to a treatment, observation or experiment.

Totipotent or totipotency: A cell's ability to divide and ultimately produce an entire organism including all extraembryonic tissues in vivo. In one aspect, the term "totipotent" refers to the ability of the cell to progress through a series of divisions into a blastocyst in vitro. The blastocyst comprises an inner cell mass (ICM) and a trophectoderm. The cells found in the ICM give rise to pluripotent stem cells (PSCs) that possess the ability to proliferate indefinitely, or if properly induced, differentiate in all cell types contributing to an organism. Trophectoderm cells generate extraembryonic tissues, including placenta and amnion.

Treatment: Therapeutic measures that cure, slow down, lessen symptoms of, and/or halt progression of a diagnosed pathologic condition or disorder. In certain embodiments, treating a subject with a retinal disorder results in a decline in the deterioration of the retinal; an increase in the number of retinal pigment epithelial cells, an improvement in vision, or some combination of effects.

Tyrosinase: A copper-containing oxidase that catalyzes the production of melanin and other pigments from tyrosine by oxidation. This enzyme is the rate limiting enzyme for controlling the production of melanin. Tyrosinase acts in the hydroxylation of a monophenol and, the conversion of an o-diphenol to the corresponding o-quinone. o-Quinone undergoes several reactions to eventually form melanin. In humans, the tyrosinase enzyme is encoded by the TYR gene. Exemplary amino acid and nucleic acid sequences are set forth in GENBANK® Accession Nos. NM_000372.4 (human) and NM_011661.4 (mouse), Jan. 5, 2013, and which are incorporated by reference herein.

Undifferentiated: Cells that display characteristic markers and morphological characteristics of undifferentiated cells, distinguishing them from differentiated cells of embryo or adult origin. Thus, in some embodiments, undifferentiated cells do not express cell lineage specific markers, including, but no limited to, RPE markers.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art. A vector may also include a sequence encoding for an amino acid motif that facilitates the isolation of the desired protein product such as a sequence encoding maltose binding protein, c-myc, or GST.

Wnt: A family of highly conserved secreted signaling molecules that regulate cell-to-cell interactions and are related to the *Drosophila* segment polarity gene, wingless. In humans, the Wnt family of genes encodes 38 to 43 kDa cysteine rich glycoproteins. The Wnt proteins have a hydrophobic signal sequence, a conserved asparagine-linked oligosaccharide consensus sequence (see e.g., Shimizu et al *Cell Growth Differ* 8:1349-1358 (1997)) and 22 conserved cysteine residues. Because of their ability to promote stabilization of cytoplasmic beta-catenin, Wnt proteins can act as transcriptional activators and inhibit apoptosis. Overexpression of particular Wnt proteins has been shown to be associated with certain cancers.

The Wnt family contains at least 19 mammalian members. Exemplary Wnt proteins include Wnt-1, Wnt-2, Wnt2b, Wnt-3, Wnt-3a, Wnt-4, Wnt-5a, Wnt5b, Wnt-6, Wnt-7a, Wnt-7b, Wnt-8a, Wnt-8b, Wnt9a, Wnt9b, Wnt10a, Wnt-10b, Wnt-11, and Wnt 16. These secreted ligands activate at least three different signaling pathways. In the canonical (or Wnt/beta-catenin) Wnt signaling pathway, Wnt activates a receptor complex consisting of a Frizzled (Fzd) receptor family member and low-density lipoprotein (LDL) receptor-related protein 5 or 6 (LRP5/6). To form the receptor complex that binds the Fzd ligands, Fzd receptors interact with LRP5/6, single pass transmembrane proteins with four extracellular EGF-like domains separated by six YWTD amino acid repeats (Johnson et al., 2004, J. Bone Mineral Res. 19:1749). The canonical Wnt signaling pathway activated upon receptor binding is mediated by the cytoplasmic protein Dishevelled (Dvl) interacting directly with the Fzd receptor and results in the cytoplasmic stabilization and accumulation of beta-catenin. In the absence of a Wnt signal, beta-catenin is localized to a cytoplasmic destruction complex that includes the tumor suppressor proteins adenomatous polyposis coli (APC) and Axin. These proteins function as critical scaffolds to allow glycogen synthase kinase (GSK)-3beta to bind and phosphorylate beta-catenin, marking it for degradation via the ubiquitin/proteasome pathway. Activation of Dvl results in the dissociation of the destruction complex. Accumulated cytoplasmic beta-catenin is then transported into the nucleus where it interacts with the DNA-binding proteins of the TCF/LEF family to activate transcription.

The non-canonical WNT pathway is regulated by three of these WNT ligands—WNT4, WNT5a, and WNT11. These ligands bind to the WNT receptor Frizzled in the absence of the co-receptors (LRP5/6). This leads to the activation of the RHO GTPase and ROCK kinase without activating cytoplasmic beta-catenin. ROCK regulates cytoskeleton to regulate apical-basal polarity of the cell. Because of competition for the same receptor, non-canonical WNT ligands also lead to inhibition of canonical WNT signaling.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Methods for Reprogramming Somatic Cells to Produce RPE Cells

Methods are provided herein wherein induced pluripotent stem cells are reprogrammed to become retinal pigment epithelial cells. Stem cells can be indefinitely maintained in vitro in an undifferentiated state and yet are capable of differentiating into virtually any cell type. Disclosed herein are methods to induce the differentiation of human iPSC into a specialized cell in the neuronal lineage, the retinal pigment epithelium (RPE).

RPE is a densely pigmented epithelial monolayer between the choroid and neural retina that serves as a part of a barrier between the bloodstream and retina. The functions of the RPE include phagocytosis of shed rod and cone outer segments, absorption of stray light, vitamin A metabolism, regeneration of retinoids, and tissue repair. The RPE has a cobblestone cellular morphology of black pigmented cells, and is known to express markers such as cellular retinaldehyde-binding protein (CRALBP); RPE65, Best vitelliform macular dystrophy gene (VMD2), and pigment epithelium derived factor (PEDF). The RPE plays a role in photoreceptor maintenance, and various RPE malfunctions in vivo are associated with a number of vision-altering ailments, such as RPE detachment, dysplasia, atrophy, retinopathy, retinitis pigmentosa, macular dystrophy or degeneration, including age-related macular degeneration, which can result in photoreceptor damage and blindness. Because of its wound healing abilities, the RPE has been extensively studied for transplantation therapy; RPE transplantation can be used for vision restoration. Furthermore, RPE can be used for the treatment of Parkinson's disease, as the RPE secretes dopamine.

The starting somatic cell can be any cell of interest. Any cells other than germ cells of mammalian origin (such as, humans, mice, monkeys, pigs, rats etc.) can be used as starting material for the production of iPSCs. Examples include keratinizing epithelial cells, mucosal epithelial cells, exocrine gland epithelial cells, endocrine cells, liver cells, epithelial cells, endothelial cells, fibroblasts, muscle cells, cells of the blood and the immune system, cells of the nervous system including nerve cells and glia cells, pigment cells, and progenitor cells, including hematopoietic stem cells, amongst others. There is no limitation on the degree of cell differentiation, the age of an animal from which cells are collected and the like; even undifferentiated progenitor cells (including somatic stem cells) and finally differentiated mature cells can be used alike as sources of somatic cells in the present invention. In one embodiment, the somatic cell is itself a RPE cell such as a human RPE cell. The RPE cell can be an adult or a fetal RPE cell. Thus, in some embodiments, the somatic cell is a fetal human RPE cell, obtained from a human fetus of about week 9 to about week 38 of gestation, such as about week 9 to about week 16 of gestation, about week 17 to about week 25 of gestation, about 16 to about 19 weeks, or about week 26 to about week 38 of gestation. In this context, "about" means within 2 days.

The choice of mammalian individuals as a source of somatic cells is not particularly limited. Allogenic cells can be used. Thus, in some embodiments, the iPSCs are not matched for MHC (e.g., HLA). In some embodiments, when the iPSCs obtained are to be used for regenerative medicine in humans, cells can be collected from the somatic cells from the subject to be treated, or another subject with the same or substantially the same HLA type as that of the patient. "Substantially the same HLA type" indicates that the HLA type of donor matches with that of a patient to the extent that the transplanted cells, which have been obtained by inducing differentiation of iPSCs derived from the donor's somatic cells, can be engrafted when they are transplanted to the patient. The patient optionally can be treated with an immunosuppressant. In one example, it includes an HLA type wherein major HLAs (e.g., the three major loci of HLA-A, HLA-B and HLA-DR, the four major loci further including HLA-Cw) are identical.

Somatic cells isolated from a mammal can be pre-cultured using a medium known to be suitable for their cultivation according to the choice of cells before being subjected to the step of nuclear reprogramming Specific non-limiting examples of such media include, but are not limited to, minimal essential medium (MEM) containing about 5 to 20% fetal calf serum (FCS), Dulbecco's modified Eagle medium (DMEM), RPMI1640 medium, 199 medium, F12 medium, and the like. One of skill in the art can readily ascertain appropriate tissue culture conditions to propagate particular cell types from a mammal, such as a human. In some embodiments, to obtain completely xeno-free human iPSCs, the medium can exclude ingredients derived from non-human animals, such as FCS. Media comprising a basal medium supplemented with human-derived ingredients suitable for cultivation of various somatic cells (particularly, recombinant human proteins such as growth factors), non-essential amino acids, vitamins and the like are commercially available; those skilled in the art are able to choose an appropriate xeno-free medium according to the source of somatic cells. Somatic cells pre-cultured using a xeno-free medium are dissociated from the culture vessel using an appropriate xeno-free cell dissociation solution, and recovered, after which they are brought into contact with nuclear reprogramming substances.

Generally, cells are cultured at about 35 to 38° C., usually at 37° C., in about 4-6% $CO_2$, generally at 5% $CO_2$, unless specifically indicated otherwise below.

Somatic cells can be reprogrammed to produce induced pluripotent stem cells (iPSCs) using methods known to one of skill in the art. One of skill in the art can readily produce induced pluripotent stem cells, see for example, Published U.S. Patent Application No. 20090246875, Published U.S. Patent Application No. 2010/0210014; Published U.S. Patent Application No. 20120276636; U.S. Pat. Nos. 8,058,065; 8,129,187; 8,278,620; PCT Publication NO. WO 2007/069666 A1, and U.S. Pat. No. 8,268,620, which are incorporated herein by reference. Generally, nuclear reprogramming factors are used to produce pluripotent stem cells from a somatic cell. In some embodiments, at least three, or at least four, of Klf4, c-Myc, Oct3/4, Sox2, Nanog, and Lin28 are utilized. In other embodiments, Oct3/4, Sox2, c-Myc and Klf4 is utilized.

The cells are treated with a nuclear reprogramming substance, which is generally one or more factor(s) capable of inducing an iPSC from a somatic cell or a nucleic acid that encodes these substances (including forms integrated in a vector). The nuclear reprogramming substances generally include at least Oct3/4, Klf4 and Sox2 or nucleic acids that encode these molecules. A functional inhibitor of p53, L-myc or a nucleic acid that encodes L-myc, and Lin28 or Lin28b or a nucleic acid that encodes Lin28 or Lin28b, can be utilized as additional nuclear reprogramming substances. Nanog can also be utilized for nuclear reprogramming. As disclosed in published U.S. Patent Application No. 20120196360, exemplary reprogramming factors for the production of iPSCs include (1) Oct3/4, Klf4, Sox2, L-Myc (Sox2 can be replaced with Sox1, Sox3, Sox15, Sox17 or Sox18; Klf4 is replaceable with Klf1, Klf2 or Klf5); (2) Oct3/4, Klf4, Sox2, L-Myc, TERT, SV40 Large T antigen (SV40LT); (3) Oct3/4, Klf4, Sox2, L-Myc, TERT, human papilloma virus (HPV)16 E6; (4) Oct3/4, Klf4, Sox2, L-Myc, TERT, HPV16 E7 (5) Oct3/4, Klf4, Sox2, L-Myc, TERT, HPV16 E6, HPV16 E7; (6) Oct3/4, Klf4, Sox2, L-Myc, TERT, Bmi1; (7) Oct3/4, Klf4, Sox2, L-Myc, Lin28; (8) Oct3/4, Klf4, Sox2, L-Myc, Lin28, SV40LT; (9) Oct3/4, Klf4, Sox2, L-Myc, Lin28, TERT, SV40LT; (10) Oct3/4, Klf4, Sox2, L-Myc, SV40LT; (11) Oct3/4, Klf4, Sox2, L-Myc (Esrrb is replaceable with Esrrg); (12) Oct3/4, Klf4, Sox2; (13) Oct3/4, Klf4, Sox2, TERT, SV40LT; (14) Oct3/4, Klf4, Sox2, TERT, HPV16 E6; (15) Oct3/4, Klf4, Sox2, TERT, HPV16 E7; (16) Oct3/4, Klf4, Sox2, TERT, HPV16 E6, HPV16 E7; (17) Oct3/4, Klf4, Sox2, TERT, Bmi1; (18) Oct3/4, Klf4, Sox2, Lin28 (19) Oct3/4, Klf4, Sox2, Lin28, SV40LT; (20) Oct3/4, Klf4, Sox2, Lin28, TERT, SV40LT; (21) Oct3/4, Klf4, Sox2, SV40LT; or (22) Oct3/4, Esrrb, Sox2 (Esrrb is replaceable with Esrrg). In one non-limiting example, Oct3/4, Klf4, Sox2, and c-Myc are utilized. In other embodiments, Oct4, Nanog, and Sox2 are utilized, see for example, U.S. Pat. No. 7,682,828, which is incorporated herein by reference. These factors include, but are not limited to, Oct3/4, Klf4 and Sox2. In other examples, the factors include, but are not limited to Oct 3/4, Klf4 and Myc. In some non-limiting examples, Oct3/4, Klf4, c-Myc, and Sox2 are utilized. In other non-limiting examples, Oct3/4, Klf4, Sox2 and Sal 4 are utilized.

Mouse and human cDNA sequences of these nuclear reprogramming substances are available with reference to the NCBI accession numbers mentioned in WO 2007/069666, which is incorporated herein by reference. Methods for introducing one or more reprogramming substances, or nucleic acids encoding these reprogramming substances, are known in the art, and disclosed for example, in published U.S. Patent Application No. 2012/0196360 and U.S. Pat. No. 8,071,369, which both are incorporated herein by reference.

After being cultured with nuclear reprogramming substances, the cell can, for example, be cultured under conditions suitable for culturing ES cells. In the case of mouse cells, the culture is carried out with the addition of Leukemia Inhibitory Factor (LIF) as a differentiation suppression factor to an ordinary medium. In the case of human cells, it is desirable that basic fibroblast growth factor (bFGF) be added in place of LIF.

In some embodiments, the cell is cultured in the co-presence of mouse embryonic fibroblasts treated with radiation or an antibiotic to terminate the cell division, as feeder cells. Mouse embryonic fibroblasts in common use as feeders include the STO cell line (ATCC CRL-1503) and the like; for induction of an iPSC, useful cells can be generated by stably integrating the neomycin resistance gene and the LIF gene in the STO cell (SNL76/7 STO cell; ECACC 07032801) (McMahon, A. P. & Bradley, A. Cell 62, 1073-1085, 1990) and the like can be used. Mitomycin C-treated MEFs are commercially available from Millipore. Gamma-irradiated MEFs are commercially available from Global Stem Generally, somatic cells are transduced with reprogramming factors in the absence of MEFs. In some embodiments, about 7 to eight days after transduction, the cells are re-seeded onto MEFs.

In some embodiments, the iPSC can be modified to express exogenous nucleic acids, such as to include a tyrosinase enhancer operably linked to a promoter and a nucleic acid sequence encoding a first marker. The tyrosinase gene is disclosed, for example, in GENBANK® Accession No. 22173, as available on Jan. 1, 2013. This sequence aligns to chromosome 7 of mouse strain C57BL/6 location 5286971-5291691 (invert orientation). A 4721 base pair sequence is sufficient for expression in RPE cells, see Murisier et al., Dev. Biol. 303: 838-847, 2007, which is incorporated herein by reference. This construct is expressed in retinal pigment epithelial cells. In some embodiments, the tyrosinase enhancer sequence comprises or consists of the following nucleic acid sequence:

(SEQ ID NO: 1)
TTCTTTTGCCCTTTCCTTTTCATAAACTGAACTTCATTTTAAGCAACAAG

TCTGTGTGAAACAGAAATGTCCTAATCTCTCTTTGACCAAATGTACCCAT

ATTCCCTTATGTTAACATGTATTTTTTACATTTAAGATTGTTAAAGTGGA

ACAGTTTTTTTTCTGCCATTATAGCACCTGTCTCTACTTTTCAAAGTATA

TGAATTATGATCTTTCTCATGTGGTTGTAAGCCCCATCTTTACAAGATTC

ACTTGATCTTTCATATTCAATTATTTATGGAACAAAATACCTGTCAATTC

TTAGAGTCTTTTCTACATAATTTATTTGTGAAAGAAAATGTTACTGGAAA

GTGACAAATTAGAGTCAAAATATAAAGACTGTGGCAGGTTATATACCTAT

AGTGTGATATGAAAGCTTTTGTAAGAAGAGGTAGTGGTACTAAACTGGAC

AAAATCCAGATAAAAGAGGCTTTGTGAAAATCAGGTAAAAATTTACTTAA

TATACAGCAAATACTAATAGTTGCTGTTTATAAAATACCATTTTCTGAAC

ATTGTTTTTGCACATATAACTAAAATGTTGAATATACCCAAGTATGAAAA

TTTAGTGTCATAGATATTAAGAACATTCTACCCTTTTCAGGAGAGTCATT

GACAGTGATTTAAGTGACTCTGCTTACACTGCTTGTCCTCTAACACTGAC

TCCATAATGATTGCAGCAAAAAATTAAAGCTCAAACGGTCTTGGGGATTA

CCTAGTTCAATGACTTTGATTTAACACAGTAAGTACTTGAAGTAGAAAGA

GGTACATTAACAAGCCAGGCAATGATGATATGGAGGGCAGTGTGATTAGA

GTACAGGATTCTACACTCATTCTGCATTATTGGTTCATATTTCTTCTGGG

GTAACTCACTTCCTTCCTTTTTCATATTTTCATTGCTCTAACTCTAGCCT

TGACTTTAGGAACATCTCTTCTTTTTCCACCTATAAGATAGAATTGTTTT

CTGCTGCAGGAGATTAAGATAGCTGGCATTCCTTTATGCTTATTTAGTCA

TTTCAAGCGATTAACTTCATCCTATCAGACTTTGAGATTAAGCTGCCAGT

AGTGACCTCATTAAAGTCCACACTTCTAATAAGCTTCTCTAAAAATTGTT

GAGAAGGCATTCTTGAGTTGGTACAGGGAAAGAATTGTGGACTCAGAAGC

AAACATAGCAAAGCTCATTTGTTCCAGTCTATGGTTTACAGGTCAAGTGA

TTTGGGACCAATTGCCAAAATACATTGGTGAGGAAAGGCATTAATATCAA

CTATGCCAAGTTACTATGCTTATTAAACTCAACCATGATACAGAGTTATA

TAATGTTATAATGTATTCATTGAATGTTTTATAAGAAACCAATTGTTTAT

TTGTTATTTAACTCTGCAAAACTACAGAAAGGGGAAATGGTTATTTAAGT

GGGTAATAAGTTTTAAGTATTTATCGTTCATAATAATTAACAGAGATGTT

ACAAAAATGTGACTGATTTTACTTGAAATGTTGCCATTTTAGTAAATGTG

GTGCCAAAGCAAGCATGAAATGTTGCCATTTTAAAGACATTTATTTTCTA

ATGCTATAATATATTCATTACATATTATTAAAATAATTAATGTAAAAATA

CCCAAAATGTGAAAATAACACGTAAGTCCTATTTTATGATTTTCCATATC

AAATTCAGAAACTAATACTCAGATCTTATTGTTTAAATAGTATTTAAAAT

TAAAGACACATAGTCAGGAATATATGCTAAATAAATTTTCCAAATTGAAT

AACTAACTTTCAGGGTTGCCTTACTTTCAACAAGAATATGCCTCTATTTG

ATTACTAATTGTAACTTTGTTCATAGACTACATAAGGTAATATTACAAAC

```
ATATTCATTATTTTGACACATACTTACTTAAATAATAAATAAACATTAGA
AAATATACTTACTATTTATATATAAAGAATTTTTTTGTTTCGAAGGAACT
TTAATAAATGAGATTATAAGGTTGTTGTTCAGGTACATTGAACATTTTTT
CAGGTTAATAAGGTGTCTAAAAATAAGTTTAGAAAGATCTAAGGTATTCT
TTTTTATTTGTTTTTGTCCTTTTTTATTTTTCTTTTTTGAACTGGGTTTC
TTCTTCAATTAGCCCTGGCTGGATGTCCTGGAACTAGCTCTATATGCCAT
GCTGTCTTCAAACTCATAGAGATCTGCCTACCTTTGCATCCCAAGTGCTG
GGATTAAAGGTATGAACCACCTCTTCCACCACTGCCAAGTAAGAATTCTT
ATTTTACATAAGTCATTATGAAGGAAGTTATGTGTTTACTGTAAACAAGA
TTAATGACTTGGTTTGCTGATTTTCTCTGAAAACATGAAATCTCTTCATA
TAGATCTTGCTTCTGGATAATAAAAGGCCCATGGAGAAATGTTCGTCTGT
CTAGTTTCATATTCATATTAATGATCCTGAATCAATTTTCCTCCATTGAG
ACTTGCATACTTAAGTATTAATGATTGCTGGAGTTCCATTCATAAGGATT
CTTTATGTATTACATGTTAAAATTTTTAAACCTACGACATTTTGGGATAT
AGTTTAGTAAAACATCTTAAATGGTGTAAGTGGTACCAATTAGTTTGAAG
GCAAAAACAATTGTTTAAGTGGATTAAGGTCTGTTCAATACTAGGGAACA
CCTGCTTGAAACACTTGACAATAGAAACTTAGCTAACTTACCCATGTCTG
GAAAGGTCATGGACTCTGAAGGAAAACTACTTTTACCATTTTCCTAAATC
AATATAGCTTTTAACTATTCTAAACACTGATCATTATACCCATAGACAGT
TTAGATCAACCCTTTCCAAAGAAGATTCTGTTTGTAGTAGATAAGGCTTA
ATACAAAGATCCTCAATTGGTCCAAATCCAGAGAATAGGTAAGCCTGTGG
TGTTTAGGTGCCCAACTTAGTCTACCAATAATACTACCTATGTACTTGAG
TACTAGTGAACAGGATACAGAAGGTGGTATCAGGAAGACTGTAAGAACCA
GAAAATATGAATACATACATGTGTATATTTATGCAAGAGTAACAATTAAA
GAAGTTTATTAATCTGAGTGTGTATGTGTTAATGTATAAAAATCTCAGAA
AAGTATTTAAAATTATTTTGCCTTTGGAAATAAAAATAACAAGTATTGTT
CAAGAAAAGATAATTCCAGGATACTAGCCAATTTTGCTCTTAACTTAGA
AATATAATTATATTTTTCTTCTCTTTGACTGGATAAATATGTACGAATG
TTCTTTGAATATTTGCAGCCAATTTGACTCCCTAAAAAATGGTATAGTTT
TAAATGTGTTTAACATATTGCTTTTGTGAAAGACATTTTTTTAGTATTAG
ATTCAATACTTTTTAACCATGTGGACATGGTTGGTGTTATTTTTGTTCTA
GAAAGGAACTGTTAAATTTCTGCTCCAACTTAGGTCATATAAGGGAAAAT
GAATCTGGTATTCTACAGAAAAATATAACTGTAACCATTTTGATGATTTT
TGTGTTAATTAGCACTGTTTGTCTGTTCATATCATTGAGGCACAGAAATG
GTATATTTATATAACACCTACCAAACAGCCTCATAAAGAAATAGATAGAT
TCTGGGGAATAAATGATCTCCATTTGATCCTCAGTTTTATTAAAATCCTT
CTGTTCCTGTGGCATGAATTCATCCAAACTGAGTAATGCTGGCAAGCAGG
AAGGGGATCAAGGTCATCCAAGGGATACTGACTTGGAAGGGTCTGGGCAT
GCAACCAAGTACTTCCAGGGTGAATTATTATTAAGAAAAAGAATGTTGAC
AAAAAAATATGTGAAAAGGACCTATAGCTAGCTATTCTCTTGGTGACCTG
GGTCTTGAGGAAGTTCTCTGGGAAGAGTCACTCAGCACATTTGGTCAAAT
GAATTCACCTATTCTGAAAACCAAATGAATATAGATTTCTGGACACCTCC
CAAGGATTCATGTGTAAGATGAAATGCAGATTGTTCACCAAAATTGTCCC
TGACTCCTATACTTAGACCATTTATTTTTCTGAAATCCCATAAACTGAGA
AGATGCTGTCTGATTAGAAGATACACAAGTCGTGGATAATAAGACAAAAG
AGCCCATGAACCTACAAAGCTCATTGCAAAGTGAACTTCTGTCTTGTAAC
AGAGAAAGCAGACAAACCAACAAAATCATTTATTTCAGTGAAAAGGAGGG
GCCAGAAATGGAAAGATTACATTTCCTAAGTCTCGTACTTGAAGACAGGT
TGGGTCCTCAGAACTAATTAAGTAGTAGAATGCACAATGTGCTTCAAGAA
AAAAGAAGCTATGAAAAACAGGTAGTCTATTTTATTTCAACCTAGCAACA
GTGAGAAAAGGATGAGCTAGCAAGGAGATGCAGATAGTGAAGTGTCCATT
GTGGATTTACTCTGGTTCTGACAGGTGGAATTGCTTCCATTCAAAACAAA
CAAAATAAACTTCTAACTCACAGTAATTCACAGTGTCACACTTTGTAACA
CAGGATGTCAAAGTTTCAGGACATACAGTCTCAACACATAGGTAATTAAT
TTAAGTGAGGTGATTTGAGTGAATTTAAATGCAATGGACTTGTAGATTTT
GTAAAAGAAGACACGTCTTTCAATACGCACACATATGGGAAAATGGTAT
GTAAATATGAAGTTAGCACTT
```

Longer fragments of the upstream region of the tyrosinase gene, that include this enhancer, can also be utilized, such as 5 kb, 6 Kb, 7 kb, 8 kb, etc.

Any promoter can be utilized, including, but not limited to Hsp70 1a promoter (GENBANK® Accession No. NT_039649.8. In some embodiment, the promoter includes, or consists of:

```
                                            (SEQ ID NO: 2)
CAGGAACATCCAAACTGAGCAGCCGGGGTCCCCCCCACCCCCACCCCGC
CCCTCCCGGCAACTTTGAGCCTGTGCTGGGACAGAGCCTCTAGTTCCTAA
ATTAGTCCATGAGGTCAGAGGCAGCACTGCCATTGTAACGCGATTGGAGA
GGATCACGTCACCGGACACGCCCCCAGGCATCTCCCTGGGTCTCCTAAAC
TTGGCGGGGAGAAGTTTTAGCCCTTAAGTTTTAGCCTTTAACCCCCATAT
TCAGAACTGTGCGAGTTGGCGAAACCCCACAAATCACAACAAACTGTACA
CAACACCGAGCTAGAGGTGATCTTCTTGTCCATTCCACACAGGCCTTAG
TAATGCGTCGCCATAGCAACAGTGTCACTAGTAGCACCAGCACTTCCCCA
CACCCTCCCCCTCAGGAATCCGTACTCTCCAGTGAACCCCAGAAACCTCT
GGAGAGTTCTGGACAAGGGCGGAACCCACAACTCCGATTACTCAAGGGAG
GCGGGGAAGCTCCACCAGACGCGAAACTGCTGGAAGATTCCTGGCCCCAA
GGCCTCCTCCGGCTCGCTGATTGGCCCAGCGGAGAGTGGGCGGGGCCGGT
GAAGACTCCTTAAAGGCGCAGGGCGGCGAGCAGGTCACCAGACGCTGACA
GCTACTCAGAACCAAATCTGGTTCCATCCAGAGACAAGCGAAAGACAAGA
GAAGCAGAGCGAGCGGCGCGTTCCCGATCCTCGGCCAGGACCAGCCTTCC
CCAGAGCATCCCTGCCGCGGAGCGCAACCTTCCCAGGAGCATCCCTGCCG
CGGAGCGCAACTTTCCCCGGAGCATCCACGGCCGCGGAGCGCAGCCTTTC
CAGAAGCAGAAGCGCGGCGCCAATGGCTCGCGAATGAATCCCGTCGGTTT
```

-continued

TAACAAACGGTCGGTGAACCTGGGGAAAAACCTGCGGTTAACCCAACTTA

AATTCGCCCTCTGGGCAAGAC

Small deletions, additions, and substitutions can be made without affecting the activity of SEQ ID NO: 1 and/or SEQ ID NO: 2, such as at most 10, 9, 8, 7, 6, 5, 4, 3, 2, or 1 base.

Other enhancers can be utilized. Other RPE-specific enhancers include D-MITF, DCT, TYRP1, RPE65, VMD2, MERTK, MYRIP, RAB27A, Suitable promoters include, but are not limited to, any promoter expressed in retinal pigment epithelial cells including the tyrosinase promoter. The construct can also include other elements, such as a ribosome binding site for translational initiation (internal ribosomal binding sequences), and a transcription/translation terminator.

Generally, it is advantageous to transfect cells with the construct. Suitable vectors for stable transfection include, but are not limited to retroviral vectors, lentiviral vectors and Sendai virus.

Plasmids have been designed with a number of goals in mind, such as achieving regulated high copy number and avoiding potential causes of plasmid instability in bacteria, and providing means for plasmid selection that are compatible with use in mammalian cells, including human cells. Particular attention has been paid to the dual requirements of plasmids for use in human cells. First, they are suitable for maintenance and fermentation in E. coli, so that large amounts of DNA can be produced and purified. Second, they are safe and suitable for use in human patients and animals. The first requirement calls for high copy number plasmids that can be selected for and stably maintained relatively easily during bacterial fermentation. The second requirement calls for attention to elements such as selectable markers and other coding sequences. In some embodiments plasmids that encode a marker are composed of: (1) a high copy number replication origin, (2) a selectable marker, such as, but not limited to, the neo gene for antibiotic selection with kanamycin, (3) transcription termination sequences, including the tyrosinase enhancer and (4) a multicloning site for incorporation of various nucleic acid cassettes; and (5) a nucleic acid sequence encoding a marker operably linked to the tyrosinase promoter. There are numerous plasmid vectors that are known in the art for inducing a nucleic acid encoding a protein. These include, but are not limited to, the vectors disclosed in U.S. Pat. Nos. 6,103,470; 7,598,364; 7,989,425; and 6,416,998, which are incorporated herein by reference.

Viral vectors can be utilized for the introduction of nucleic acids, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nacl. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217,879), alphaviruses (S. Schlesinger, 1993, Trends Biotechnol. 11:18-22; I. Frolov et al., 1996, Proc. Natl. Acad. Sci. USA 93:11371-11377), human herpesvirus vectors (HHV) such as HHV-6 and HHV-7, and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (Autographa californica multinuclear polyhedrosis virus; AcMNPV) vectors can be used. Vectors can be obtained from commercial sources (such as PharMingen, San Diego, Calif.; Protein Sciences Corp., Meriden, Conn.; Stratagene, La Jolla, Calif.). Suitable vectors are disclosed, for example, in U.S. Published Patent Application No. 2010/0247486, which is incorporated herein by reference. In specific non-limiting examples, the vectors are retrovirus vectors (for example, lentivirus vectors), measles virus vectors, alphavirus vectors, baculovirus vectors, Sindbis virus vectors, adenovirus and poliovirus vectors.

Methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or functional fragment thereof, and a second foreign DNA molecule encoding a selectable phenotype, such as the herpes simplex thymidine kinase gene.

A viral gene delivery system can be an RNA-based or DNA-based viral vector. An episomal gene delivery system can be a plasmid, an Epstein-Barr virus (EBV)-based episomal vector, a yeast-based vector, an adenovirus-based vector, a simian virus 40 (SV40)-based episomal vector, a bovine papilloma virus (BPV)-based vector, or a lentiviral vector.

Markers include, but are not limited to, fluorescence proteins (for example, green fluorescent protein or red fluorescent protein), enzymes (for example, horse radish peroxidase or alkaline phosphatase or firefly/renilla luciferase or nanoluc), or other proteins. A marker may be a protein (including secreted, cell surface, or internal proteins; either synthesized or taken up by the cell); a nucleic acid (such as an mRNA, or enzymatically active nucleic acid molecule) or a polysaccharide. Included are determinants of any such cell components that are detectable by antibody, lectin, probe or nucleic acid amplification reaction that are specific for the marker of the cell type of interest. The markers can also be identified by a biochemical or enzyme assay or biological response that depends on the function of the gene product. Nucleic acid sequences encoding these markers can be operably linked to the tyrosinase enhancer. In addition, other genes can be included, such as genes that may influence stem cell to RPE differentiation, or RPE function, or physiology, or pathology. Thus, in some embodiments, a nucleic acid is included that encodes one or more of MITF, PAX6, TFEC, OTX2, LHX2, VMD2, CFTR, RPE65, MFRP, CTRP5, CFH, C3, C2B, APOE, APOB, mTOR, FOXO, AMPK, SIRT1-6, HTRP1, ABCA4, TIMP3, VEGFA, CFI, TLR3, TLR4, APP, CD46, BACE1, ELOLV4, ADAM10, CD55, CD59, and ARMS2.

The iPSCs, optionally including the tyrosinase promoter operably linked to a marker, are cultured under conditions such that embryoid bodies (EBs) are formed. Methods for the production of EBs are known in the art. In some embodiments, EBs are produced in suspension culture: undifferentiated iPSCs are harvested by brief collagenase digestion, dissociated into clusters, and cultured in non-adherent cell culture plates EBs are cultured for about 36 to about 72 hours, such as for about 48 hours and then plated. In some examples, the medium is not changed during this period.

Without being bound by theory, EBs are formed by the homophilic binding of the Ca2+ dependent adhesion molecule E-cadherin, which is highly expressed on undifferentiated stem cells. When cultured as single cells under specific conditions, iPSCs spontaneously aggregate to form EBs. Such spontaneous formation is often accomplished in bulk suspension cultures whereby the dish is coated with non-adhesive materials, such as agar or hydrophilic polymers, to promote the preferential adhesion between single cells, rather than to the culture substrate. To avoid dissociation into single cells, EBs can be formed from iPSCs by manual separation of adherent colonies (or regions of colonies) and subsequently cultured in suspension. Formation of EBs in suspension is amenable to the formation of large quantities of EBs, but provides little control over the size of the resulting aggregates, often leading to large, irregularly shaped EBs. As an alternative, the hydrodynamic forces imparted in mixed culture platforms increase the homogeneity of EB sizes when iPSCs are inoculated within bulk suspensions.

In some embodiments, EBs are selected that include about 150 to about 600 cells, such as about 200 to about 500 cells, such as about 200 to about 500 cells. In additional embodiments, the EBs include less than about 500 cells, such as less than about 450 cells or less than about 400 cells. In further embodiments, the EBs include less than 500 cells, such as less than 450 cells or less than 400 cells. In other embodiments, about 200 to about 400 EBs are plated in each well of a standard 6-well tissue culture plate, such as about 100 to about 200 EBs, for example about 100 to about 150 EBs. In this context, "about" means within 20 cells or embryoid bodies.

The EBs are then cultured a first medium comprising two Wnt pathway inhibitors and a Nodal pathway inhibitor. The first medium, that includes the Wnt pathway inhibitors and the Nodal pathway inhibitor, can be a retinal cell inducing medium. An exemplary non-limiting medium is Dulbecco's Modified Eagle's Medium (DMEM) and F12 at a ratio of about 1:1 in the absence of serum. Other tissue culture media can also be used, such as Knock out DMEM. In some embodiments, the cells are cultured for about 36 to about 50 hours, such as for about 48 hours. Additional exemplary media are disclosed in the examples section.

The Wnt pathway inhibitors can be, for example, N-(2-aminoethyl)-5-chloroisoquinoline-8-sulfonamide (CK1-7), 3,5,7,8-Tetrahydro-2-[4-(trifluoromethyl)phenyl]-4H-thiopyrano[4,3-d]pyrimidin-4-one (XAV939), Secreted frizzled-related protein (SFRP) 1, sFRP1 (GENBANK® Accession No. AF001900.1), sFRP2 (GENBANK® Accession No. NM_003013.2), sFRP3 (GENBANK® Accession No. U91903.1), sFRP4 (GENBANK® Accession No. NM_003014.3), and sFRP5 (GENBANK® Accession No. NM_003015.3,), SFRP-3, SFRP-4 or SFRP-5. These GENBANK® sequences are incorporated herein by reference as available on Jan. 1, 2013. The SFRP can be included at a concentration of about 5 ng/ml to 100 ng/ml, such as a out 10 ng/ml to about 90 mg/ml, such as about 20 ng/ml to about 80 ng/ml. In some embodiments, the first medium includes about 3 to about 10 mM of CK1-7 dichloride (N-(2-Aminoethyl)-5-chloroisoquinoline-8-sulphonamide dihydrochloride), for example about 3.5 to about 9 mM of CK1-7, or about 4 to about 8 mM of CK1-7.

The Nodal pathway inhibitor can be, for example, 4-(5-Benzol[1,3]dioxol-5-yl-4-pyridine-2-yl-1H-imidazol-2-yl)-benzamide hydrate, 4-[4-(1,3-Benzodioxol-5-yl)-5-(2-pyridinyl)-1H-imidazol-2-yl]-benzamide hydrate, 4-[4-(3,4-Methylenedioxyphenyl)-5-(2-pyridyl)-1H-imidazol-2-yl]-benzamide hydrate (SB-431542), left-right determination factor (Lefty) or 2-(5-Benzo[1,3]dioxol-5-yl-2-tert-butyl-3H-imidazol-4-yl)-6-methylpyridine hydrochloride hydrate (SB-505124). In some embodiments, the first medium includes about 3 to about 10 mM of SB43152, for example about 3.5 to about 9 mM of SB43152, or about 4 to about 8 mM of SB43152.

The cells are cultured in the first medium for about 36 to 72 hours, such as for about 48 hours. Following culture in the first media, such as for about 36 to about 72 hours, such as for about 48 hours, the EBs are plated on a tissue culture substrate in a second medium. In some embodiments, the tissue culture substrate is coated with MATRIGEL®. The second medium does not include exogenous beta fibroblast growth fact (bFGF). The second media also includes a basic fibroblast growth factor (bFGF) inhibitor, two Wnt pathway inhibitors, and a Nodal pathway inhibitor. Exemplary media are disclosed in the examples section.

Suitable Wnt pathway inhibitors and Nodal inhibitors are disclosed above. Suitable bFGF inhibitors include, but are not limited to, N-[(2R)-2,3-Dihydroxypropoxy]-3,4-difluoro-2-[(2-fluoro-4-iodophenyl)amino]-benzamide (PD0325901), N-[2-[[4-(Diethylamino)butyl]amino-6-(3,5-dimethoxyphenyl)pyrido[2,3-d]pyrimidin-7-yl]-N'-(1,1-dimethylethyl)urea (PD173074), 2-(2-Amino-3-methoxyphenyl)-4H-1-benzopyran-4-one (PD 98059), 1-tert-Butyl-3-[6-(2,6-dichlorophenyl)-2-[[4-(diethylamino)butyl]amino] pyrido[2,3-d]pyrimidin-7-yl]urea (PD161570), or 6-(2,6-Dichlorophenyl)-2-[[4-[2-(diethylamino)ethoxy]phenyl] amino]-8-methyl-pyrido[2,3-d]pyrimidin-7(8H)-one dihydrochloride hydrate (PD166285). In some embodiments, the second medium comprises about 0.2 to about 2.5 mM of a PD0325901, such as about 0.5 to about 2 mM of PD0325901, such as about 1 to about 2 mM of PD0325901. In one specific non-limiting example, the second medium includes about 3.5 to about 9 mM of CK1-7 and about 3.5 to about 9 mM of SB431542, such as about 5 mM of SB431542.

The second medium can include about 20 to about 90 ng of Noggin, such as about 30 to about 90 ng of Noggin, such as about 40 to about 80 ng of Noggin, such as about 50 ng/ml of Noggin.

The second medium can also include about 0.5% to about 3.5% such as about 1 to about 3%, such as about 2 to about 3%, KNOCKOUT™ serum replacement to form. KNOCKOUT™ serum replacement is disclosed, for example, in published U.S. Patent Application No. 2002/076747 and PCT Publication No. 98/830679, which are both incorporated herein by reference, and is available commercially from LIFE TECHNOLOGIES™ to produced differentiating retinal pigment epithelial cells.

Inhibitors of basic fibroblast growth factor (bFGF, also known as FGF-2) include, but are not limited to, N-[(2R)-2,3-Dihydroxypropoxy]-3,4-difluoro-2-[(2-fluoro-4-iodophenyl)amino]-benzamide (PD0325901), N-[2-[[4-(Diethylamino)butyl]amino-6-(3,5-dimethoxyphenyl)pyrido[2,3- d]pyrimidin-7-yl]-N'-(1,1-dimethylethyl)urea (PD173074), 2-(2-Amino-3-methoxyphenyl)-4H-1-benzopyran-4-one (PD 98059), 1-tert-Butyl-3-[6-(2,6-dichlorophenyl)-2-[[4-(diethylamino)butyl]amino]pyrido[2,3-d]pyrimidin-7-yl] urea (PD161570), or 6-(2,6-Dichlorophenyl)-2-[[4-[2-(diethylamino)ethyl]phenyl]amino]-8-methyl-pyrido[2,3-d]pyrimidin-7(8H)-one dihydrochloride hydrate (PD166285). In some embodiments, the second medium includes about 0.5 to about 2 mM of PD0325901, such as about 1 to about 2 mM of PD0325901, such as about 1.5 to about 2 mM of PD0325901, such as about 1 mM of PD0325901.

In some embodiments, the cells are cultured in the second medium for about 18 to about 24 days, such as for about 20 to about 22 days, such as for about 18, 19, 20, 21, 22, 23 or 24 days. In other embodiments, the cells are cultured in the second medium for a period of about 14 days to about four weeks, such about 14 days to about three weeks, such for about two weeks, for about 14, about 15, about 16, about 17, about 18, about 19, about 20, or about 21 days. Specific non-limiting examples are for 14 days to three weeks, one week to two weeks, one week to 10 days, one week to three weeks, or one week, two weeks or three weeks. In this context, "about" indicates within one day of the listed time.

Specific non-limiting examples of exemplary concentrations of PD325901, Noggin and/or DKK1 are shown in FIGS. 8-10. In some embodiments, the methods provide an increase in Pax6 expression in cells that are culture in the second medium for about one to about two weeks, as compared to the initial population of cells. In certain embodiments, the cells are culture in the absence of, and in the presence of a bFGF inhibitor, and in the presence of Noggin. Non-limiting examples include about 10 mM PD0325901 and about 50 to about 100 ng/ml of Noggin. Additional examples are presented in FIG. 8. Optionally, the medium can include DKK1 at about 50 to 100 ng/ml, such as about 75 m 80, 85, 90, 95 or 100 ng/ml of DKK1. In some embodiments, Pax6 expression is increased at least 150, 160, 170, 180, 190, 200, 210, 220, 230, 240 times following culture for one week, as compared to the starting cells. In other embodiments, Pax6 expression is increased at least 400, 450, 500, or 600 times following culture for one to two weeks, as compared to expression in the starting cells. In yet other embodiments, Pax6 expression is increased at least 500, 600, 700, 800, or 900 times following culture for one to three weeks, as compared to expression in the cells prior to culture in the starting cells, such as embryoid bodies at day zero of culture.

In yet other embodiments, Microphthalmia associated transcription factor (MITF, GENBANK Accession No. NG_011631.1, as available Jan. 1, 2013, incorporated herein by reference) expression is increased at least 4, 5, 6, 7, 8, 9 or 10 times following culture for one week, as compared to expression in the cells prior to culture in the second medium. In other embodiments, MITF expression is increased at least 3, 4, 5, 6, 7, 8, 9, or 10 times following culture for one to two weeks, as compared to expression in the cells prior to culture in the second medium. In yet other embodiments, MITF expression is increased at least 6, 7, 8, 9, 10, 20, 30, 40, 45, or 50 times following culture for one to three weeks, as compared to expression in the starting cells, such as embryoid bodies at day 0 of culture.

In some embodiments, expression from a tyrosinase enhancer promoter is increased. Thus, in some embodiments, expression of a nucleic acid encoding a marker operably linked to the tyrosinase enhancer is increased. For example, the expression of a marker can be increased by at least 30%, 40%, 50%, 60%, 70%, 80%, 90% or 100%.

The resultant differentiating RPE cells are then transferred to a third medium. In some embodiments, the third medium includes about 50 to about 300 ng/ml of ACTIVIN A, such as about 100 to about 200 ng/ml of ACTIVIN A, such as about 150 to about 200 ng/ml of ACTIVIN A, such as about 150 ng/ml of Activin A. In additional embodiments, the third medium comprises about 75 to 150 ng/ml of Wnt3a, such as about 100 to 150 ng/ml of Wnt 3a, such as about 110 to 140 ng/ml of Wnt 3a, such as about 100 ng/ml. In this context, about means within 2 ng/ml.

In some embodiments, the cells are cultured in the third medium for about 18 to about 24 days, such as for about 20 to about 22 days, such as for about 18, 19, 20, 21, 22, 23 or 24 days. In some embodiments, the cells are cultured in the third medium for a period of about 14 days to about four weeks, such about 14 days to about three weeks, such for about two weeks, for about 14, about 15, about 16, about 17, about 18, about 19, about 20, or about 21 days. Specific non-limiting examples are for 14 days to three weeks, one week to two weeks, one week to 10 days, one week to three weeks, or one week, two weeks or three weeks. In this context, "about" indicates within one day of the listed time.

After culture in the third medium the cells are cultured in a fourth medium that includes about 3 to about 6 percent serum, such as about 5 percent serum. In some embodiments, the serum is fetal calf serum. In other embodiments, the serum is human serum. The RPE medium includes a canonical WNT inhibitor, a non-canonical WNT inducer, and inhibitors of the Sonic and FGF pathway to produce differentiated RPE cells.

This medium also includes a canonical WNT inhibitor, a non-canonical WNT inducer, and inhibitors of the Sonic and FGF pathways. In additional embodiments, the canonical WNT inhibitor is Dickkopf-related protein. This, in some examples, the medium includes about 50 to about 200 ng/ml of Dickkopf-related protein 1 (DKK1), such as about 50 to about 100 ng/ml of DKK1, such as about 40, 45, 50, 55, 60, 65, 70, 75, 80, 85, 90 or 100 ng/ml of DKK1. In some embodiments, the non-canonical WNT induce is Want 5a. In one example, the fourth medium comprises about 50 to about 200 ng/ml of the non-cannonical WNT inducer, such as WNT5a, such as about 50 to about 100 ng/ml, such as about 40, 45, 50, 55, 60, 65, 70, 75, 80, 85, 90 or 100 ng/ml. In another example, the fourth medium comprises about 5 to about 20 μM Cycolopamine, such as about 5-10 μM Cyclopamine, such as about 5, 6, 7, 8, 9, or 10 μM Cyclopamine. In yet another embodiments, the fourth medium comprises about 5 to about 20 μM SU5402, such as about 5-10 μM SU5402, such as about 5, 6, 7, 8, 9, or 10 μM SU5402.

The cells can be culture in the fourth medium for about 10 to about 20 days, such as for about 10, 11, 12, 13, 14, 15, 16, 17, 18 or 19 days, such as for about two weeks, or for about 12 to about 16 days.

In some embodiments, the cells are also cultured in the fourth medium comprising 3 to about 6% serum, such as about 3% to about 6% human serum or fetal calf serum, such as about 3%, 4%, 5% or 6% fetal calf serum.

Retinal pigment epithelial cells produced by the methods disclosed herein are cultured in the fourth medium containing aphidicolin for 6-8 weeks. In some embodiments, the retinal pigment epithelia cells are cultured, for example, in a tissue culture medium including aphidicolin at a concentration of about 3 μM to about 10 μM. In additional embodiments, the retinal pigment epithelial cells are cultured in a tissue culture medium including about 3 μM, about 4 μM, about 5 μM, about 6 μM, about 7 μM, about 8 μM, about 9 μM or about 10 μM aphidicolin. The retinal pigment epithelial cells can be cultured for about 4 to about 6 weeks in the tissue culture medium including aphidicolin, such as for about 4 weeks, about 5 weeks, or about 6 weeks. In some embodiments, the use of aphidicolin is sufficient to increase polarization of the retinal pigment epithelial cells.

The methods disclosed herein efficiently produce RPE cells. Thus, using the methods disclosed herein, at least about 85%, 90%, 91%, 92%, 93%, 94%, 95%, 96%, 97%, 98% or 99% of the resultant cells are RPE cells. In some embodiments, a construct including the tyrosinase enhancer operably linked to a marker, such as a fluorescent protein, is included in the iPSCs. Using the methods disclosed herein, at least about 85%, 90%, 91%, 92%, 93%, 94%, 95%, 96%, 97%, 98% or 99% of the cells express this marker.

Following culture in the fourth medium the RPE cells can be maintained in culture. In some embodiments, the RPE cells are maintained in RPE medium (see above) including comprising about 3 to about 6% serum, such as about 3%, about 4%, about 5% or about 6% serum. The serum can be fetal serum. In some non-limiting examples, the serum is fetal calf serum. In other embodiment, the serum is human serum. The RPE cells can be maintained in RPE medium, comprising about 3% to about 6% serum, such as about 5% serum, for example about 5% fetal serum, for about six to about eight weeks. In some embodiments, the RPE cells are grown in transwells, such as in a 6-well, 12-well, 24-well, or 10 cm plate. The retinal pigment epithelial cells can be maintained in retinal pigment epithelial cell (RPE) medium comprising about 5% fetal serum for about four to about ten weeks, such as for about six to about eight weeks, such as for six, seven or eight weeks.

The method can also include confirming that the resultant cells are RPE cells. Method for this confirmation are disclosed below.

Pharmaceutical Compositions and Use of RPE Cells

Disclosed herein are compositions, such as pharmaceutical compositions, including human RPE cells. In certain embodiments, the preparation is a preparation of iPSC-derived RPE cells, such as, but not limited to RPE cells derived from an iPSC produced from a fetal RPE cell, such as a human fetal RPE cell. In certain embodiments, these compositions are substantially purified (with respect to non-RPE cells) preparations comprising differentiated RPE cells produced by the methods disclosed herein. These substantially purified populations are compositions that include at least 90%, 91%, 92%, 93%, 94%, 95%, 96%, 97%, 98%, 99%, or even greater than 99% RPE cells. Thus, the compositions contains less than 10%, 9%, 8%, 7%, 6%, 5%, 4%, 3%, 2%, or less than 1% of cells that are not RPE cells. In certain embodiments, the compositions include at least about $1 \times 10^3$ RPE cells, about $1 \times 10^4$ RPE cells, about $1 \times 10^5$ RPE cells, about $1 \times 10^6$ RPE cells, about $1 \times 10^7$ RPE cells, about $1 \times 10^8$ RPE cells, or about $1 \times 10^9$ RPE cells.

In certain embodiments, the cells express one or more of the genes listed in Table 1 below.

TABLE 1

| Gene Symbo | Refseq # |
| --- | --- |
| SLC9A3R1 | NM_004252 |
| SLC6A6 | NM_003043 |
| SLC12A2 | NM_001046 |
| SNAI3 | NM_178310 |
| SNAI2 | NM_003068 |
| SNAI1 | NM_005985 |
| CDKN1B | NM_004064 |
| PTK2 | NM_005607 |
| UTP3 | NM_020368 |
| USO1 | NM_003715 |
| BHLHE41 | NM_030762 |
| HSPA13 | NM_006948 |
| AKIRIN1 | NM_024595 |
| NCRNA00153 | NM_018474 |
| FAM13A | NM_014883 |
| FRMD7 | NM_194277 |
| HLA-DRB4 | NM_021983 |
| LYZ | NM_000239 |
| RGS1 | NM_002922 |
| IMPG1 | NM_001563 |
| PDE6H | NM_006205 |
| UNC119 | NM_005148 |
| LEPR | NM_002303 |
| LGI1 | NM_005097 |
| HMGCS2 | NM_005518 |
| RBP4 | NM_006744 |
| OGN | NM_014057 |
| RARRES1 | NM_002888 |
| RHO | NM_000539 |
| CHN1 | NM_001822 |
| CFH | NM_000186 |
| CHI3L1 | NM_001276 |
| MAK | NM_005906 |
| DDC | NM_000790 |
| S100A8 | NM_002964 |
| BMP5 | NM_021073 |
| ITGBL1 | NM_004791 |
| PLA2G2A | NM_000300 |
| RNASE6 | NM_005615 |
| HLA-DRA | NM_019111 |
| MS4A4A | NM_024021 |
| KLF9 | NM_001206 |
| PPEF2 | NM_006239 |
| LMOD1 | NM_012134 |
| HLA-DQB1 | NM_002123 |
| IL1R2 | NM_004633 |
| ASPH | NM_004318 |
| MYO6 | NM_004999 |
| GPX3 | NM_002084 |
| IL33 | NM_033439 |
| GAP43 | NM_002045 |
| ACSL3 | NM_004457 |
| FHIT | NM_002012 |
| FBLN1 | NM_001996 |
| IL6ST | NM_002184 |
| CPEB3 | NM_014912 |
| SPP1 | NM_000582 |
| MNDA | NM_002432 |
| PSD3 | NM_015310 |
| SLC16A3 | NM_004207 |
| LRAT | NM_004744 |
| TMEM176B | NM_014020 |
| IGHA1 | XM_370781 |
| HEG1 | NM_020733 |
| KCNV2 | NM_133497 |
| SERPINA3 | NM_001085 |
| PDE6G | NM_002602 |
| PDE6D | NM_002601 |
| CD163 | NM_004244 |
| RBP3 | NM_002900 |
| CFD | NM_001928 |
| CXCR4 | NM_003467 |
| EHHADH | NM_001966 |
| NPL | NM_030769 |
| NR1D1 | NM_021724 |
| RORB | NM_006914 |
| MREG | NM_018000 |
| VNN2 | NM_004665 |
| IGJ | NM_144646 |
| CPE | NM_001873 |
| RAPGEF4 | NM_007023 |
| MAFB | NM_005461 |

TABLE 1-continued

| Gene Symbol | Refseq # |
|---|---|
| RCVRN | NM_002903 |
| EDNRB | NM_000115 |
| S100A9 | NM_002965 |
| TOB1 | NM_005749 |
| SUSD5 | NM_015551 |
| SLC25A24 | NM_013386 |
| SAG | NM_000541 |
| CDKN1C | NM_000076 |
| ACSL1 | NM_001995 |
| OPN1LW | NM_020061 |
| TOX3 | NM_00108043 |
| MEGF9 | NM_00108049 |
| LYVE1 | NM_006691 |
| TMEM127 | NM_017849 |
| FXYD3 | NM_005971 |
| CFI | NM_000204 |
| TNPO1 | NM_002270 |
| C4orf31 | NM_024574 |
| HPGD | NM_000860 |
| CLUL1 | NM_199167 |
| EZH1 | NM_001991 |
| TOB2 | NM_016272 |
| TRPC1 | NM_003304 |
| KCND2 | NM_012281 |
| TRPC4 | NM_016179 |
| SOX11 | NM_003108 |
| IGF2BP3 | NM_006547 |
| RELN | NM_005045 |
| HSD17B2 | NM_002153 |
| FGFR3 | NM_000142 |
| ASPM | NM_018136 |
| CYTL1 | NM_018659 |
| ELN | NM_000501 |
| BARD1 | NM_000465 |
| TRO | NM_016157 |
| PTH | NM_000315 |
| SERPINH1 | NM_001235 |
| TMEFF1 | NM_003692 |
| COL9A3 | NM_001853 |
| C5orf13 | NM_004772 |
| PSPH | NM_004577 |
| NID2 | NM_007361 |
| COL11A1 | NM_080629 |
| LIPG | NM_006033 |
| APC | NM_000038 |
| ADAMTSL3 | NM_207517 |
| TSPAN12 | NM_012338 |
| PTPRD | NM_002839 |
| HOMER1 | NM_004272 |
| MAB21L2 | NM_006439 |
| TYR | NM_000372 |
| TNNC1 | NM_003280 |
| CLGN | NM_004362 |
| PRMT7 | NM_019023 |
| PTPLA | NM_014241 |
| MFAP2 | NM_002403 |
| GLRB | NM_000824 |
| TRPM3 | NM_020952 |
| PXDN | NM_012293 |
| CYP27A1 | NM_000784 |
| KDELC1 | NM_024089 |
| PDGFC | NM_016205 |
| RASGRP3 | NM_170672 |
| NUP93 | NM_014669 |
| SMC6 | NM_024624 |
| C11orf9 | NM_013279 |
| WFDC1 | NM_021197 |
| CXorf57 | NM_018015 |
| HBG1 | NM_000559 |
| PIK3C3 | NM_002647 |
| CTSL2 | NM_001333 |
| NOTCH2NL | NM_203458 |
| KCNAB1 | NM_003471 |
| SLC5A3 | NM_006933 |
| ABHD2 | NM_007011 |
| SGMS1 | NM_147156 |
| GOLGA1 | NM_002077 |
| SFRP1 | NM_003012 |
| TFEC | NM_012252 |
| LRRC1 | NM_018214 |
| CAPN3 | NM_173090 |
| FLRT2 | NM_013231 |
| PNPLA3 | NM_025225 |
| TRIM36 | NM_018700 |
| NBEA | NM_015678 |
| DAAM1 | NM_014992 |
| PLCE1 | NM_016341 |
| PPFIBP2 | NM_003621 |
| MITF | NM_000248 |
| NELL2 | NM_006159 |
| SC4MOL | NM_006745 |
| PLAG1 | NM_002655 |
| IGF2BP2 | NM_006548 |
| SIX3 | NM_005413 |
| CDH3 | NM_001793 |
| DZIP1 | NM_198968 |
| FOXD1 | NM_004472 |
| WWTR1 | NM_015472 |
| GJA1 | NM_000165 |
| PLCB4 | NM_000933 |
| SEMA3C | NM_006379 |
| PKNOX2 | NM_022062 |
| COL8A2 | NM_005202 |
| WWC2 | NM_024949 |
| DMXL1 | NM_005509 |
| GAS1 | NM_002048 |
| GPR143 | NM_000273 |
| DCT | NM_001922 |
| NAV3 | NM_014903 |
| SMAD6 | NM_005585 |
| CDH1 | NM_004360 |
| ASAH1 | NM_004315 |
| RAB38 | NM_022337 |
| PAK1IP1 | NM_017906 |
| NOL8 | NM_017948 |
| CDO1 | NM_001801 |
| PHACTR2 | NM_014721 |
| SILV | NM_006928 |
| TTLL4 | NM_014640 |
| MANEA | NM_024641 |
| PDPN | NM_006474 |
| FADS1 | NM_013402 |
| HSP90B1 | NM_003299 |
| PTPRG | NM_002841 |
| VEGFA | NM_003376 |
| EFHC1 | NM_018100 |
| SULF1 | NM_015170 |
| GPNMB | NM_002510 |
| SDC2 | NM_002998 |
| CSPG5 | NM_006574 |
| MED8 | NM_201542 |
| GULP1 | NM_016315 |
| MAB21L1 | NM_005584 |
| SCAMP1 | NM_004866 |
| SLC4A2 | NM_003040 |
| USP34 | NM_014709 |
| FGFR2 | NM_000141 |
| SLC6A15 | NM_182767 |
| LOXL1 | NM_005576 |
| SORBS2 | NM_003603 |
| LIN7C | NM_018362 |
| GEM | NM_005261 |
| GPM6B | NM_005278 |
| APLP1 | NM_005166 |
| PITPNA | NM_006224 |
| ITGAV | NM_002210 |
| RBP1 | NM_002899 |
| STAM2 | NM_005843 |
| TRPM1 | NM_002420 |
| NRIP1 | NM_003489 |
| ENPP2 | NM_006209 |
| RRAGD | NM_021244 |
| CHRNA3 | NM_000743 |
| SLC6A20 | NM_020208 |
| SERPINF1 | NM_002615 |
| IFT74 | NM_025103 |

TABLE 1-continued

| Gene Symbol | Refseq # |
|---|---|
| LHX2 | NM_004789 |
| ALDH1A3 | NM_000693 |
| MAP9 | NM_00103958 |
| SFRP5 | NM_003015 |
| SGK3 | NM_013257 |
| CLCN4 | NM_001830 |
| MFAP3L | NM_00100955 |
| BEST1 | NM_004183 |
| SOSTDC1 | NM_015464 |
| BMP4 | NM_130851 |
| MET | NM_000245 |
| SLC16A4 | NM_004696 |
| DUSP4 | NM_057158 |
| FRZB | NM_001463 |
| MYRIP | NM_015460 |
| TFPI2 | NM_006528 |
| TTR | NM_000371 |
| TYRP1 | NM_000550 |
| RPE65 | NM_000329 |
| LIMCH1 | NM_014988 |
| SPAST | NM_199436 |
| OSTM1 | NM_014028 |
| CYP20A1 | NM_177538 |
| ATF1 | NM_005171 |
| SIL1 | NM_022464 |
| MPDZ | NM_003829 |
| SEPT8 | NM_00109881 |
| DCUN1D4 | NM_015115 |
| PDZD8 | NM_173791 |
| LAMP2 | NM_002294 |
| DEGS1 | NM_003676 |
| DHPS | NM_001930 |
| MBNL2 | NM_144778 |
| DIXDC1 | NM_033425 |
| NUDT4 | NM_199040 |
| PTGDS | NM_000954 |
| CALU | NM_001219 |
| RBM34 | NM_015014 |
| NEDD4L | NM_015277 |
| RHOBTB3 | NM_014899 |
| NDC80 | NM_006101 |
| ARMC9 | NM_025139 |
| PRNP | NM_183079 |
| AHR | NM_001621 |
| UBL3 | NM_007106 |
| ZNF19 | NM_006961 |
| RNF13 | NM_183384 |
| DAP3 | NM_004632 |
| CTBP2 | NM_022802 |
| KLHL24 | NM_017644 |
| TAX1BP1 | NM_006024 |
| BDH2 | NM_020139 |
| PSME4 | NM_014614 |
| GOLPH3L | NM_018178 |
| SLC16A1 | NM_003051 |
| PLOD2 | NM_182943 |
| SLC39A6 | NM_012319 |
| DNAJB14 | NM_024920 |
| LAPTM4B | NM_018407 |
| COX15 | NM_004376 |
| SMC3 | NM_005445 |
| ADAM9 | NM_003816 |
| ARL6IP1 | NM_015161 |
| FAM18B | NM_016078 |
| MPHOSPH9 | NM_022782 |
| BAT2D1 | NM_015172 |
| WASL | NM_003941 |
| KLHL21 | NM_014851 |
| TIMP3 | NM_000362 |
| GRAMD3 | NM_023927 |
| LGALS8 | NM_006499 |
| BCLAF1 | NM_014739 |
| PCYOX1 | NM_016297 |
| EID1 | NM_014335 |
| LSR | NM_015925 |
| ITM2B | NM_021999 |
| ADCY9 | NM_001116 |
| CRIM1 | NM_016441 |
| EFEMP1 | NM_004105 |
| ANKRD12 | NM_015208 |
| RDH11 | NM_016026 |
| CRX | NM_000554 |
| SLC24A1 | NM_004727 |
| PAX6 | NM_000280 |
| OTX2 | NM_021728 |
| KRT8 | NM_002273 |
| RLBP1 | NM_000326 |
| MERTK | NM_006343 |
| MLANA | NM_005511 |
| RAB27A | NM_183236 |
| OCA2 | NM_000275 |
| KCNJ13 | NM_002242 |
| CFTR | NM_000492 |
| CLDN19 | NM_148960 |
| CLDN10 | NM_182848 |
| CLDN16 | NM_006580 |
| BSG | NM_001728 |
| COL4A3 | NM_000091 |
| FNDC5 | NM_153756 |
| ABCC8 | NM_000352 |
| CLCN2 | NM_004366 |
| SOX2 | NM_003106 |
| KLF4 | NM_004235 |
| CCND1 | NM_053056 |
| RDH5 | NM_002905 |
| COL8A1 | NM_001850 |
| COL9A1 | NM_001851 |
| KRT5 | NM_000424 |
| PTCH1 | NM_000264 |
| SLC7A5 | NM_003486 |
| SLC2A1 | NM_006516 |
| IGFBP5 | NM_000599 |
| KRT6B | NM_005555 |
| CTNND2 | NM_001332 |
| SOX9 | NM_000346 |
| KCNJ10 | NM_002241 |
| KCNJ11 | NM_000525 |
| KCNA2 | NM_004974 |
| KCNB1 | NM_004975 |
| CACNA1B | NM_000718 |
| CRYAB | NM_001885 |
| B2M | NM_004048 |
| HPRT1 | NM_000194 |
| RPL13A | NM_012423 |
| GAPDH | NM_002046 |
| ACTB | NM_001101 |
| HGDC | SA_00105 |
| SLC12A1 | NM_000338 |
| MYC | NM_002467 |

The cells can express at least 50, 100, 150, 200, 250, 300, 350, 360, 370 or all of these genes. In some embodiments, the cells express MITF (GENBANK® Accession No. NM_000248), PAX6 (GENBANK® Accession No. NM_000280), LHX2 (GENBANK® Accession No. NM_004789), TFEC (GENBANK® Accession No. NM_012252), CDH1 (GENBANK® Accession No. NM_004360), CDH3 (GENBANK® Accession No. NM_001793), CLDN10 (GENBANK® Accession No. NM_182848), CLDN16 (GENBANK® Accession No. NM_006580), CLDN19 (GENBANK® Accession No. NM_148960), BEST1 (GENBANK® Accession No. NM_004183), TIMP3 (GENBANK® Accession No. NM_000362), TRPM1 (GENBANK® Accession No. NM_002420), TRPM3 (GENBANK® Accession No. NM_020952), TTR (GENBANK® Accession No. NM_000371), VEGFA (GENBANK® Accession No. NM_003376), CSPG5 (GENBANK® Accession No. NM_006574), DCT (GENBANK® Accession No. NM_001922), TYRP1 (GENBANK® Accession No. NM_000550), TYR (GENBANK® Accession No.

NM_000372), SILV (GENBANK® Accession No. NM_006928), SIL1 (GENBANK® Accession No. NM_022464), MLANA (NM_005511), RAB27A (GENBANK® Accession No. NM_183236), OCA2 (GENBANK® Accession No. NM_000275), GPR143 (GENBANK® Accession No. NM_000273), GPNMB (GENBANK® Accession No. NM_002510), MYO6 (GENBANK® Accession No. NM_004999), MYRIP (GENBANK® Accession No. NM_015460), RPE65 (GENBANK® Accession No. NM_000329), RBP1 (GENBANK® Accession No. NM_002899), RBP4 (GENBANK® Accession No. NM_006744), RDH5 (GENBANK® Accession No. NM_002905), RDH11 (GENBANK® Accession No. NM_016026), RLBP1 (GENBANK® Accession No. NM_000326), MERTK (GENBANK® Accession No. NM_006343), ALDH1A3 (GENBANK® Accession No. NM_000693), FBLN1 (GENBANK® Accession No. NM_001996), SLC16A1 (GENBANK® Accession No. NM_003051), KCNV2 (GENBANK® Accession No. NM_133497), KCNJ13 (GENBANK® Accession No. NM_002242), and CFTR (GENBANK® Accession No. NM_000492). In other embodiments, the RPE cells express 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 38, 39, 40 or all of these proteins. The GENBANK® disclosures are incorporated by reference herein, as available on Jan. 31, 2013.

In some embodiments, the RPE cells express MITF, PAX6, LHX2, TFEC, CDH1, CDH3, CLDN10, CLDN16, CLDN19, BEST1, TIMP3, TRPM1, TRPM3, TTR, VEGFA, CSPG5, DCT, TYRP1, TYR, SILV, SIL1, MLANA, RAB27A, OCA2, GPR143, GPNMB, MYO6, MYRIP, RPE65, RBP1, RBP4, RDH5, RDH11, RLBP1, MERTK, ALDH1A3, FBLN1, SLC16A1, KCNV2, KCNJ13, and CFTR.

In further embodiments, the RPE cells also express one or more microRNAs. In specific non-limiting examples, the cells express one or more of microRNAs listed in Table 2.

TABLE 2

| Position | Query | Precursor miRNA Accession | Precursor miRNA Sanger ID | Precursor Version | Mature miRNA Accession | Mature miRNA Sanger ID |
|---|---|---|---|---|---|---|
| 1 | hsa-miR-9* | MI0000466 | hsa-mir-9-1 | 14 | MIMAT0000442 | hsa-miR-9* |
| 2 | hsa-miR-99a | MI0000101 | hsa-mir-99a | 14 | MIMAT0000097 | hsa-miR-99a |
| 3 | hsa-miR-105 | MI0000111 | hsa-mir-105-1 | 14 | MIMAT0000102 | hsa-miR-105 |
| 4 | hsa-miR-107 | MI0000114 | hsa-mir-107 | 14 | MIMAT0000104 | hsa-miR-107 |
| 5 | hsa-miR-125b | MI0000446 | hsa-mir-125b-1 | 14 | MIMAT0000423 | hsa-miR-125b |
| 6 | hsa-miR-129* | MI0000252 | hsa-mir-129-1 | 14 | MIMAT0004548 | hsa-miR-129* |
| 7 | hsa-miR-152 | MI0000462 | hsa-mir-152 | 14 | MIMAT0000438 | hsa-miR-152 |
| 8 | hsa-miR-184 | MI0000481 | hsa-mir-184 | 14 | MIMAT0000454 | hsa-miR-184 |
| 9 | hsa-miR-187 | MI0000274 | hsa-mir-187 | 14 | MIMAT0000262 | hsa-miR-187 |
| 10 | hsa-miR-198 | MI0000240 | hsa-mir-198 | 14 | MIMAT0000228 | hsa-miR-198 |
| 11 | hsa-miR-200a | MI0000737 | hsa-mir-200a | 14 | MIMAT0000682 | hsa-miR-200a |
| 12 | hsa-miR-200b | MI0000342 | hsa-mir-200b | 14 | MIMAT0000318 | hsa-miR-200b |
| 13 | hsa-miR-203 | MI0000283 | hsa-mir-203 | 14 | MIMAT0000264 | hsa-miR-203 |
| 14 | hsa-miR-204 | MI0000284 | hsa-mir-204 | 14 | MIMAT0000265 | hsa-miR-204 |
| 15 | hsa-miR-205 | MI0000285 | hsa-mir-205 | 14 | MIMAT0000266 | hsa-miR-205 |
| 16 | hsa-miR-211 | MI0000287 | hsa-mir-211 | 14 | MIMAT0000268 | hsa-miR-211 |
| 17 | hsa-miR-221 | MI0000298 | hsa-mir-221 | 14 | MIMAT0000278 | hsa-miR-221 |
| 18 | hsa-miR-222 | MI0000299 | hsa-mir-222 | 14 | MIMAT0000279 | hsa-miR-222 |
| 19 | hsa-miR-302b | MI0000772 | hsa-mir-302b | 14 | MIMAT0000715 | hsa-miR-302b |
| 20 | hsa-miR-9 | MI0000466 | hsa-mir-9-1 | 14 | MIMAT0000441 | hsa-miR-9 |
| 21 | hsa-miR-34b | MI0000742 | hsa-mir-34b | 14 | MIMAT0004676 | hsa-miR-34b |
| 22 | hsa-miR-96 | MI0000098 | hsa-mir-96 | 14 | MIMAT0000095 | hsa-miR-96 |
| 23 | hsa-miR-135b | MI0000810 | hsa-mir-135b | 14 | MIMAT0000758 | hsa-miR-135b |
| 24 | hsa-miR-138 | MI0000476 | hsa-mir-138-1 | 14 | MIMAT0000430 | hsa-miR-138 |
| 25 | hsa-miR-149 | MI0000478 | hsa-mir-149 | 14 | MIMAT0000450 | hsa-miR-149 |
| 26 | hsa-miR-181a | MI0000289 | hsa-mir-181a-1 | 14 | MIMAT0000256 | hsa-miR-181a |
| 27 | hsa-miR-181b | MI0000270 | hsa-mir-181b-1 | 14 | MIMAT0000257 | hsa-miR-181b |
| 28 | hsa-miR-182 | MI0000272 | hsa-mir-182 | 14 | MIMAT0000259 | hsa-miR-182 |
| 29 | hsa-miR-183 | MI0000273 | hsa-mir-183 | 14 | MIMAT0000261 | hsa-miR-183 |
| 30 | hsa-miR-126 | MI0000471 | hsa-mir-126 | 14 | MIMAT0000445 | hsa-miR-126 |
| 31 | hsa-miR-127-3p | MI0000472 | hsa-mir-127 | 14 | MIMAT0000446 | hsa-miR-127-3p |
| 32 | hsa-miR-127-5p | MI0000472 | hsa-mir-127 | 14 | MIMAT0004604 | hsa-miR-127-5p |
| 33 | hsa-miR-134 | MI0000474 | hsa-mir-134 | 14 | MIMAT0000447 | hsa-miR-134 |
| 34 | hsa-miR-137 | MI0000454 | hsa-mir-137 | 14 | MIMAT0000429 | hsa-miR-137 |
| 35 | hsa-miR-142-3p | MI0000458 | hsa-mir-142 | 14 | MIMAT0000434 | hsa-miR-142-3p |
| 36 | hsa-miR-145 | MI0000461 | hsa-mir-145 | 14 | MIMAT0000437 | hsa-miR-145 |
| 37 | hsa-miR-146a | MI0000477 | hsa-mir-146a | 14 | MIMAT0000449 | hsa-miR-146a |
| 38 | hsa-miR-150 | MI0000479 | hsa-mir-150 | 14 | MIMAT0000451 | hsa-miR-150 |
| 39 | hsa-miR-155 | MI0000681 | hsa-mir-155 | 14 | MIMAT0000646 | hsa-miR-155 |
| 40 | hsa-miR-214 | MI0000290 | hsa-mir-214 | 14 | MIMAT0000271 | hsa-miR-214 |
| 41 | hsa-miR-223 | MI0000300 | hsa-mir-223 | 14 | MIMAT0000280 | hsa-miR-223 |
| 42 | hsa-miR-323-3p | MI0000807 | hsa-mir-323 | 14 | MIMAT0000755 | hsa-miR-323-3p |
| 43 | hsa-miR-323-5p | MI0000807 | hsa-mir-323 | 14 | MIMAT0004696 | hsa-miR-323-5p |
| 44 | hsa-miR-17 | MI0000071 | hsa-mir-17 | 14 | MIMAT0000070 | hsa-miR-17 |
| 45 | hsa-miR-18a | MI0000072 | hsa-mir-18a | 14 | MIMAT0000072 | hsa-miR-18a |
| 46 | hsa-miR-19a | MI0000073 | hsa-mir-19a | 14 | MIMAT0000073 | hsa-miR-19a |
| 47 | hsa-miR-20a | MI0000076 | hsa-mir-20a | 14 | MIMAT0000075 | hsa-miR-20a |
| 48 | hsa-miR-302a | MI0000738 | hsa-mir-302a | 14 | MIMAT0000684 | hsa-miR-302a |
| 49 | hsa-miR-302a* | MI0000738 | hsa-mir-302a | 14 | MIMAT0000683 | hsa-miR-302a* |
| 50 | hsa-miR-302b* | MI0000772 | hsa-mir-302b | 14 | MIMAT0000714 | hsa-miR-302b* |

TABLE 2-continued

| Position | Query | Precursor miRNA Accession | Precursor miRNA Sanger ID | Precursor Version | Mature miRNA Accession | Mature miRNA Sanger ID |
|---|---|---|---|---|---|---|
| 51 | hsa-miR-302c | MI0000773 | hsa-mir-302c | 14 | MIMAT0000717 | hsa-miR-302c |
| 52 | hsa-miR-302c* | MI0000773 | hsa-mir-302c | 14 | MIMAT0000716 | hsa-miR-302c* |
| 53 | hsa-miR-367* | MI0000775 | hsa-mir-367 | 14 | MIMAT0004686 | hsa-miR-367* |
| 54 | hsa-miR-371-3p | MI0000779 | hsa-mir-371 | 14 | MIMAT0000723 | hsa-miR-371-3p |
| 55 | hsa-miR-371-5p | MI0000779 | hsa-mir-371 | 14 | MIMAT0004687 | hsa-miR-371-5p |
| 56 | hsa-miR-372 | MI0000780 | hsa-mir-372 | 14 | MIMAT0000724 | hsa-miR-372 |
| 57 | hsa-miR-373 | MI0000781 | hsa-mir-373 | 14 | MIMAT0000726 | hsa-miR-373 |
| 58 | hsa-miR-373* | MI0000781 | hsa-mir-373 | 14 | MIMAT0000725 | hsa-miR-373* |
| 59 | hsa-miR-199b-3p | MI0000282 | hsa-mir-199b | 14 | MIMAT0004563 | hsa-miR-199b-3p |
| 60 | hsa-Let-7b | MI0000063 | hsa-let-7b | 14 | MIMAT0000063 | hsa-let-7b |
| 61 | hsa-Let-7c | MI0000064 | hsa-let-7c | 14 | MIMAT0000064 | hsa-let-7c |
| 62 | hsa-Let-7d | MI0000065 | hsa-let-7d | 14 | MIMAT0000065 | hsa-let-7d |
| 63 | hsa-Let-7g | MI0000433 | hsa-let-7g | 14 | MIMAT0000414 | hsa-let-7g |
| 64 | hsa-miR-200c | MI0000650 | hsa-mir-200c | 14 | MIMAT0000617 | hsa-miR-200c |
| 65 | hsa-miR-147 | MI0000262 | hsa-mir-147 | 14 | MIMAT0000251 | hsa-miR-147 |
| 66 | hsa-miR-429 | MI0001641 | hsa-mir-429 | 14 | MIMAT0001536 | hsa-miR-429 |
| 67 | hsa-miR-124 | MI0000443 | hsa-mir-124-1 | 14 | MIMAT0000422 | hsa-miR-124 |
| 68 | hsa-miR-124* | MI0000443 | hsa-mir-124-1 | 14 | MIMAT0004591 | hsa-miR-124* |
| 69 | hsa-miR-216a | MI0000292 | hsa-mir-216a | 14 | MIMAT0000273 | hsa-miR-216a |
| 70 | hsa-miR-216b | MI0005569 | hsa-mir-216b | 14 | MIMAT0004959 | hsa-miR-216b |
| 71 | hsa-miR-139-3p | MI0000261 | hsa-mir-139 | 14 | MIMAT0004552 | hsa-miR-139-3p |
| 72 | hsa-miR-139-5p | MI0000261 | hsa-mir-139 | 14 | MIMAT0000250 | hsa-miR-139-5p |
| 73 | hsa-miR-199a-3p | MI0000242 | hsa-mir-199a-1 | 14 | MIMAT0000232 | hsa-miR-199a-3p |
| 74 | hsa-miR-199a-5p | MI0000242 | hsa-mir-199a-1 | 14 | MIMAT0000231 | hsa-miR-199a-5p |
| 75 | hsa-miR-92a | MI0000093 | hsa-mir-92a-1 | 14 | MIMAT0000092 | hsa-miR-92a |
| 76 | hsa-miR-92a-1* | MI0000093 | hsa-mir-92a-1 | 14 | MIMAT0004507 | hsa-miR-92a-1* |
| 77 | hsa-Let-7a | MI0000060 | hsa-let-7a-1 | 14 | MIMAT0000062 | hsa-let-7a |
| 78 | hsa-Let-7a* | MI0000060 | hsa-let-7a-1 | 14 | MIMAT0004481 | hsa-let-7a* |
| 79 | hsa-Let-7a-2* | MI0000061 | hsa-let-7a-2 | 14 | MIMAT0010195 | hsa-let-7a-2* |
| 80 | hsa-miR-455-3p | MI0003513 | hsa-mir-455 | 14 | MIMAT0004784 | hsa-miR-455-3p |
| 81 | hsa-miR-455-5p | MI0003513 | hsa-mir-455 | 14 | MIMAT0003150 | hsa-miR-455-5p |
| 82 | hsa-miR-584 | MI0003591 | hsa-mir-584 | 14 | MIMAT0003249 | hsa-miR-584 |
| 83 | hsa-miR-886-5p | MI0005527 | hsa-mir-886 | 14 | MIMAT0004905 | hsa-miR-886-5p |
| 84 | hsa-miR-34a | MI0000268 | hsa-mir-34a | 14 | MIMAT0000255 | hsa-miR-34a |
| 85 | hsa-miR-217 | MI0000293 | hsa-mir-217 | 14 | MIMAT0000274 | hsa-miR-217 |
| 86 | hsa-miR-186 | MI0000483 | hsa-mir-186 | 14 | MIMAT0000456 | hsa-miR-186 |
| 87 | hsa-miR-148a | MI0000253 | hsa-mir-148a | 14 | MIMAT0000243 | hsa-miR-148a |
| 88 | hsa-miR-340 | MI0000802 | hsa-mir-340 | 14 | MIMAT0004692 | hsa-miR-340 |
| 89 | SNORD48 | NR_002745 | SNORD48 | | | |
| 90 | SNORD47 | NR_002746 | SNORD47 | | | |
| 91 | SNORD44 | NR_002750 | SNORD44 | | | |
| 92 | RNU6-2 | NR_002752 | RNU6-2 | | | |
| 93 | miRTC | N/A | miRTC | | | |
| 94 | miRTC | N/A | miRTC | | | |
| 95 | PPC | N/A | PPC | | | |
| 96 | PPC | N/A | PPC | | | |

Thus, in some embodiments, the cells express at least 2, 5, 10, 15, 20, 25, 30, 35, 40, 45, 50, 55, 60, 65, 70, 80, 85, 90, 95 or all 96 of the miRNAs listed in Table 2. In one specific, non-limiting example, the cells express miR204 and miR211.

Control Genes include, but are not limited to, the genes listed in Table 3 below.

TABLE 3

| | |
|---|---|
| POU5F1 | NM_002701 |
| T | NM_003181 |
| TF | NM_001063 |
| HOXB5 | NM_002147 |
| KRT23 | NM_015515 |
| HOXA4 | NM_002141 |
| VSX2 | NM_182894 |
| AFP | NM_001134 |
| FOXA2 | NM_021784 |
| SMAD3 | NM_005902 |
| NANOG | NM_024865 |

These genes are expressed in RPE cells and in control cells. Thus, in some embodiments, the RPE cells express one or more of these markers. The RPE cells can express 1, 2, 3, 4, 5, 6, 7, 8, 9, 10 or all of these markers.

In yet other embodiments the RPE cells have a resting potential of about −50 to about −60 mV, and a fluid transport rate of about 5 to about 10 μl cm$^{-2}$h$^{-1}$. In additional embodiments, the RPE cells express MITF, PAX6, LHX2, TFEC, CDH1, CDH3, CLDN10, CLDN16, CLDN19, BEST1, TIMP3, TRPM1, TRPM3, TTR, VEGFA, CSPG5, DCT, TYRP1, TYR, SILV, SILL MLANA, RAB27A, OCA2, GPR143, GPNMB, MYO6, MYRIP, RPE65, RBP1, RBP4, RDH5, RDH11, RLBP1, MERTK, ALDH1A3, FBLN1, SLC16A1, KCNV2, KCNJ13, and CFTR, express miR204 and miR211, have a resting potential of about −50 to about −60 mV and have a fluid transport rate of about 5 to about 10 μl cm$^{-2}$h$^{-1}$.

Compositions are also provided that include a scaffold, such as a polymeric carrier and/or an extracellular matrix, and an effective amount of the RPE cells disclosed herein. The extracellular matrix can be a human extracellular matrix. The polymeric particle can be a microparticle. In some embodiments, the cells are provided as a monolayer.

A variety of biological or synthetic solid matrix materials (i.e., solid support matrices, biological adhesives or dressings, and biological/medical scaffolds) are suitable for use. The matrix material is generally physiologically acceptable and suitable for use in vivo applications. Non-limiting examples of such physiologically acceptable materials include, but are not limited to, solid matrix materials that are absorbable and/or non-absorbable, such as small intestine submucosa (SIS), e.g., porcine-derived (and other SIS sources); crosslinked or non-crosslinked alginate, hydrocolloid, foams, collagen gel, collagen sponge, polyglycolic acid (PGA) mesh, polyglactin (PGL) mesh, fleeces, and bioadhesives (e.g., fibrin glue and fibrin gel). The polymer can be poly(DL)-lactic-co-glycolic) acid (PLGA) (see Lu et al., J. Biomater Sci Polym Ed. 9(11): 1187-205, 1998). In other embodiments, the matric includes poly(L-lactic acid) (PLLA) and poly(D,L-lactic-co-glycolic acid) (PLGA) such as with a co-polymer ratio of about 90:10, 75:25, 50:50, 25:75, 10:90 (PLLA:PLGA) (see Thomson et al., J. Biomed. Mater Res. A 95: 1233-42, 2010).

Suitable polymeric carriers also include porous meshes or sponges formed of synthetic or natural polymers, as well as polymer solutions. One non-limiting form of a matrix is a polymeric mesh or sponge. Another non-limiting example is a polymeric hydrogel. Natural polymers that can be used include proteins such as collagen, albumin, and fibrin; and polysaccharides such as alginate and polymers of hyaluronic acid. Synthetic polymers include both biodegradable and non-biodegradable polymers. Examples of biodegradable polymers include polymers of hydroxy acids such as polylactic acid (PLA), polyglycolic acid (PGA), and polylactic acid-glycolic acid (PLGA), polyorthoesters, polyanhydrides, polyphosphazenes, and combinations thereof. Non-biodegradable polymers include polyacrylates, polymethacrylates, ethylene vinyl acetate, and polyvinyl alcohols.

Polymers that can form ionic or covalently crosslinked hydrogels which are malleable can be used. A hydrogel is a substance formed when an organic polymer (natural or synthetic) is crosslinked via covalent, ionic, or hydrogen bonds to create a three-dimensional open-lattice structure which entraps water molecules to form a gel. Examples of materials which can be used to form a hydrogel include polysaccharides such as alginate, polyphosphazines, and polyacrylates, which are crosslinked ionically, or block copolymers such as PLURONICS™ or TETRONICS™, polyethylene oxide-polypropylene glycol block copolymers which are crosslinked by temperature or pH, respectively. Other materials include proteins such as fibrin, polymers such as polyvinylpyrrolidone, hyaluronic acid and collagen.

In general, these polymers are at least partially soluble in aqueous solutions, such as water, buffered salt solutions, or aqueous alcohol solutions that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups. Examples of polymers with basic side groups that can be reacted with anions are poly(vinyl amines), poly(vinyl pyridine), poly (vinyl imidazole), and some imino substituted polyphosphazenes. The ammonium or quaternary salt of the polymers can also be formed from the backbone nitrogens or pendant imino groups. Examples of basic side groups are amino and imino groups.

Non-limiting examples of suitable materials for the substrate include parylene polypropylene, polyimide, glass, nitinol, polyvinyl alcohol, polyvinyl pyrolidone, collagen, chemically-treated collagen, polyethersulfone (PES), poly (glycerol-sebacate) PGS, poly(styrene-isobutyl-styrene), polyurethane, ethyl vinyl acetate (EVA), polyetherether ketone (PEEK), Kynar (Polyvinylidene Fluoride; PVDF), Polytetrafluoroethylene (PTFE), Polymethylmethacrylate (PMMA), Pebax, acrylic, polyolefin, polydimethylsiloxane (PDMS) and other silicone elastomers, polypropylene, hydroxyapetite, titanium, gold, silver, platinum, other metals and alloys, ceramics, plastics and mixtures or combinations thereof. Additional suitable materials used to construct certain embodiments of the substrates include, but are not limited to, poly-para-xylylenes (e.g., parylene, including but not limited to parylene A, parylene AM, parylene C, ammonia treated parylene, parylene C treated with polydopamine), poly(lactic acid) (PLA), polyethylene-vinyl acetate, poly (lactic-co-glycolic acid) (PLGA), poly(D,L-lactide), poly (D,L-lactide-co-trimethylene carbonate), collagen, heparinized collagen, denatured collagen, modified collagen (e.g., silicone with gelatin), other cell growth matrices (such as SYNTHEMAX™), poly(caprolactone), poly(glycolic acid), and/or other polymer, copolymers, or block co-polymers, poly(caprolactone) containing cyclic Arginine-Glycine-Asparagine, cyclic or linear Arginine-Glycine-aspartic acid, blends of polycaprolactone and polyethylene glycol (PCL-PEG), thermoplastic polyurethanes, silicone-modified polyether urethanes, poly(carbonate urethane), or polyimide. Thermoplastic polyurethanes are polymers or copolymers which may comprise aliphatic polyurethanes, aromatic polyurethanes, polyurethane hydrogel-forming materials, hydrophilic polyurethanes, or combinations thereof. Non-limiting examples include elasthane (poly(ether urethane)) such as ELASTHANE™ 80A, Lubrizol, TECOPHILIC™, PELLETHANE™, CARBOTHANE™, TECOTHANE™, TECOPLAST™, AND ESTANE™. Silicone-modified polyether urethanes may include CARBOSIL™ 20 or PUR-SIL™ 20 80A, and the like. Poly(carbonate urethane) may include BIONATE™ 80A or similar polymers. Moreover, in several embodiments the substrate (and/or the cells) comprises materials (or chemicals) that allow for visualization of the substrate in situ, which are unaffected by the cryopreservation (and thawing) of the substrate and cells The retinal pigment epithelial cells produced by the methods disclosed herein can be cryopreserved, see for example, PCT Publication No. 2012/149484 A2, which is incorporated by reference herein. The cells can be cryopreserved with or without a substrate. In several embodiments, the storage temperature ranges from about −50° C. to about −60° C., about −600° C. to about −70° C., about −70° C. to about −80° C., about −80° C. to about −90° C., about −90° C. to about −100° C., and overlapping ranges thereof. In some embodiments, lower temperatures are used for the storage (e.g., maintenance) of the cryopreserved cells. In several embodiments, liquid nitrogen (or other similar liquid coolant) is used to store the cells. In further embodiments, the cells are stored for greater than about 6 hours. In additional embodiments, the cells are stored about 72 hours. In several embodiments, the cells are stored 48 hours to about one week. In yet other embodiments, the cells are stored for about 1, 2, 3, 4, 5, 6, 7, or 8 weeks. In further embodiments, the cells are stored for 1, 2, 3, 4, 5, 67, 8, 9, 10, 11 or 12 months. The cells can also be stored for longer times. The cells can be cryopreserved separately or on a substrate, such as any of the substrates disclosed herein.

A general method of cryopreserving cells is disclosed herein, that can be used for cryopreservation of any cell type, such as stem cells, including iPSCs, and differentiated cells, such as retinal pigment epithelial cells. The method includes the use of alginate. "Alginate" (or "alginic acid" or "algin") refers to the anionic polysaccharide distributed widely in the cell walls of brown algae. Alginate forms water-soluble salts with alkali metals, such as sodium, potassium, lithium, magnesium, ammonium, and the substituted ammonium cations derived from lower amines, such as methyl amine, ethanol amine, diethanol amine, and triethanol amine. Alginate includes calcium alginate, sodium alginate, propyleneglycol alginate, and potassium alginate.

In some embodiments, cells, such as the disclosed retinal pigment epithelial cells are contacted with an effective amount of alginate. The cells are contacted with alginate, and then exposed to divalent cations, such as Calcium, Barium, Copper, Zinc or Strontium) which results in cross-linking of the alginate polymers in the cell/liquid alginate suspension (see for example, U.S. Published Patent Application No. 2012/0171295, incorporated herein by reference). In certain embodiments, the divalent cation used to cross-link the alginate in the cell/liquid alginate solution is calcium chloride ($CaCl_2$), barium chloride ($BaCl_2$), strontium chloride ($SrCl_2$), copper chloride ($CuCl_2$), or zinc chloride ($ZnCl_2$). In a specific embodiment, the divalent cation used to cross-link the alginate in the cell/liquid alginate solution is calcium chloride ($CaCl_2$). In certain embodiments, the solution of divalent cation comprises about 0.5%, about 0.75%, about 1.0%, about 1.25%, about 1.5%, about 1.75%, or about 2.0% divalent cation. In a specific embodiment, the solution of divalent cation comprises 1.5% divalent cation, e.g., $CaCl_2$.

In some embodiments, additional cryoprotectants can be used. For example, cells can be cryopreserved in a cryopreservation solution comprising one or more cryoprotectants, such as DMSO, serum albumin, such as human or bovine serum albumin. In certain embodiments, the solution comprises about 1%, about 1.5%, about 2%, about 2.5%, about 3%, about 4%, about 5%, about 6%, about 7%, about 8%, about 9%, or about 10% DMSO. In other embodiments, the solution comprises about 1% to about 3%, about 2% to about 4%, about 3% to about 5%, about 4% to about 6%, about 5% to about 7%, about 6% to about 8%, about 7% to about 9%, or about 8% to about 10% DMSO or albumin. In a specific embodiment, the solution comprises 2.5% DMSO. In another specific embodiment, the solution comprises 10% DMSO.

Cells can be cryopreserved in small containers (e.g., ampoules); in bags suitable for cryopreservation; or in any other suitable container for cryopreservation. In some embodiments, cells are cryopreserved in commercially available cryopreservation medium. The cells can be cryopreserved in a cryopreservation solution comprising one or more solutions for use in storing cells. Cryopreservation solutions included CryoStor CS10® and HYPOTHERMOSO1® (BioLife Solutions, Bothell, Wash.)). In certain embodiments, the solution comprises about 25%, about 30%, about 35%, about 40%, about 45%, about 50%, about 55%, about 60%, about 65%, or about 70% HYPOTHERMOSOL®. In other embodiments, the solution comprises about 25% to about 50%, about 40% to about 60%, about 50% to about 60%, about 50% to about 70%, or about 60% to about 70% HYPOTHERMOSOL®. In a specific embodiment, the solution comprises 55% HYPOTHERMOSOL®.

In another specific embodiment, the solution comprises 57.5% HYPOTHERMOSOL®. In additional embodiments, the cryopreservation solution can include one or more excipients, such as dextran, starch, glucose, lactose, sucrose, gelatin, silica gel, glycerol monostearate, sodium chloride, glycerol, propylene, and/or glycol. The cryopreservation solution can include media, such as the media disclosed herein. In additional embodiments, the medium can be phosphate buffered saline or Dulbecco's Modified Eagle's Medium (DMEM).

Cells may be cooled, for example, at about 1° C./minute during cryopreservation. In some embodiments, the cryopreservation temperature is about −80° C. to about −180° C., or about −125° C. to about −140° C. In some embodiments, the cells are cooled to 4° C. prior to cooling at about 1° C./minute. Cryopreserved cells can be transferred to vapor phase of liquid nitrogen prior to thawing for use. In some embodiments, for example, once the cells have reached about −80° C., they are transferred to a liquid nitrogen storage area. Cryopreservation can also be done using a controlled-rate freezer. Cryopreserved cells may be thawed, e.g., at a temperature of about 25° C. to about 40° C., and typically at a temperature of about 37° C.

The human RPE cells described herein, or a pharmaceutical composition including these cells, can be used for the manufacture of a medicament to treat a condition in a patient in need thereof. The RPE cells can be previously cryopreserved. The disclosed RPE cells are derived from iPSCs, and thus can be used to provide "personalized medicine" for patients with eye diseases. In some embodiments, somatic cells obtained from patients can be genetically engineered to correct the disease causing mutation, differentiated into RPE, and engineered to form an RPE tissue. This RPE tissue can be used to replace the endogenous degenerated RPE of the same patient. Alternatively, iPSCs can be generated from a healthy donor or from HLA homozygous "super-donors" can be used. RPE cells can be treated in vitro with certain factors, such as pigment epithelium-derived factor (PEDF), transforming growth factor (TGF)-beta, and/or retinoic acid to generate an anti-inflammatory and immunosuppressive environment in vivo.

Various eye conditions may be treated or prevented by the introduction of the RPE cells obtained using the methods disclosed herein. The conditions include retinal diseases or disorders generally associated with retinal dysfunction or degradation, retinal injury, and/or loss of retinal pigment epithelium. Conditions that can be treated include, without limitation, degenerative diseases of the retina, such as Stargardt's macular dystrophy, retinitis pigmentosa, macular degeneration (such as age related macular degeneration), glaucoma, and diabetic retinopathy. Additional conditions include Lebers congenital amaurosis, hereditary or acquired macular degeneration, Best disease, retinal detachment, gyrate atrophy, choroideremia, pattern dystrophy, other dystrophies of the RPE, and RPE and retinal damage due to damage caused by any one of photic, laser, inflammatory, infectious, radiation, neovascular or traumatic injury. In certain embodiments, methods are provided for treating or preventing a condition characterized by retinal degeneration, comprising administering to a subject in need thereof an effective amount of a composition comprising RPE cells. These methods can include selecting a subject with one or more of these conditions, and administering a therapeutically effective amount of the RPE cells sufficient to treat the condition and/or ameliorate symptoms of the condition. The RPE cells may be transplanted in various formats. For example, the RPE cells may be introduced into the target site an the form of cell suspension, or adhered onto a matrix, extracellular matrix or substrate such as a biodegradable polymer, as a monolayer, or a combination. The RPE cells may also be transplanted together (co-transplantation) with other retinal cells, such as with photoreceptors. In some embodiments, the RPE cells are produced from iPSCs from the subject to be treated, and thus are autologous. In other embodiments, the RPE cells are produced from an MHC-matched donor.

The RPE cells can be introduced to various target sites within a subject's eye. In some embodiments, RPE cells are introduced, such as by transplantation, to the subretinal space of the eye, which is the anatomical location of the RPE (between the photoreceptor outer segments and the choroids) in mammals. In addition, dependent upon migratory ability and/or positive paracrine effects of the cells, introduction into additional ocular compartments can be considered, such as the vitreal space, the inner or outer retina, the retinal periphery and within the choroids.

The cells can be introduced by various techniques known in the art. Methods for performing RPE transplants are disclosed in, for example, in U.S. Pat. Nos. 5,962,027, 6,045,791, and 5,941,250; Biochem Biophys Res Commun Feb. 24, 2000; 268(3): 842-6; and Opthalmic Surg February 1991; 22(2): 102-8). Methods for performing corneal transplants are described in, for example, U.S. Pat. No. 5,755,785; Curr Opin Opthalmol August 1992; 3 (4): 473-81; Ophthalmic Surg Lasers April 1998; 29 (4): 305-8; and Opthalmology April 2000; 107 (4): 719-24. In some embodiments, transplantation is performed via pars pana vitrectomy surgery followed by delivery of the RPE cells through a small retinal opening into the sub-retinal space or by direct injection. Alternatively, RPE cells can be delivered into the subretinal space via a trans-scleral, trans-choroidal approach. In addition, direct trans-scleral injection into the vitreal space or delivery to the anterior retinal periphery in proximity to the ciliary body can be performed.

The cells can also be incorporated into a delivery device. If mainly paracrine effects are to be utilized, cells can be delivered and maintained in the eye encapsulated within a semi-permeable container, which decreases exposure of the cells to the host immune system (Neurotech USA CNTF delivery system; PNAS. 103(10) 3896-3901, 2006).

The RPE cells can be introduced into the target site in the form of cell suspension, adhered onto a matrix, such as extracellular matrix, or provided on substrate such as a biodegradable polymer. The RPE cells can also be transplanted together (co-transplantation) with other cells, such as retinal cells with photoreceptors. Thus, a composition comprising RPE cells obtained by the methods disclosed herein is provided. In some embodiments, these RPE cells include a tyrosinase enhancer operably linked to a promoter and a nucleic acid encoding a marker. In other embodiments, the RPE cells also include a second constitutive promoter operably linked to a nucleic acid encoding a second marker.

Screening Methods and Identification of RPE Cells

Methods are also provided for the identification of RPE cells, and/or confirming a cell is an RPE cell. The cells can be produced using the methods disclosed herein.

A method is provided herein for identifying an agent that alters the differentiation and/or proliferation of RPE cells. In some embodiments, methods are provided for identifying an agent that alters the proliferation of RPE cells. The methods include contacting an RPE cell with an effective amount of an agent of interest. In some embodiments, methods are provided for identifying an agent that increases differentiation of RPE.

In additional embodiments, methods are provided for identifying an agent that affects RPE cell survival, and/or changes the endogenous expression of genes in RPE cells. Therapeutic agents can be identified for the treatment of disease using these methods. In some embodiments, methods are provided for identifying an agent that affects the epithelial phenotype of RPE cells. The method includes contacting iPSCs, RPEs, or embryoid bodies with the agent of interest, and assaying the production and/or survival and/or phenotype of RPE cells. The agent can be introduced into any step of the methods disclosed herein.

RPE cells produced using the methods disclosed herein, or other RPE cells, can also be contact with an agent, and assessed using the methods disclosed below. These methods can be used to identify agents that affect expression of genes, or to identify agents that affect survival of RPE cells. In some embodiments, the RPE cells are treated with a stressor, such as thapsigargin, A23187, DL-dithiothreitol, or 2-deoxy-D-glucose.

The test compound can be any compound of interest, including chemical compounds, small molecules, polypeptides, growth factors, cytokines, or other biological agents (for example antibodies). In several examples, a panel of potential neurotrophic agents are screened. In other embodiments a panel of polypeptide variants is screened.

In some embodiments, methods are provided for determining if an agent of interest increases the differentiation of retinal pigment epithelial cells. The method includes culturing the embryoid bodies produced from human induced pluripotent stem cells comprising a nucleic acid encoding a first marker operably linked to a retinal pigment epithelial cell specific promoter, and comprising a second marker operably linked to a constitutive promoter, as disclosed above, in a first medium comprising two Wnt pathway inhibitor and a Nodal pathway inhibitor. The embryoid bodies are plated on a tissue culture substrate in a second medium that (a) does not comprise beta fibroblast growth fact (bFGF) (b) comprises a basic fibroblast growth factor (bFGF) inhibitor, the two Wnt pathway inhibitors, and the Nodal pathway inhibitor; and (c) comprises about 20 to about 90 ng of Noggin to form differentiating retinal pigment epithelial cells. The differentiating retinal pigment epithelial cells are cultured in a third medium comprising ACTIVAN A and WNT3a. The cells are then cultured in a fourth retinal pigment epithelial cell (RPE) medium comprising about 5% fetal serum, a canonical WNT inhibitor, a non-canonical WNT inducer, and inhibitors of the Sonic and FGF pathway to producing human retinal pigment epithelial cells. Suitable methods are disclosed herein.

One, several or all of these steps are performed in the presence of the agent of interest. The expression of the first marker in the retinal pigment epithelial cells is compared to the expression of the second marker, wherein an increase in expression of the first marker as compared to the second marker indicates that the agent increases the differentiation of retinal pigment epithelial cells Methods for preparing a combinatorial library of molecules that can be tested for a desired activity are well known in the art and include, for example, methods of making a phage display library of peptides, which can be constrained peptides (see, for example, U.S. Pat. Nos. 5,622,699; 5,206,347; Scott and Smith, *Science* 249:386-390, 1992; Markland et al., *Gene* 109:13-19, 1991), a peptide library (U.S. Pat. No. 5,264,563); an FDA-approved drug library (see, for example, Huang, E; Southall, N; Wang, Y et al., *Science Translational Medicine* 3: 1-12); a peptidomimetic library (Blondelle et al., *Trends Anal Chem.* 14:83-92, 1995); a nucleic acid library (O'Connell et al., *Proc. Natl Acad. Sci., USA* 93:5883-5887, 1996; Tuerk and Gold, *Science* 249:505-510, 1990; Gold et al., *Ann. Rev. Biochem.* 64:763-797, 1995); an oligosaccharide library (York et al., *Carb. Res.* 285:99-128, 1996; Liang et al., *Science* 274: 1520-1522, 1996; Ding et al., *Adv. Expt. Med. Biol.* 376: 261-269, 1995); a lipoprotein library (de Kruif et al., *FEBS Lett.* 3 99:23 2-23 6, 1996); a glycoprotein or glycolipid library (Karaoglu et al., *J Cell Biol.* 130.567-577, 1995); or a chemical library containing, for example, drugs or other pharmaceutical agents (Gordon et al., *J Med. Chem.* 37.1385-1401, 1994; Ecker and Crooke, *BioTechnology* 13:351-360, 1995). Polynucleotides can be particularly useful as agents that can alter a function of cells (such as, but not limited to iPSCs, embryoid bodies and RPE cells) because nucleic acid molecules having binding specificity for cellular targets, including cellular polypeptides, exist naturally, and because synthetic molecules having such specificity can be readily prepared and identified (see, for example, U.S. Pat. No. 5,750,342).

In one embodiment, for a high throughput format, iPSCs, embryoid bodies or RPE progenitors can be introduced into wells of a multi-well plate or of a glass slide or microchip, and can be contacted with the test agent. Generally, the cells are organized in an array, particularly an addressable array, such that robotics conveniently can be used for manipulating the cells and solutions and for monitoring the stem or precursor cells, particularly with respect to the function being examined. An advantage of using a high throughput format is that a number of test agents can be examined in parallel, and, if desired, control reactions also can be run under identical conditions as the test conditions. As such, the methods disclosed herein provide a means to screen one, a few, or a large number of test agents in order to identify an agent that can alter a function of cells, for example, an agent that induces the cells to differentiate into a desired cell type, or that affects differentiation, survival and/or cell proliferation. High throughput screens can be used to assess phenotype and survival. These screens can be used to identify drugs that can affect RPE phenotype and survival. In some embodiments, RPE phenotype is assayed by loss/gain of a fluorescent signal and survival is assayed (such as by an ATP based cell titer glow assay).

These methods can include evaluating expression of one or more of the genes listed in Table 1, Table A or FIG. 27C. In some embodiments, the expression of 50, 100, 150, 200, 250, 300, 350, 360, 370 or all of the genes listed in Table 1 can be assessed. For any of these methods, the expression of one or more of MITF (GENBANK® Accession No. NM_000248), PAX6 (GENBANK® Accession No. NM_000280), LHX2 (GENBANK® Accession No. NM_004789), TFEC (GENBANK® Accession No. NM_012252), CDH1 (GENBANK® Accession No. NM_004360), CDH3 (GENBANK® Accession No. NM_001793), CLDN10 (GENBANK® Accession No. NM_182848), CLDN16 (GENBANK® Accession No. NM_006580), CLDN19 (GENBANK® Accession No. NM_148960), BEST1 (GENBANK® Accession No. NM_004183), TIMP3 (GENBANK® Accession No. NM_000362), TRPM1 (GENBANK® Accession No. NM_002420), TRPM3 (GENBANK® Accession No. NM_020952), TTR (GENBANK® Accession No. NM_000371), VEGFA (GENBANK® Accession No. NM_003376), CSPG5 (GENBANK® Accession No. NM_006574), DCT (GENBANK® Accession No. NM_001922), TYRP1 (GENBANK® Accession No. NM_000550), TYR (GENBANK® Accession No. NM_000372), SILV (GENBANK® Accession No. NM_006928), SIL1 (GENBANK® Accession No. NM_022464), MLANA (NM_005511), RAB27A (GENBANK® Accession No. NM_183236), OCA2 (GENBANK® Accession No. NM_000275), GPR143 (GENBANK® Accession No. NM_000273), GPNMB (GENBANK® Accession No. NM_002510), MYO6 (GENBANK® Accession No. NM_004999), MYRIP (GENBANK® Accession No. NM_015460), RPE65 (GENBANK® Accession No. NM_000329), RBP1 (GENBANK® Accession No. NM_002899), RBP4 (GENBANK® Accession No. NM_006744), RDH5 (GENBANK® Accession No. NM_002905), RDH11 (GENBANK® Accession No. NM_016026), RLBP1 (GENBANK® Accession No. NM_000326), MERTK (GENBANK® Accession No. NM_006343), ALDH1A3 (GENBANK® Accession No. NM_000693), FBLN1 (GENBANK® Accession No. NM_001996), SLC16A1 (GENBANK® Accession No. NM_003051), KCNV2 (GENBANK® Accession No. NM_133497), KCNJ13 (GENBANK® Accession No. NM_002242), and CFTR (GENBANK® Accession No. NM_000492) RNA or protein is assessed. The GENBANK® disclosures are incorporated by reference herein, as available on Jan. 31, 2013. Increased expression of the one or more mRNAs or proteins following exposure to the agent, as compared to iPSC or embryoid bodies not contacted with the agent, indicates that the agent affects RPE cell differentiation, survival and/or proliferation, specifically that it increases RPE cell differentiation, survival and/or proliferation. Decreased expression of the one or more mRNAs or proteins following exposure to the agent, as compared to iPSC or embryoid bodies not contacted with the agent, indicates that the agent affects RPE cell differentiation, survival and/or proliferation, specifically that it decreases RPE cell differentiation, survival and/or proliferation.

In other embodiments, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 38, 39, 40 or all of these mRNAs or proteins is assessed. Increased expression of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 38, 39, 40 or all of these mRNAs or proteins indicates that the agent increases RPE cell differentiation, survival and/or proliferation. Decreased expression of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 38, 39, 40 or all of these mRNAs or proteins indicates that the agent decreases RPE cell differentiation, survival and/or proliferation.

In some embodiments, the expression of MITF, PAX6, LHX2, TFEC, CDH1, CDH3, CLDN10, CLDN16, CLDN19, BEST1, TIMP3, TRPM1, TRPM3, TTR, VEGFA, CSPG5, DCT, TYRP1, TYR, SILV, SIL1 MLANA, RAB27A, OCA2, GPR143, GPNMB, MYO6, MYRIP, RPE65, RBP1, RBP4, RDH5, RDH11, RLBP1, MERTK, ALDH1A3, FBLN1, SLC16A1, KCNV2, KCNJ13, and CFTR is assessed. Increased expression indicates that the agent increases RPE cell differentiation, survival or proliferation. Decreased expression indicates that the agent decreases RPE cell differentiation, survival or proliferation. The expression of one or a combination of these markers also can be used to confirm that a cell is a RPE cell.

In additional embodiments, the expression of at least 2, 5, 10, 15, 20, 25, 30, 35, 40, 45, 50, 55, 60, 65, 70, 80, 85, 90, 95 or all 96 of the miRNAs listed in Table 2 is assessed. In further embodiments, the production of miR204 (GEN-BANK® Accession No. NR_029621.1, Dec. 9, 2012, incorporated herein by reference) and/or miR211 (GENBANK® Accession No. NR_029624.1, Sep. 23, 2012, incorporated herein by reference) is assessed. Increased production of one or both of the microRNAs indicates that the agent affects RPE cells differentiation and/or proliferation, or confirms that the cell is an RPE. Increased expression indicates that the agent increases RPE cell differentiation, survival or proliferation. Decreased expression indicates that the agent decreases RPE cell differentiation, survival or proliferation. These miRNAs can be detected using the exemplary methods for detecting nucleic acids disclosed above.

In other embodiments, the expression of one or more of the genes listed in Table 3 is also assessed. The expression of these genes can be used as a control, such as a reference standard. Thus, in some embodiments, the expression of these genes does not change in the presence of the agent of interest. These genes can also be used as reference standards.

In yet other embodiments, expression of one or more of the molecules listed in FIG. 27C is evaluated. Thus, in some embodiments, 1, 2, 3, 4, 5, 6, 7, 8, 9 or 10 of the molecules listed in FIG. 27C are evaluated. In additional embodiment, expression of one or more of the molecules listed in Table A is evaluated. The expression of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 of the molecules listed in Table A can be evaluated.

In yet other embodiments, the expression of one or more of SOX2 (e.g., GENBANK® Accession No. NM_003106), PAX6 (e.g., GENBANK® Accession No. NM_001604), RPE65 (e.g., GENBANK® Accession No. NM_000329), RDH5, (e.g., GENBANK® Accession No. NM_000329), TRPM1 (e.g., GENBANK® Accession No. NM_002420) and BEST1 (e.g., GENBANK® Accession No. NM_004183) is evaluated, all GENBANK® Accession information incorporated by reference as available on Jan. 31, 2013. In some embodiments, compared to undifferentiated iPSCs, iPSC-derived RPE expresses lower levels of neural progenitor factor SOX2 and much higher levels of RPE-specific genes PAX6, RPE65, RDH5, TRPM1, and BEST1.

The methods can include determining if an agent of interest increases the differentiation iPSCs into RPE cells. If the agent increases the differentiation into RPE cells, the expression of SOX2 is decreased and the expression of PAX6, RPE65, RDH5, TRPM1, and BEST1 is increased in the sample as compared to a control. In another embodiment, the expression of SOX2 is decreased and the expression of two, three, four or five of PAX6, RPE65, RDH5, TRPM1, and BEST1 are increased in the sample as compared to a control. The control can be a standard value or a sample contacted with an agent known not to increase the differentiation into RPE cells. The methods can also include determining if an agent of interest decreases the differentiation of iPSCs into RPE cells, and thus maintains the iPSCs in an undifferentiated state. If the agent decreases the differentiation into RPE cells, the expression of SOX2 is increased and the expression of PAX6, RPE65, RDH5, TRPM1, and BEST1 is decreased as compared to a control. In another embodiment, if the agent decreased differentiation into RPE cells, the expression of SOX2 is increased and the expression of two, three, four or five of PAX6, RPE65, RDH5, TRPM1, and BEST1 are decreased in the sample as compared to a control. The control can be a standard value or a sample construed with an agent known to increase differentiation into RPE cells. Exemplary non-limiting assays are disclosed in Example 8.

Nucleic acids can be detected by any method known in the art. In some examples, nucleic acids are isolated, amplified, or both, prior to detection. In an example, cells or a fraction thereof, such as purified nucleic acids, can be incubated with primers that permit the amplification of one or more of mRNAs, under conditions sufficient to permit amplification of such products. For example, the biological sample is incubated with primers or probes that can bind to one or more of the disclosed nucleic acid sequences (such as cDNA, genomic DNA, or RNA (such as mRNA) under high stringency conditions. The resulting hybridization can then be detected using methods known in the art.

The nucleic acid sample can be amplified. If a quantitative result is desired, a method is utilized that maintains or controls for the relative frequencies of the amplified nucleic acids. Methods of "quantitative" amplification are well known to those of skill in the art. For example, quantitative PCR involves simultaneously co-amplifying a known quantity of a control sequence using the same primers. This provides an internal standard that can be used to calibrate the PCR reaction. The array can then include probes specific to the internal standard for quantification of the amplified nucleic acid.

Suitable amplification methods include, but are not limited to, polymerase chain reaction (PCR) (see Innis et al., *PCR Protocols, A guide to Methods and Application*, Academic Press, Inc. San Diego, 1990), ligase chain reaction (LCR) (see Wu and Wallace, *Genomics* 4:560, 1989; Landegren et al., *Science* 241:1077, 1988; and Barringer, et al., *Gene* 89:117, 1990), transcription amplification (Kwoh et al., *Proc. Natl. Acad. Sci. U.S.A.* 86:1173, 1989), and self-sustained sequence replication (Guatelli et al., *Proc. Nat. Acad. Sci. U.S.A.* 87:1874, 1990). In one embodiment, the sample mRNA is reverse transcribed with a reverse transcriptase and a primer consisting of oligo dT and a sequence encoding the phage T7 promoter to provide single stranded DNA template (termed "first strand"). The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA.

Methods of in vitro polymerization are well known to those of skill in the art (see, for example, Sambrook, supra; Van Gelder et al., *Proc. Natl. Acad. Sci. U.S.A.* 87:1663-1667, 1990). The direct transcription method provides an antisense (aRNA) pool. Where antisense RNA is used as the target nucleic acid, the oligonucleotide probes provided in the array are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Finally, where the nucleic acid pool is double stranded, the probes may be of either sense as the target nucleic acids include both sense and antisense strands.

In one embodiment, the hybridized nucleic acids are detected by detecting one or more labels attached to the sample nucleic acids. The labels can be incorporated by any of a number of methods. In one example, the label is simultaneously incorporated during the amplification step in the preparation of the sample nucleic acids. Thus, for example, polymerase chain reaction (PCR) with labeled primers or labeled nucleotides will provide a labeled amplification product. In one embodiment, transcription amplification, as described above, using a labeled nucleotide (such as fluorescein-labeled UTP and/or CTP) incorporates a label into the transcribed nucleic acids. In some embodiments, a multiplex PCR assay is utilized. The assay can be a multiplex assay.

An exemplary assay for assessing expression of gene expression is shown in FIG. 27. In this assay, a first probe specific to a first gene of interest is attached to a first detectable bead. Addition probes can be included in the assay, such that it is a multiplex assay. Thus, the assay an include a second probe specific to a second gene of interest attached to a second detectable label, a third probe specific to a third gene of interest attached to a third detectable label, etc. In some embodiments a single well can include 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 probes, each specific to a different gene of interest, and each attached to a unique detectable label. In this manner, the expression of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 genes can be evaluate in each assay. Exemplary probes are shown in FIG. 27B.

Alternatively, a label may be added directly to the original nucleic acid sample (such as mRNA, polyA mRNA, cDNA, etc.) or to the amplification product after the amplification is completed. Means of attaching labels to nucleic acids are well known to those of skill in the art and include, for example, nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use include any composition detectable by spectroscopic, photochemical, biochemical, immunochemical, electrical, optical or chemical means. Useful labels include biotin for staining with labeled streptavidin conjugate, magnetic beads (for example DYNABEADS™), fluorescent dyes (for example, fluorescein, Texas red, rhodamine, green fluorescent protein, and the like), radiolabels (for example, $^3$H, $^{125}$I, $^{35}$S, $^{14}$C, or $^{32}$P), enzymes (for example, horseradish peroxidase, alkaline phosphatase and others commonly used in an ELISA), and colorimetric labels such as colloidal gold or colored glass or plastic (for example, polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are also well known. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The label may be added to the target (sample) nucleic acid(s) prior to, or after, the hybridization. So-called "direct labels" are detectable labels that are directly attached to or incorporated into the target (sample) nucleic acid prior to hybridization. In contrast, so-called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected (see *Laboratory Techniques in Biochemistry and Molecular Biology*, Vol. 24: *Hybridization With Nucleic Acid Probes*, P. Tijssen, ed. Elsevier, N.Y., 1993).

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus, specificity of hybridization is reduced at lower stringency. Conversely, at higher stringency (e.g., higher temperature or lower salt) successful hybridization requires fewer mismatches.

One of skill in the art will appreciate that hybridization conditions can be designed to provide different degrees of stringency. In a one embodiment, hybridization is performed at low stringency in this case in 6×SSPE-T at 37° C. (0.005% Triton X-100) to ensure hybridization and then subsequent washes are performed at higher stringency (e.g., 1×SSPE-T at 37° C.) to eliminate mismatched hybrid duplexes. Successive washes may be performed at increasingly higher stringency (e.g., down to as low as 0.25× SSPE-T at 37° C. to 50° C.) until a desired level of hybridization specificity is obtained. Stringency can also be increased by addition of agents such as formamide Hybridization specificity may be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in one embodiment, the wash is performed at the highest stringency that produces consistent results and that provides a signal intensity greater than approximately 10% of the background intensity. Thus, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest. These steps have been standardized for commercially available array systems.

Methods for evaluating the hybridization results vary with the nature of the specific probe nucleic acids used as well as the controls provided. In one embodiment, simple quantification of the fluorescence intensity for each probe is determined. This is accomplished simply by measuring probe signal strength at each location (representing a different probe) on the array (for example, where the label is a fluorescent label, detection of the amount of florescence (intensity) produced by a fixed excitation illumination at each location on the array). Comparison of the absolute intensities of an array hybridized to nucleic acids from a "test" sample (such as from a patient treated with a therapeutic protocol) with intensities produced by a "control" sample (such as from the same patient prior to treatment with the therapeutic protocol) provides a measure of the relative expression of the nucleic acids that hybridize to each of the probes.

Changes in expression detected by these methods for instance can be different for different therapies, for example, and may include increases or decreases in the level (amount) or functional activity of such nucleic acids, their expression or translation into protein, or in their localization or stability. An increase or a decrease can be, for example, about a 1-fold, 2-fold, 3-fold, 4-fold, 5-fold, change (increase or decrease) in the expression of a particular nucleic acid.

In some examples, the effectiveness of an agent, or the production of RPE cells, or the identification of RPE cells, is performed by applying isolated nucleic acid molecules to an array in which the isolated nucleic acid molecules are obtained from a biological sample including RPE cells, such as following treatment with an agent of interest. In such example, the array includes oligonucleotides complementary to the nucleic acids disclosed above.

In an example, the isolated nucleic acid molecules are incubated with the array including oligonucleotides complementary to nucleic acid molecules disclosed above for a time sufficient to allow hybridization between the isolated nucleic acid molecules and oligonucleotide probes, thereby forming isolated nucleic acid molecule:oligonucleotide complexes. The isolated nucleic acid molecule:oligonucleotide complexes are then analyzed to determine if expression of the isolated nucleic acid molecules is altered. In such example, an agent is evaluated to see if it affects expression of the molecule as compared to a control (such cells not contacted with the agent) or reference value.

A gene expression profile is disclosed herein that can be used to identify the effectiveness of an agent for producing RPE cells, or for identifying an RPE cell. In an example, the gene expression profile includes at least two of the molecules listed above, such as at least 5, at least 7, at least 10, at least 20, at least 30, at least 40, or all of the molecules that are listed. In some examples, the gene expression profile includes at least 2, at least 5, at least 7, at least 10, at least 20, at least 25, at least 25, at least 30, at least 35 or at least 40 molecules (for example, 2, 3, 4, 5, 6, 7, 8, 9, 10, 11, 12, 13, 14, 15, 16, 17, 18, 19, 20, 22, 24, 25, 26, 27, 28, 29, 30, 31, 32, 33, 34, 35, 36, 37, 38, 39, 40 or all 41 molecules). In one specific non-limiting example, the gene expression profile includes of MITF, PAX6, LHX2, TFEC, CDH1, CDH3, CLDN10, CLDN16, CLDN19, BEST1, TIMP3, TRPM1, TRPM3, TTR, VEGFA, CSPG5, DCT, TYRP1, TYR, SILV, SILL MLANA, RAB27A, OCA2, GPR143, GPNMB, MYO6, MYRIP, RPE65, RBP1, RBP4, RDH5, RDH11, RLBP1, MERTK, ALDH1A3, FBLN1, SLC16A1, KCNV2, KCNJ13, and CFTR.

In additional embodiments, the gene expression profile includes at least 2, 5, 10, 15, 20, 25, 30, 35, 40, 45, 50, 55, 60, 65, 70, 80, 85, 90, 95 or all 96 of the miRNAs listed in Table 2. In one specific, non-limiting example, the gene expression profile includes miR204 and miR211. In further embodiments, the gene expression profile includes at least 5, 10, 15, 20, 25, 30, 35, 40, 45, 50, 55, 60, 65, 70, 75, 80, 85, 90, 95, 100, 105, 110, 115, 120, 125, 130, 135, or all of the markers listed in Table 1 and Table 2. This expression profile can be used to detect RPE cells, and/or confirm that a cell is an RPE cell.

As an alternative to analyzing the sample for the presence of nucleic acids, the presence of proteins can be determined. Proteins can be detected by any method known in the art. In some examples, proteins are purified prior to detection. For example, the effect of an agent can be determined by incubating the cells, such as iPSCs, embryoid bodies, or RPE cells with one or more antibodies that specifically binds to one of the molecules listed above, for an amount of time sufficient to form an immune complex, in order to detect expression. The primary antibody can include a detectable label. For example, the primary antibody can be directly labeled, or the sample can be subsequently incubated with a secondary antibody that is labeled (for example with a fluorescent label). The label can then be detected, for example by microscopy, ELISA, flow cytometry, or spectrophotometry. In another example, the biological sample is analyzed by Western blotting for the presence or absence of the specific molecule. In other examples, the biological sample is analyzed by mass spectrometry for the presence or absence of the specific molecule. In other examples, a first antibody that specifically binds a molecule listed above is unlabeled and a second antibody or other molecule that can specifically binds the first antibody is labeled. As is well known to one of skill in the art, a second antibody is chosen that is able to specifically bind the specific species and class of the first antibody. For example, if the first antibody is a human IgG, then the secondary antibody can be an anti-human-IgG. Other molecules that can bind to antibodies include, without limitation, Protein A and Protein G, both of which are available commercially. The secondary antibody is incubated with the cells for a sufficient time to form an immune complex.

Suitable labels for the antibody or secondary antibody include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary magnetic agent is gadolinium, and non-limiting exemplary radioactive labels include $^{125}$I, $^{131}$I, $^{35}$S or $^{3}$H.

In an alternative example, proteins can be assayed in a biological sample by a competition immunoassay utilizing protein standards (molecules) labeled with a detectable substance and unlabeled antibody that specifically bind to the desired molecule. In this assay, the cells, the labeled molecule standard and the antibody that specifically binds to the molecule are combined and the amount of labeled molecule standard bound to the unlabeled antibody is determined. The amount of the molecule in the biological sample is inversely proportional to the amount of labeled molecule standard bound to the antibody that specifically binds the molecule.

In yet other embodiments the resting potential of the cells is assessed. In some embodiments, a resting potential of about −50 to about −60 mV, and a fluid transport rate of about 5 to about 10 µl cm$^{-2}$h$^{-1}$ indicates that the cells is an RPE cell. In additional embodiments, the production of cells that express MITF, PAX6, LHX2, TFEC, CDH1, CDH3, CLDN10, CLDN16, CLDN19, BEST1, TIMP3, TRPM1, TRPM3, TTR, VEGFA, CSPG5, DCT, TYRP1, TYR, SILV, SILL MLANA, RAB27A, OCA2, GPR143, GPNMB, MYO6, MYRIP, RPE65, RBP1, RBP4, RDH5, RDH11, RLBP1, MERTK, ALDH1A3, FBLN1, SLC16A1, KCNV2, KCNJ13, and CFTR, express miR204 and miR211, and have a resting potential of about −50 to about −60 mV. In certain embodiments, an increase in the number of cells with these features, following contact with the agent of interest, indicates that the agent increases the proliferation and/or differentiation of RPE cells.

In additional embodiments, the fluid transport of the cells is determined. Fluid transport of cells can be measured using a capacitance probe. In some embodiments, cells grown as a monolayer tissue are mounted in a modified Üssings chamber and probe that measure capacitance is used. If the volume of fluid on either side of the cell layer changes, capacitance of the probes changes. This can be used to calculated the volume change and the fluid flow. In some examples, a fluid transport rate of about 5 to about 15 µl $cm^{-2}h^{-1}$ such as a fluid transport rate of about 5 to about 10 µl $cm^{-2}h^{-1}$, indicates that the cell is an RPE cell.

The ability of cells to reversibly increase fluid flow by either ATP treatment of the apical side or IFN gamma treatment of the basal side can be measured. Both of these responses can be inhibited by inhibiting chloride channels on the basal side. These properties can be used to determine that the cell as an RPE cell.

In further examples, the polarization of the cell is assessed. Thus, in some embodiments, selective $CO_2$ permeability of the apical surface of RPE cells is measured. Photoreceptors secrete high concentrations of $CO_2$ towards the apical surface (Adijanto et al., J Gen Physiol. 2009 June; 133(6):603-22). Therefore, this surface has been evolutionarily selected to trap $CO_2$. This function can be measured in vitro by changing $CO_2$ concentrations in the apical or the basal baths of RPE cells, such as RPE cells growing in transwells. If the RPE cells trap $CO_2$, they respond by a reduction in pH, which can be measured by a ratio-metric dye.

In one specific non-limiting example, a RPE monolayer grown on a porous polyester membrane is incubated in Ringer solution containing 8 µM BCECF-AM. After incubation with BCECF-AM, the tissue was incubated in control (5% $CO_2$) Ringer for another 30 minutes before mounting in a modified Üssing chamber. The Üssing chamber is mounted on the stage of an axiovert-200 microscope (Carl Zeiss, Inc.) equipped with a 20× objective. The RPE is continuously perfused with Ringer solution (equilibrated with 5% $CO_2$ at 36.5° C.). Excitation photons (440/480 nm) are generated by a xenon light source, and the specific wavelengths are selected with a monochromator (Polychrome IV; Photonics). The emission fluorescence signals are captured with a photomultiplier tube (Thorn EMI). pHi calibrations are performed by perfusing high-K calibration solutions (at pH 6.8, 7.2, and 7.6) containing 20 µM nigericin into both solution baths.

In some embodiments, changes in the electric properties of RPE cells can be measured. In some specific non-limiting examples, RPE cells are grown as a monolayer on a porous polyester membrane. Transepithelial potential is measured with a pair of calomel electrodes in series with Ringer solution agar (4% wt/vol) bridges placed in the apical and basal baths of the Üssing chamber. The TEP recordings are moving averages of 3 seconds. The transepithelial resistance was calculated from Ohm's law.

$$R_T = \frac{\Delta TEP \cdot Area}{Current}.$$

When light hits the photoreceptors in RPE cells, the photoreceptors depolarize by closing potassium (K) channels (see, Millers et al., (ed). Encyclopedia of the eye, ELSEVIER). This reduces the concentration of K-ions in between photoreceptors and RPE (subretinal space) from 5 mM to 1 mM. RPE cells respond to this changing concentration by hyperpolarizing and opening their K channels to increase the subretinal K concentration back to 5 Mm. A range of 1-5 mM indicates the cell is an RPE cell.

In further embodiments, the production of cells that express MITF, PAX6, LHX2, TFEC, CDH1, CDH3, CLDN10, CLDN16, CLDN19, BEST1, TIMP3, TRPM1, TRPM3, TTR, VEGFA, CSPG5, DCT, TYRP1, TYR, SILV, SILL MLANA, RAB27A, OCA2, GPR143, GPNMB, MYO6, MYRIP, RPE65, RBP1, RBP4, RDH5, RDH11, RLBP1, MERTK, ALDH1A3, FBLN1, SLC16A1, KCNV2, KCNJ13, and CFTR, express miR204 and miR211, have a resting potential of about −50 to about −60 mV, and have a fluid transport rate of about 5 to about 10 µl $cm^{-2}h^{-1}$ i. In certain embodiments, an increase in the number of cells with these features, following contact with the agent of interest, indicates that the agent increases the proliferation and/or differentiation of RPE cells.

The disclosure is illustrated by the following non-limiting Examples.

EXAMPLES

Example 1

Exemplary Materials and Methods for Differentiation of Human Induced Pluripotent Stem Cells (hiPSC) into Retinal Pigment Epithelial Cells (RPE)

Maintaining and Passaging hiPSC

Grow hiPSC on g-irradiated mouse embryo fibroblasts (MEFs) in human embryonic stem (hES) media+basic Fibroblast Growth Factor (bFGF-added fresh).

Feed hiPSC daily with hES media+bFGF (added fresh) to a final concentration of 10 ng/ml-1.5 ml/well of P6.

When hiPSC colonies are 80% confluent, split them (1:6) onto new MEFs for continued passage (eg. six wells of a P6 plate expanded into six-P6 plates)

Aspirate hES media

Wash 1× with PBS

Add 1 ml CTK and place in +37 C incubator for 10 min (time varies with iPSC line)

Aspirate CTK (make sure colonies are still adhered to the plate)

Add 2 ml PBS without Ca/Mg and place in +37 C incubator for 5 min

Aspirate PBS and add another 2 ml of PBS and place in +37 C incubator for 5 min

Aspirate PBS (MEFs are preferentially lifted in the PBS)

Add 1 ml of hES media+(10 ng/ml) bFGF (added fresh)+(10 uM) Rock Inhibitor (RI) (added fresh) to each well of P6

Using a 1 ml pipetman, gently pipet up and down to remove colonies from plate (try not to generate single cells); transfer cells to a clean tube; add another 1 ml hES media+bFGF+RI to each well, turn plate, and pipet up and down to loosen remaining colonies; transfer cells to same tube; add the appropriate volume of hES+bFGF+RI media to cells (6-P6 plates will require 54 mls)

Aspirate Feeder media from MEF plates

Distribute 1.5 mls cells/well of P6

(Reh et al., 2010, Methods Mol. Biol.; Takahashi et al., 2001 PLoS One)

When hiPSC colonies are 70% confluent, prepare embryoid bodies (EBs)

Aspirate hES media

Wash 1× with PBS

Add 1 ml of 1 mg/ml collagenase/well of P6 and put in +37 C incubator for 15 min Aspirate collagenase and add 1 ml DMEM Scrape colonies gently with cell lifter (Corning#3008) being careful not to break the colonies into single cells Transfer contents of all 6 wells to a 15 ml conical tube with a 1 ml pipetman Add another 1 ml of DMEM to each well, turn the plate around, and gently scrape the remaining colonies with the cell lifter; transfer contents of all 6 wells to the same tube (~12 ml DMEM/tube).

Let the cell aggregates settle to the bottom of the tube (~2-5 min or until the media is clear).

Aspirate the supernatant (contains the single cell and MEFs) and wash the cell aggregate with 10 ml DMEM; pipet up and down with 10 ml pipet 3-5 times to break up aggregates-if they are too big (will depend on size of starting iPSC colony); break them into smaller clumps. Smaller cell clumps that contain between 200-500 cells make RPE with a higher efficiency, as compared to larger clumps. Larger clumps when plated make 3-dimensional structures that do not form RPE at a high efficiency.

Let the cell aggregates settle to the bottom of the 15 ml conical tube.

Aspirate the supernatant and resuspend the cell aggregate in desired volume of Retinal Induction Medium (RIM)+ Rock inhibitor (10 uM) (usually 8 ml of RIM/15 ml conical tube). Reduction of the amount of knockout serum replacement (KSR) from 10% to 1.5% increased RPE differentiation efficiency.

Transfer aggregates in RIM+RI to a low attachment dish (Corning#326210 cm low attachment plate) where they will form EBs within 24 hours 48 hours later, evenly distribute EBs onto plates coated with MATRIGEL®. 150-250 EBs/well of a 6-well plate differentiate into RPE with a higher efficiency as compared to more than 250 EBs/well. Higher number of EBs makes too confluent cultures and cells do not differentiate into RPE at a high efficiency.

Transfer EBs to 15 ml conical tube and let settle (~2-5 min).

Aspirate supernatant.

Add appropriate volume of Retinal Differentiation Media (RDM) to EBs.

Aspirate the matrigel from each well and wash 1× with PBS.

Distribute equal amount of EBs to each matrigel-coated well and swirl plate to achieve an even distribution of EBs on the well's surface (usually EBs from 1-well of a P6-plate can be plated into 2-wells of a P6-plate).

Change media every other day for 3 weeks (eg. Mon, Wed, Fri)

This protocol significantly increased the expression of genes responsible for RPE fate induction and have increased the efficiency of RPE differentiation. The elements of this protocol are a reduced conc. of KSR (1.5%), no FGF, addition of DKK1 (100 ng/ml), and PD 0325901 (0.1 uM), using NOGGIN at 50 ng/ml. Inhibition of both WNT (by DKK1) and BMP (by NOGGIN) pathways promotes rostral neuroectoderm formation, which can also make eye cells. Inhibition of FGF signaling (by PD 0325901) suppressed retinal fate and induces RPE fate from rostralized neuroectoderm.

Transfer cells to Retinal Media (RM) plus Nicotinamide, Activin, and Wnt3a (NAW). Change media every other day (eg. Mon, Wed, and Fri) for 3 weeks.

Addition of WNT3a has also significantly increased the RPE differentiation efficiency. Activation of canonical WNT signaling increases the expression of MITF and PAX6, two RPE inducing transcription factors and thus increases RPE differentiation efficiency.

Transfer cells to 5% Retinal Pigmented Epithelial (RPE) Media containing WNT5a (100 ng/ml), DKK1 (100 ng/ml), SU5402 (10 uM), CYCLOPAMINE (5 uM). WNT5a and DKK1 inhibit canonical WNT signaling, thereby reducing PAX6 and MITF expression and maturing RPE cells. SU5402 inhibits FGF signaling and CYCLOPAMINE inhibits Sonic signaling. Both FGF and Sonic signaling are associated with retinal induction. Therefore, inhibiting these pathways promotes RPE differentiation. Change media every other day (for example: Monday, Wednesday, and Friday). Within a week or two several pigmented colonies appear. At this point, cells can be seeded onto transwells in 5% RPE medium for functional analysis.

Cells are maintained for 8 weeks onto these transwells, where they continue to mature. At 8 weeks fully functional and polarized monolayers of cells on transwells are harvested for the expression of RPE-signature genes and miRNAs. Gene expression is measured using qRT-PCR assays.

To Prepare MEF Plates:

Coat 4-P6 plates with 0.1% gelatin and let sit at room temp for at least 15 min

Thaw 1 vial of MEFs (Mt. Sinai Stem Cell #GSC-6001G; 5 million cells/vial) and resuspend in 9 ml Feeder Cell Media Spin cells 1.2K for 5 min; aspirate supernatant and resuspend pellet in 36 ml Feeder Cell Media Aspirate gelatin from wells and distribute 1.5 ml MEFs/ well of P6

MEFs are good for 2 weeks and do not have to change media

To Prepare MATRIGEL® Plates:

Let matrigel (BD #356230) thaw overnight on ice at +4 C.

Add equal volume of DMEM to thawed matrigel on ice the next day and mix well.

Incubate overnight on fresh ice at +4 C.

Mix the next day and aliquot 0.4 ml/eppendorf tube (=1:2) and freeze at −80 C.

Thaw a tube of diluted (1:2) matrigel on ice (or let it thaw over-night at +4 C); keep the aliquots on ice while working with them.

Dilute the matrigel 1:25 in cold DMEM media (10 ml media+0.4 ml MATRIGEL® (1:2)).

To coat a tissue culture plate, place matrigel on the dish and shake to distribute evenly (for example 1 ml/well of a P6).

Let the plate sit at room temperature for 1 h to overnight with very gentle shaking; chill the plates at +4 C before use.

If the plates are not used immediately, wrap them in foil and keep at +4 C for 1-2 days.

Reagents

Feeder Cell Media (500 ml)

| | |
|---|---|
| DMEM (High Glucose) (Invitrogen#11960-077) | 435 ml |
| Heat-Inactivated Fetal Bovine Serum (FBS) (Invitrogen#10082147) | 50 ml |

| | |
|---|---|
| Pen/Strep (Gibco#15140) | 5 ml |
| Glutamine (200 mM) (Gibco#25030) | 5 ml |
| Na Pyruvate (100 mM) (Gibco#11360) | 5 ml |

Filter Media
hES Media (500 ml)

| | |
|---|---|
| DMEM/F12 (1:1) (Invitrogen#11320-033) | 385 ml |
| Knockout Serum Replacement (Invitrogen #10828-028) | 100 ml |
| Non-Essential Amino Acids (Gibco#11140) | 5 ml Pen/Strep |
| (Gibco#15140) | 5 ml |
| Glutamine (200 mM) (Gibco#25030) | 5 ml |
| b-Mercaptoethanol (55 mM in PBS) (Gibco#21985) | 0.5 ml |

Filter Media.
Add bFGF (RD Systems#233-FB; final concentration of 10 ng/ml; make 10 ug/ml stock and dilute 1:1000 in hES) to hES media immediately before use. When passaging hiPSC, also add RI to hES media immediately before use.
CTK:
  5 ml 0.25% Trypsin+5 ml 1 mg/ml collagenase IV+0.5 ml 0.1M CaCl2+10 ml KSR (knockout serum)+30 ml DMEM-F12, store @-20 C
  Rock inhibitor from EMD In solution Y27632 cat #688001—10 mM stock solution
Retinal Induction Medium (RIM) (500 ml)

| | |
|---|---|
| DMEM/F12 (1:1) (Invitrogen#11320-033) | 500 ml |
| Knockout Serum Replacement (Invitrogen #10828-028) | 7.5 ml |
| Non-Essential Amino Acids (Gibco#11140) | 5 ml |
| Pen/Strep (Gibco#15140) | 5 ml |
| Sodium Pyruvate (100 mM) (Gibco#11360) | 5 ml |
| N2 Supplement 1x (Gibco#17502-048) | 5 ml |
| B27 Supplement 1x (Gibco#17504-044) | 10 ml |
| CK1-7 Dihydrochloride (5 mM) (Sigma#C0742) | 50 ul |
| SB 431542 hydrate (5 mM) (Sigma#S4317) | 50 ul |
| Noggin (250 ug/ml) (RD Systems#6057-NG) | 2 ul |
| IGF-1 (100 ug/ml) (RD Systems#291-G1) | 5 ul |
| Ascorbic Acid (5 mg/ml) (Sigma#A4544-25G) | 5 ml |

Retinal Differentiation Medium (RDM) (500 ml)

| | |
|---|---|
| DMEM/F12 (1:1) (Invitrogen#11320-033) | 500 ml |
| Knockout Serum Replacement (Invitrogen #10828-028) | 7.5 ml |
| Non-Essential Amino Acids (Gibco#11140) | 5 ml |
| Pen/Strep (Gibco#15140) | 5 ml |
| Sodium Pyruvate (100 mM) (Gibco#11360) | 5 ml |
| N2 Supplement 1x (Gibco#17502-048) | 5 ml |
| B27 Supplement 1x (Gibco#17504-044) | 10 ml |
| CK1-7 (5 mM) (Sigma#C0742) | 0.5 ml |
| DKK1 (100 ug/ml) (R&D Systems) | 0.5 ml |
| SB-431542 (5 mM) (Sigma#S4317) | 0.5 ml |
| Noggin (250 ug/ml) (RD Systems#6057-NG) | 0.1 ml |
| IGF-1(100 ug/ml) (RD Systems#291-G1) | 50 ul |
| Ascorbic Acid (5 mg/ml) (Sigma#A4544-25G) | 5 ml |
| PD 0325901 (1 mM) (Tocris#4192) | 0.5 ml |
| NO FGF | |

Retinal Medium (RM)+Nicotinamide, Activin, and Wnt3a (NAW) (500 ml)

| | |
|---|---|
| DMEM/F12 (1:1) (Invitrogen#11320-033) | 500 ml |
| Knock out Serum Replacement (Invitrogen #10828-028) | 50 ml |
| Non-Essential Amino Acids (Gibco#11140) | 5 ml |
| Pen/Strep (Gibco#15140) | 5 ml |
| Sodium Pyruvate (100 mM) (Gibco#11360) | 5 ml |
| N2 Supplement 1x (Gibco#17502-048) | 5 ml |
| B27 Supplement 1x (Gibco#17504-044) | 10 ml |
| Nicotinamide (Sigma#N0636) (1M) | 5 ml |
| Activin (RD Systems#338-AC) (50 ug/ml) | 1.5 ml |
| Wnt3a (RD Systems#5036-WN) (200 ug/ml) | 250 ul |

Rock inhibitor from EMD In solution Y27632 cat #688001
5% Retinal Pigmented Epithelial (RPE) Media

| | |
|---|---|
| MEM_modified (M-4526) | 500 ml |
| N1 supplement (N-6530) | 5 ml |
| Glutamax, Penicillin-streptomycin (G-1146) | 5 ml |
| Non essential amino acids (M-7145) | 5 ml |
| Taurine (T-0625) | 125 mg |
| Hydrocortisone (H-0396) | 10 ug |
| Triiodo-thyronin (T-5516) | 0.0065 ug |
| Fetal bovine serum, heat inactivated | 1% or 5% or 15% |

The use of different amounts of Knockout Serum Replacement (KOSR) in the media used for the first three weeks of the differentiation protocol was assessed. Retinal differentiation media (RDM), showed differential effects on cell pigmentation. iPSC were incubated in high KOSR (10%) resulted in a smaller number of pigmented cells compared to the use of lesser amounts of KOSR (1.5%). After culture in 10, 5.25, or 1.5% KOSR, the cells were shifted to NAW containing 1.5% KOSR for 3 weeks and photographed at 16 weeks (see FIG. 34A and FIG. 34B).

Example 2

Reporter iPSC Cell Lines

Figure 1:
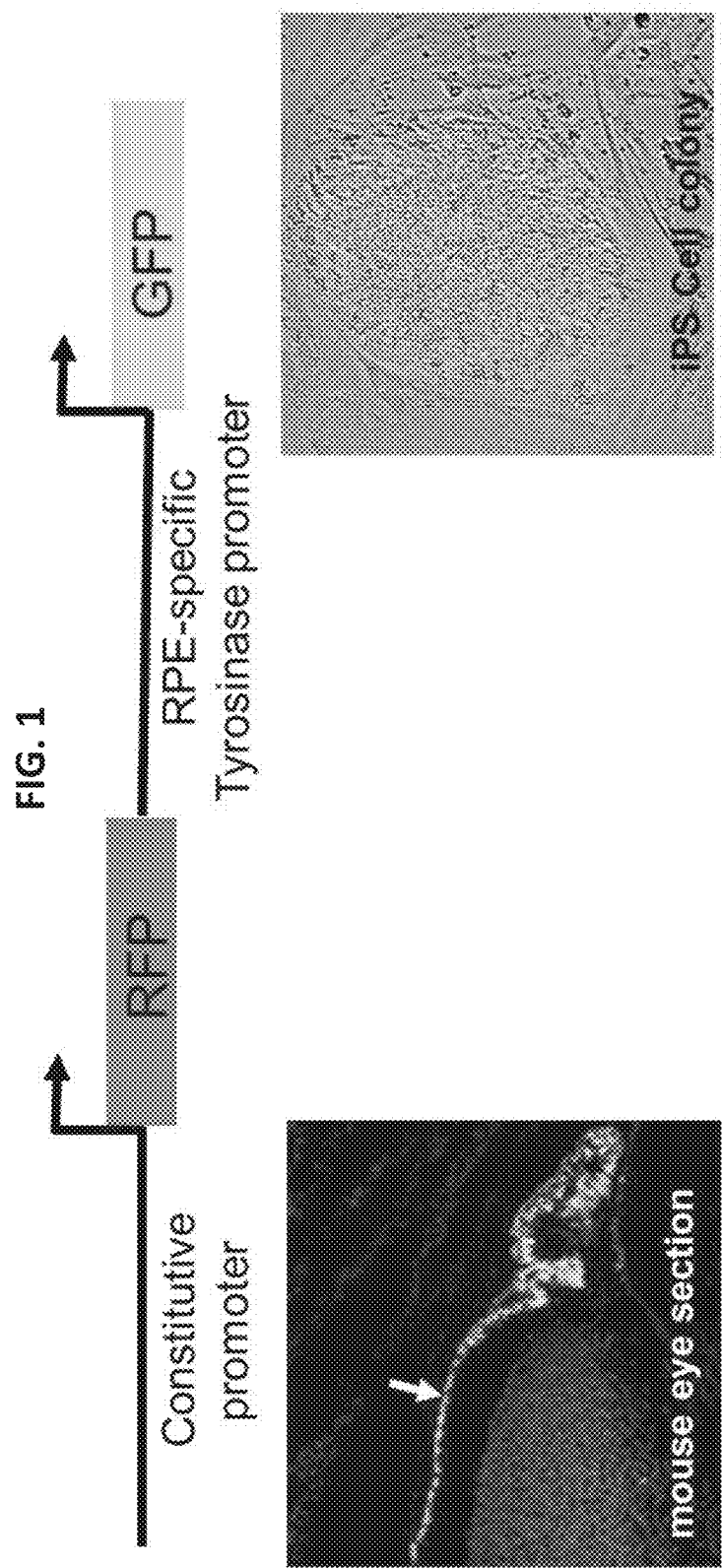
FIG. 1 is a schematic diagram of the RPE-specific construct, which includes a constitutive promoter operably linked to a marker (for example, red fluorescent protein, RFP) and the RPE-specific tyrosinase promoter operably linked to a second marker (for example, green fluorescent protein, GFP). Digital images of the results achieved are also shown. The RPE-specific promoter/enhancer-GFP construct was first tested in a transgenic mouse. RPE-specific GFP expression (left image) was achieved. This construct was then combined with a constitutive RFP and transduced into iPSCs. At the iPSC stage only RFP is expressed (right image). This construct can be used to produce an iPSC line expressing RPE specific GFP.
Figure 2:
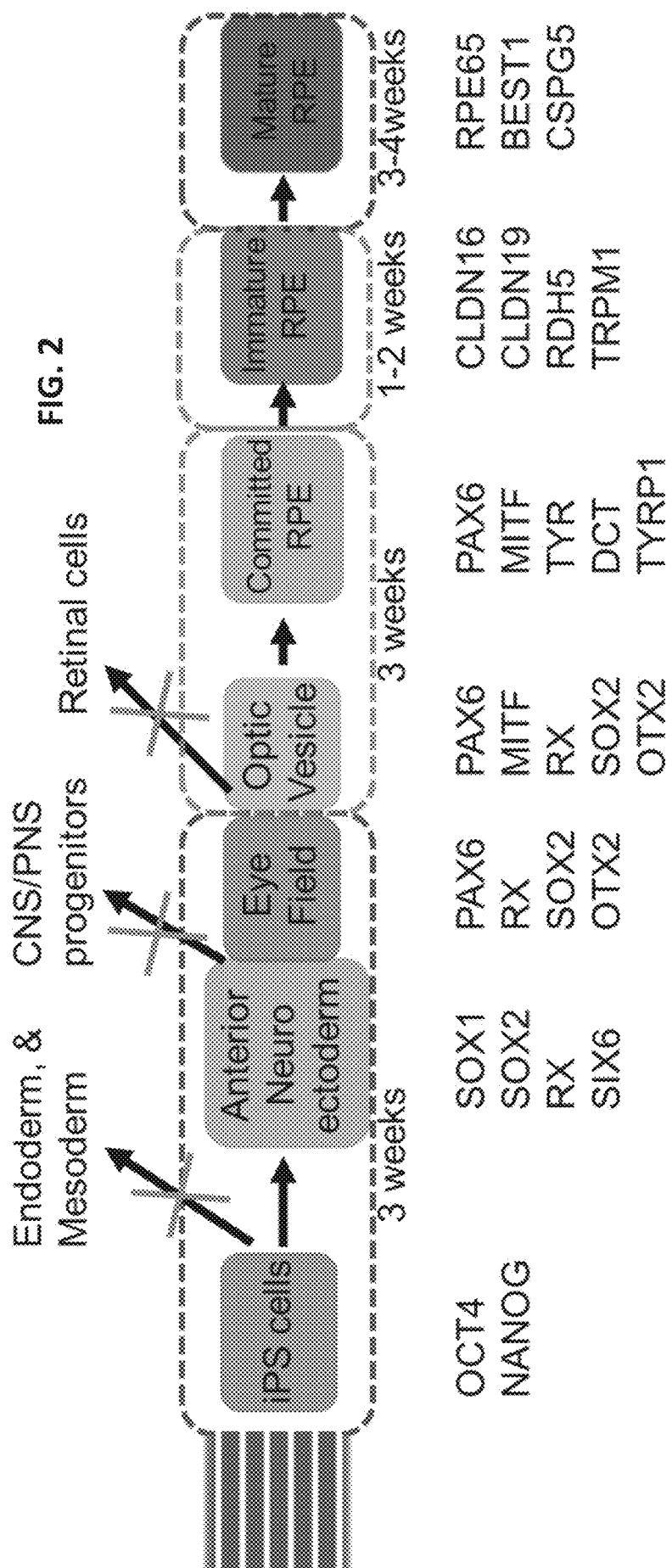
FIG. 2 is a schematic diagram of the steps in differentiation of RPE from human iPSCs. The protocol was optimized to obtain RPE cells with high efficiency, while inhibiting other lineages. Markers for the different stages are shown.
Figure 3:
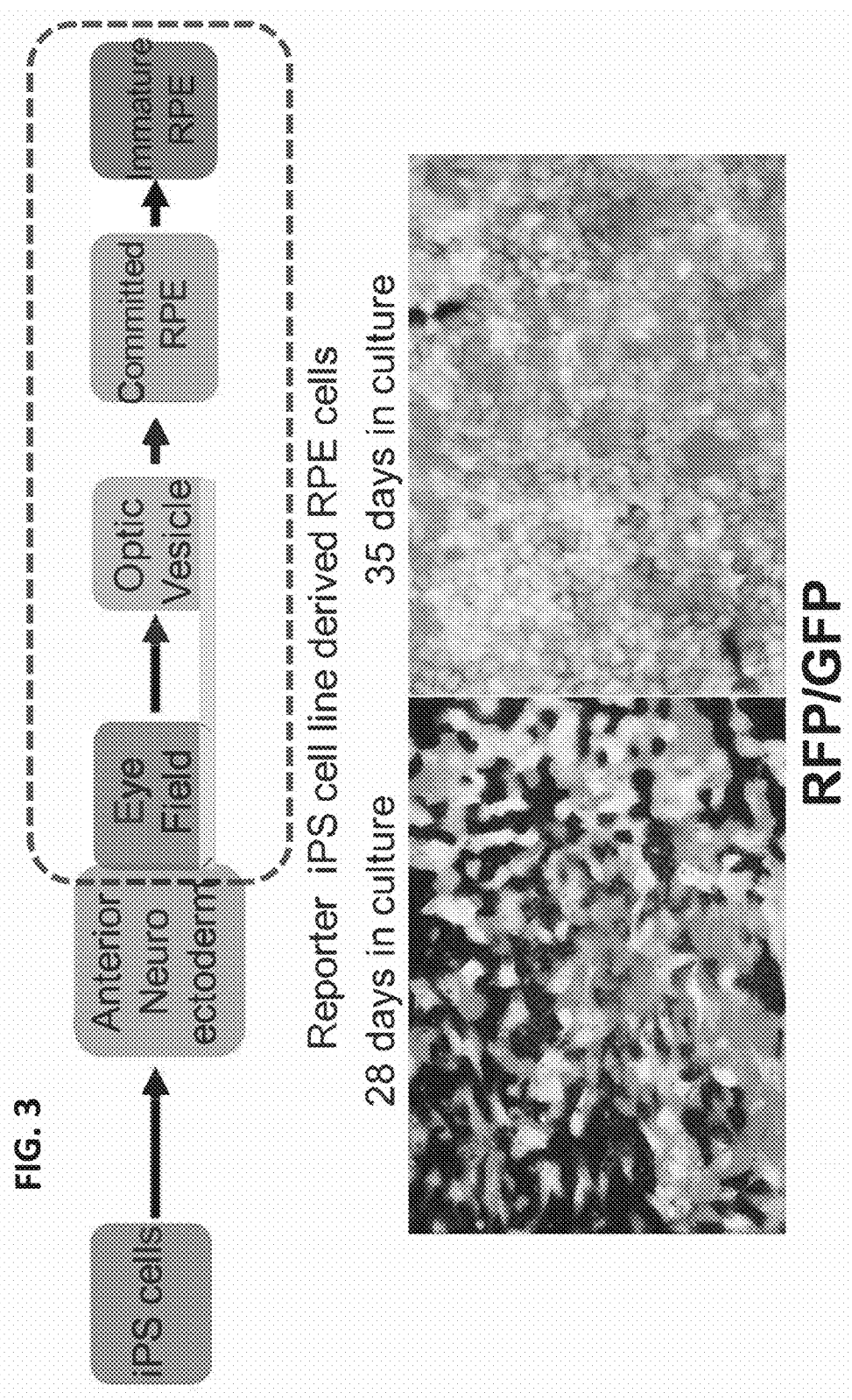
FIG. 3 is a schematic diagram and digital images of RPE-Specific GFP Expression in the Reporter iPSC line. GFP positive cells appear when cells reach committed RPE stage, which begins 4 weeks after differentiation begins. GFP positive cells acquire epithelial character and begin to pigment in one more week. The expression of reporter after 28 and 35 days in culture is shown.

To optimize the protocol for iPSC to RPE differentiation, a reporter iPSC line was created. This reporter line constitutively expresses a red fluorescent protein, whose expression is controlled by ubiquitin gene promoter. The reporter iPSC line also expresses a green fluorescent protein (GFP), specifically when differentiated in to RPE lineage (FIG. 1-3). The RPE-specific enhancer of the gene Tyrosinase controls GFP expression in this iPSC line (FIG. 1). The first goal was to confirm that the GFP expression truly represents RPE lineage. To achieve this, iPSC line were differentiated using published differentiation protocols and characterized those differentiated cells using molecular and physiological assays. These assays are disclosed in FIGS. 22-24. FIG. 2 describes a simple schematic drawing of iPSC-RPE differentiation. When the reporter iPSC were differentiated into RPE, approximately 28 days into differentiation, GFP positive cells are present (FIG. 3A). These cells go on to form an epithelial monolayer with characteristic polygonal RPE morphology and continue to express GFP (FIG. 3B). GFP positive and negative cells were sorted by flow cytometry and the expression of several RPE-specific genes was analyzed, shown in FIG. 4. The results show that GFP positive cells express RPE-specific markers at much higher levels as compared to GFP negative cells from the same dish.

Figure 5:
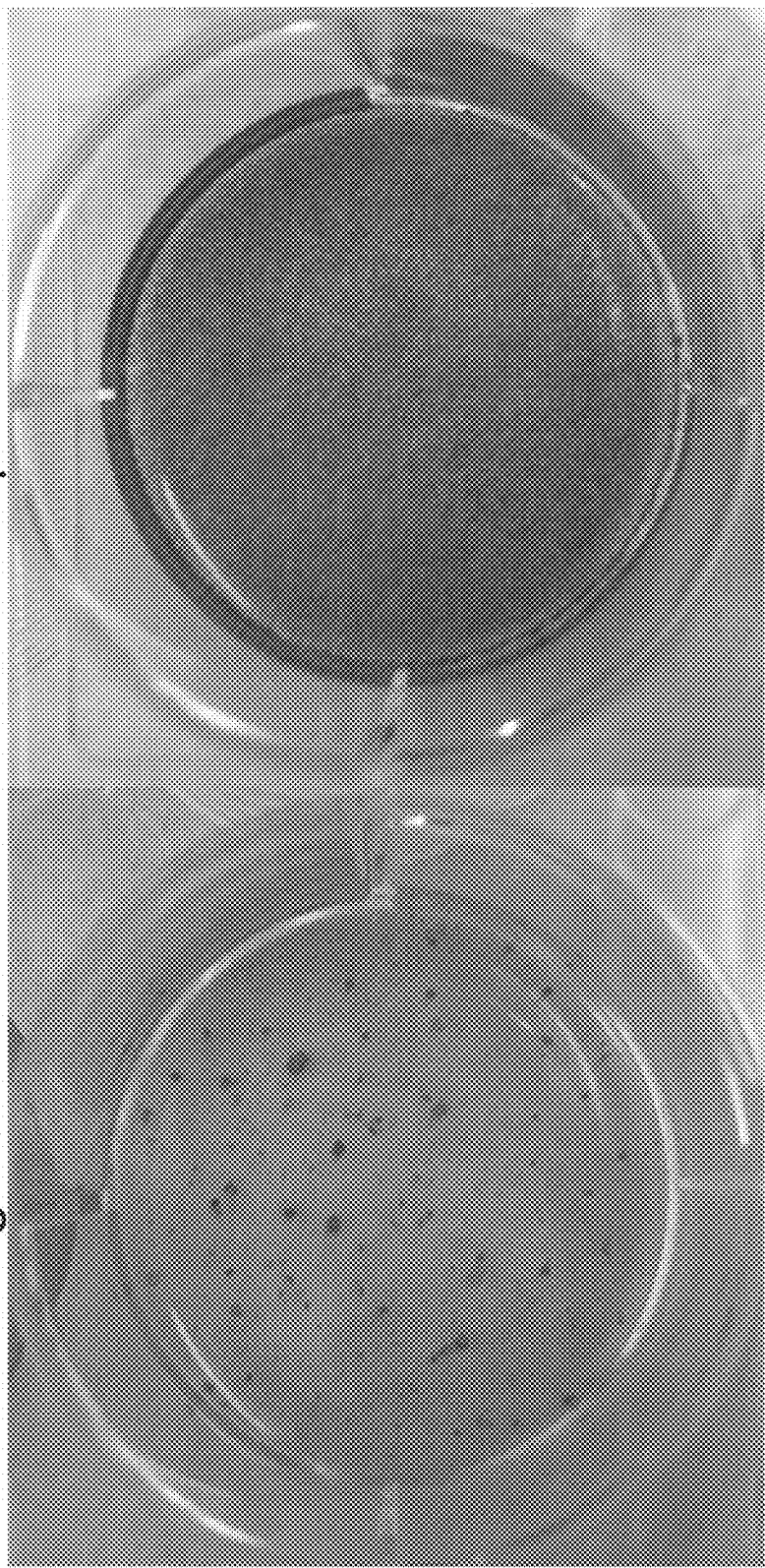
FIGS. 5A to 5B are a set of digital images showing FACS purified GFP positive cells differentiate into pigmented RPE cells. When FACS purified GFP positive and negative cells were re-seeded on to culture plates, only GFP positive cells grew to form homogenous pigmented cultures. This demonstrated that GFP expression truly represents RPE fate in this iPSC line

Next, sorted GFP positive and negative cells were re-plated onto new dishes. GFP negative cells grow to form very few pigmented colonies (FIG. 5A). In comparison, GFP positive cells develop in to pure, fully confluent RPE monolayers (FIG. 5B). This confirmed that the GFP expression truly represents RPE-fate in these cells and demonstrated that GFP signal can be used as a reliable indicator of RPE differentiation. To optimize differentiation of RPE from iPSCs, a reference protocol was established (see Idelson et al. (2009), Cell Stem Cell 5, 396-408; Meyer et al. (2009), Proc. Natl. Acad. Sci. USA 106, 16698-16703; Osakada et al. (2009), J. Cell Sci. 122, 3169-3179. The protocol was divided into four stages—induction of differentiation, differentiation into eye-field/optic vesicle cells, induction of RPE differentiation, and maturation of RPE cells.

Example 3

Induction of Differentiation

Figure 6:
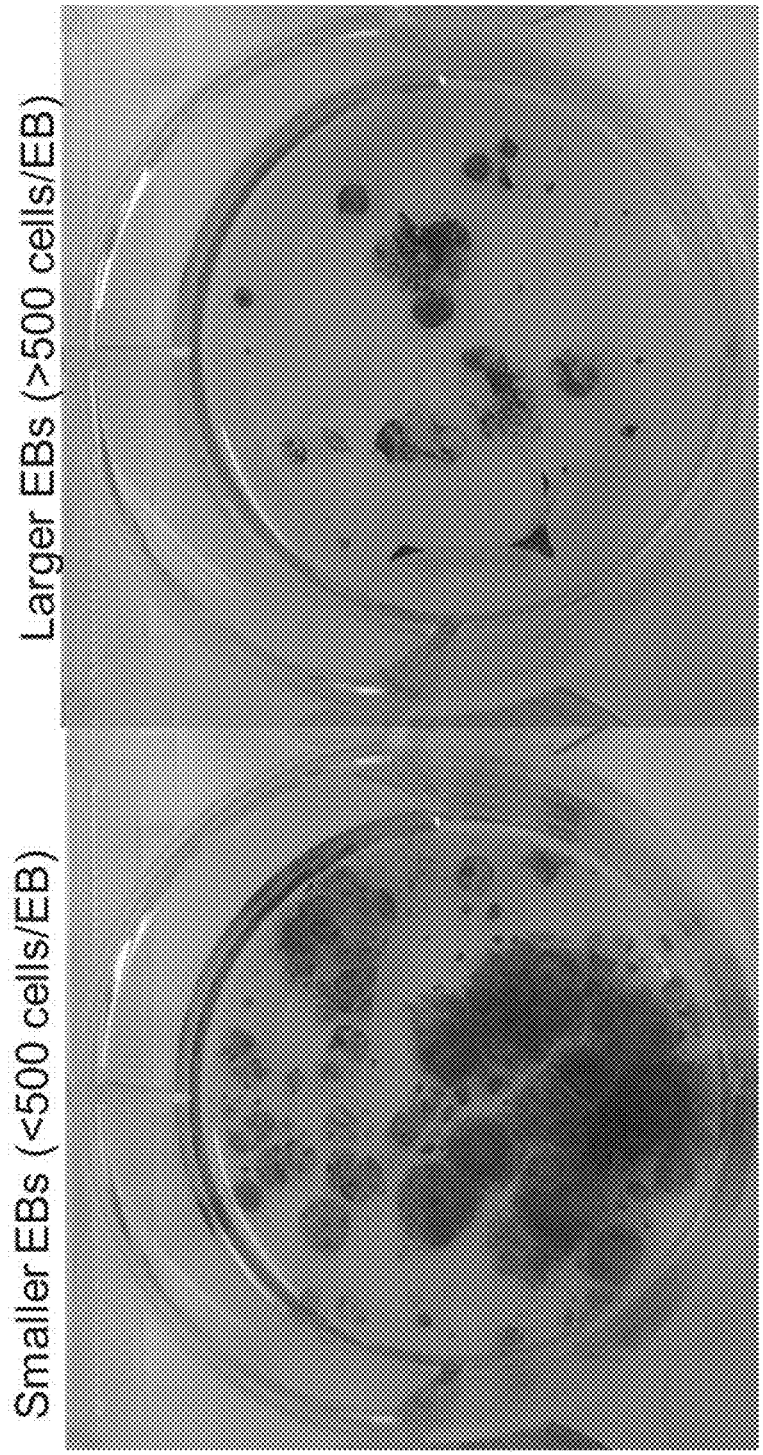
FIG. 6 is a set of digital images showing embryoid body (EB) size affects RPE differentiation. Differences in the number of pigmented cells obtained using varying size EBs are shown.

To induce differentiation of iPSCs, the colonies were lifted by a mild collagenase treatment (1 mg/ml for 15 minutes) and dissociated into small cell aggregates. These aggregates were cultured in RIM medium for 48 hours in non-adherent culture conditions. Within 24 hours, the cell aggregates change into embryoid bodies (EBs). It was determined whether the size of EBs (number of cells/EB) affects RPE differentiation and found that relatively smaller EBS with 200-400 cells/EB efficiently differentiate into RPE as compared to larger EBs (FIG. 6).

Retinal Induction Medium (RIM) (500 ml)

| | |
|---|---|
| DMEM/F12 (1:1) (Invitrogen#11320-033) | 500 ml |
| Knockout Serum Replacement (Invitrogen #10828-028) | 7.5 ml |
| Non-Essential Amino Acids (Gibco#11140) | 5 ml |
| Pen/Strep (Gibco#15140) | 5 ml |
| Sodium Pyruvate (100 mM) (Gibco#11360) | 5 ml |
| N2 Supplement 1x (Gibco#17502-048) | 5 ml |
| B27 Supplement 1x (Gibco#17504-044) | 10 ml |
| CK1-7 Dihydrochloride (5 mM) (Sigma#C0742) | 50 ul |
| SB 431542 hydrate (5 mM) (Sigma#S4317) | 50 ul |
| Noggin (250 ug/ml) (RD Systems#6057-NG) | 2 ul |
| IGF-1 (100 ug/ml) (RD Systems#291-G1) | 5 ul |
| Ascorbic Acid (5 mg/ml) (Sigma#A4544-25G) | 5 ml |

Example 4

Differentiation into Eye-Field/Optic Vesicle Cells

Figure 7:
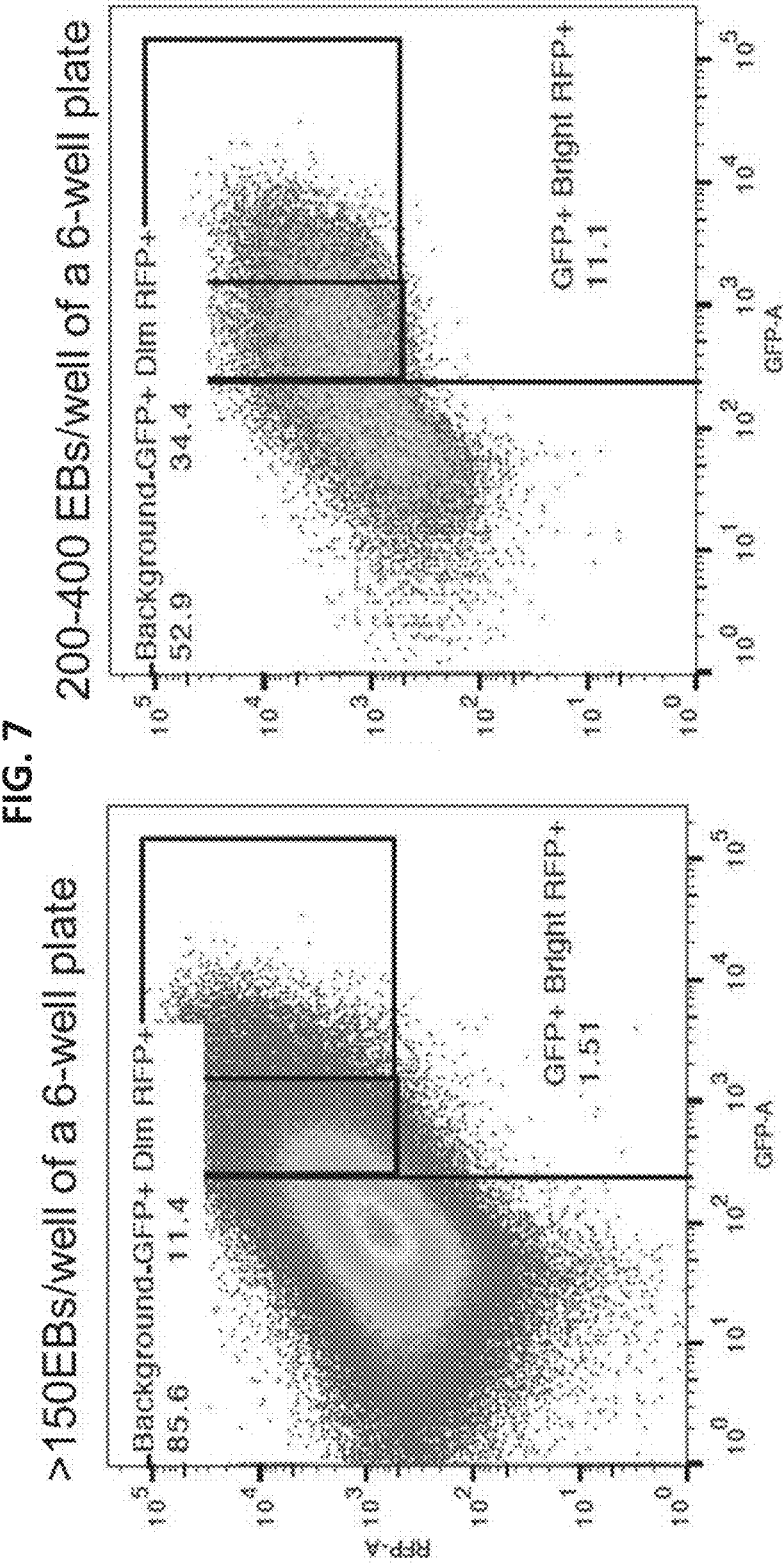
FIG. 7 is a set of digital images showing embryoid body (EB) number affects RPE differentiation. FACS analysis shows that the number of GFP positive cells in the sixth week of the differentiation process. The number of GFP positive cells changes as the number of EBs plated per well of the culture plate change.

After 48 hours of floating EB cultures they are plated onto MATRIGEL® coated plates in RDM medium. It was investigated whether the number of EBs plated/well affects differentiation of iPSCs into RPE. The results showed that ideal differentiation efficiency is achieved by plating 150-250 EBs/well of a standard 6-well tissue culture plate (FIG. 7). RDM medium was used for 3 weeks with change of medium on cells every Monday, Wednesday, and Friday. Inhibition of Nodal, BMP, and WNT pathways can be important for differentiation of stem cells into eye-field cells. To inhibit the nodal pathway, the inhibitor SB431542 was used. To inhibit the activity of BMP pathway, various concentrations of Noggin, a BMP inhibitor, were tested. For WNT pathway inhibition, a combination of biological Wnt inhibitor DKK1 and a small molecule inhibitor of the WNT pathway CK1-7 were used.

Results have shown that inhibition of FGF signaling is important for RPE development. Therefore, the activity of FGF signaling pathway was modulated by either changing its concentration or/and by adding FGF inhibitor (PD 0325901) to the medium. The results were scored weekly by quantitative gene expression measurements of two transcription factors Pax6 and Mitf which are the master regulators of RPE differentiation (FIGS. 8-13). In addition, GFP expression was scored after six weeks as a direct measure of induction of RPE cells (FIG. 14).

The results showed that dual inhibition of WNT pathway, inhibition of FGF pathway, and use of 50 ng/ml of Noggin significantly and progressively improve the expression of Pax6 and Mitf during the three weeks, suggesting that the cells have attained optic vesicle identity by the end of the third week. The GFP signal measured at the end of normal RPE differentiation confirms that these treatments significantly improve RPE differentiation from iPSCs.

Figure 15:
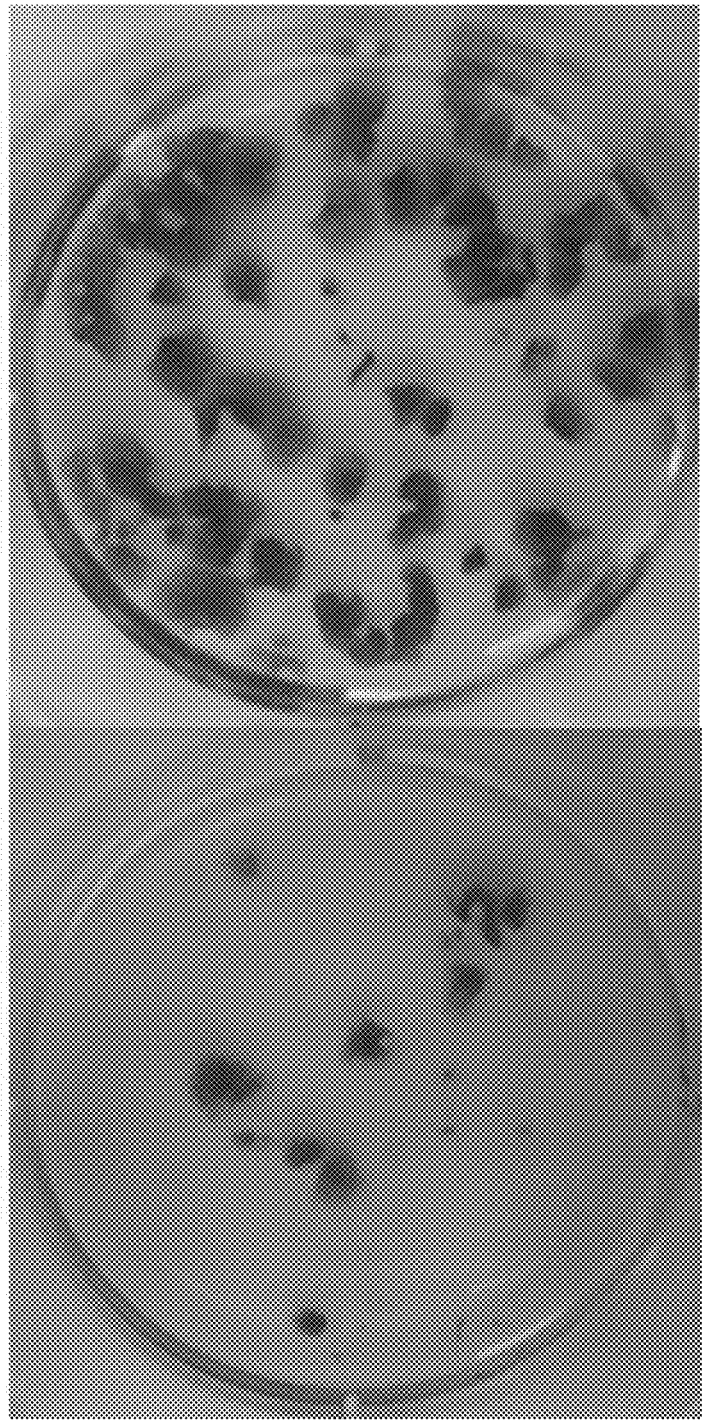
FIG. 15 is a set of digital images showing the differentiation of iPSC into RPE. The cells were cultured using the media and protocols listed in Example 1. For these studies, the KO serum was the only component that was varied.

Next, the effect of the concentration of knockout serum replacement (KSR) on RPE differentiation was tested. Reducing KSR to 1.5% increased the number of pigmented RPE cells when differentiated from the RPE (FIG. 15).

Retinal Differentiation Medium (RDM) (500 ml)

| | |
|---|---|
| DMEM/F12 (1:1) (Invitrogen#11320-033) | 500 ml |
| Knockout Serum Replacement (Invitrogen #10828-028) | 7.5 ml |
| Non-Essential Amino Acids (Gibco#11140) | 5 ml |
| Pen/Strep (Gibco#15140) | 5 ml |
| Sodium Pyruvate (100 mM) (Gibco#11360) | 5 ml |
| N2 Supplement 1x (Gibco#17502-048) | 5 ml |
| B27 Supplement 1x (Gibco#17504-044) | 10 ml |
| CK1-7 (5 mM) (Sigma#C0742) | 0.5 ml |
| DKK1 (100 ug/ml) (R&D Systems) | 0.5 ml |
| SB-431542 (5 mM) (Sigma#S4317) | 0.5 ml |
| Noggin (250 ug/ml) (RD Systems#6057-NG) | 0.1 ml |
| IGF-1 (100 ug/ml) (RD Systems#291-G1) | 50 ul |
| Ascorbic Acid (5 mg/ml) (Sigma#A4544-25G) | 5 ml |
| PD 0325901 (1 mM) (Tocris#4192) | 0.5 ml |
| NO FGF | |

Example 5

Induction of RPE Differentiation

Figure 16:
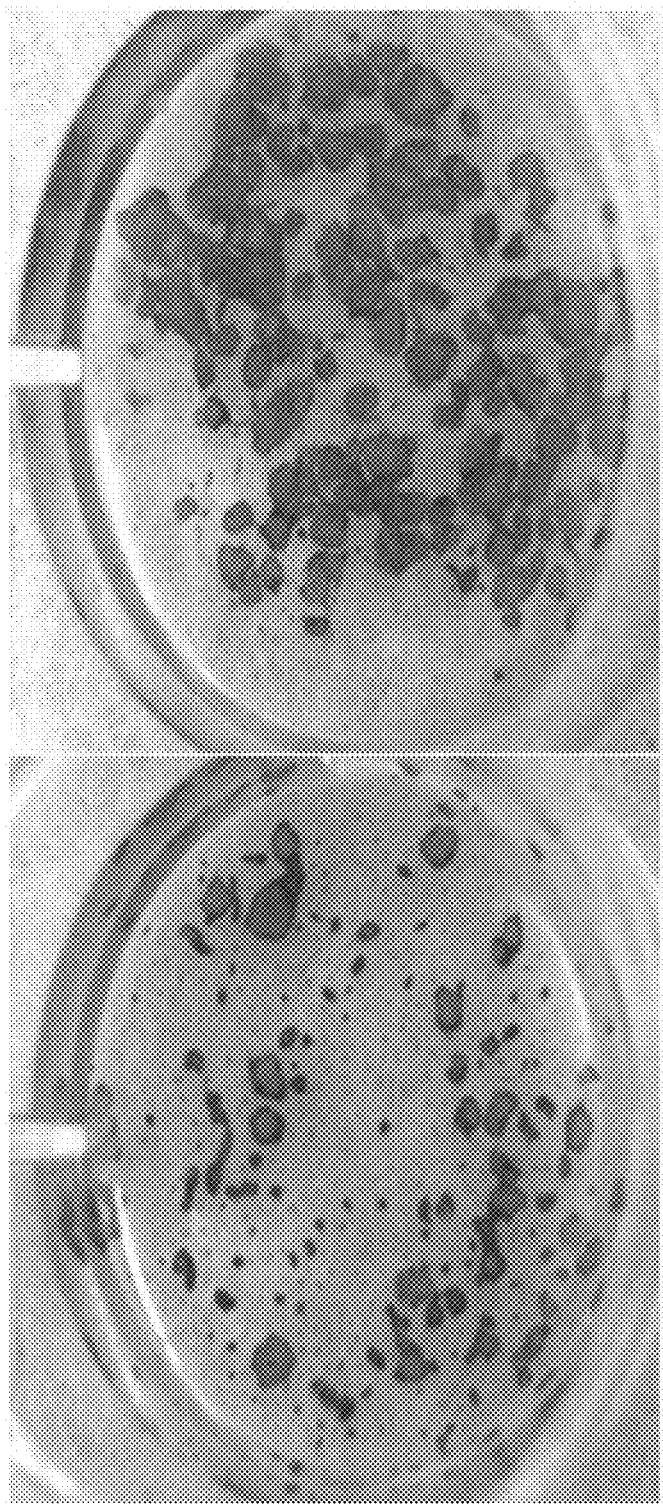
FIG. 16 is a set of digital images showing that canonical WNT and WNT3a improves the efficiency of production of RPE from iPSCs. WNT3A is a canonical WNT signaling regulator. The digital images show pigmented colonies in each dish after eight weeks of culture. For these experiments MEDIUM 2 (FGF2–0.5 ng/ml)+MEDIUM 3 (NA or NAW), wherein NA=Nicotinamide & ACTIVIN, NAW=Nicotinamide, ACTIVIN & WNT3a. bFGF (FGF2) was included 0.5 ng/ml in medium 2.
Figure 17:
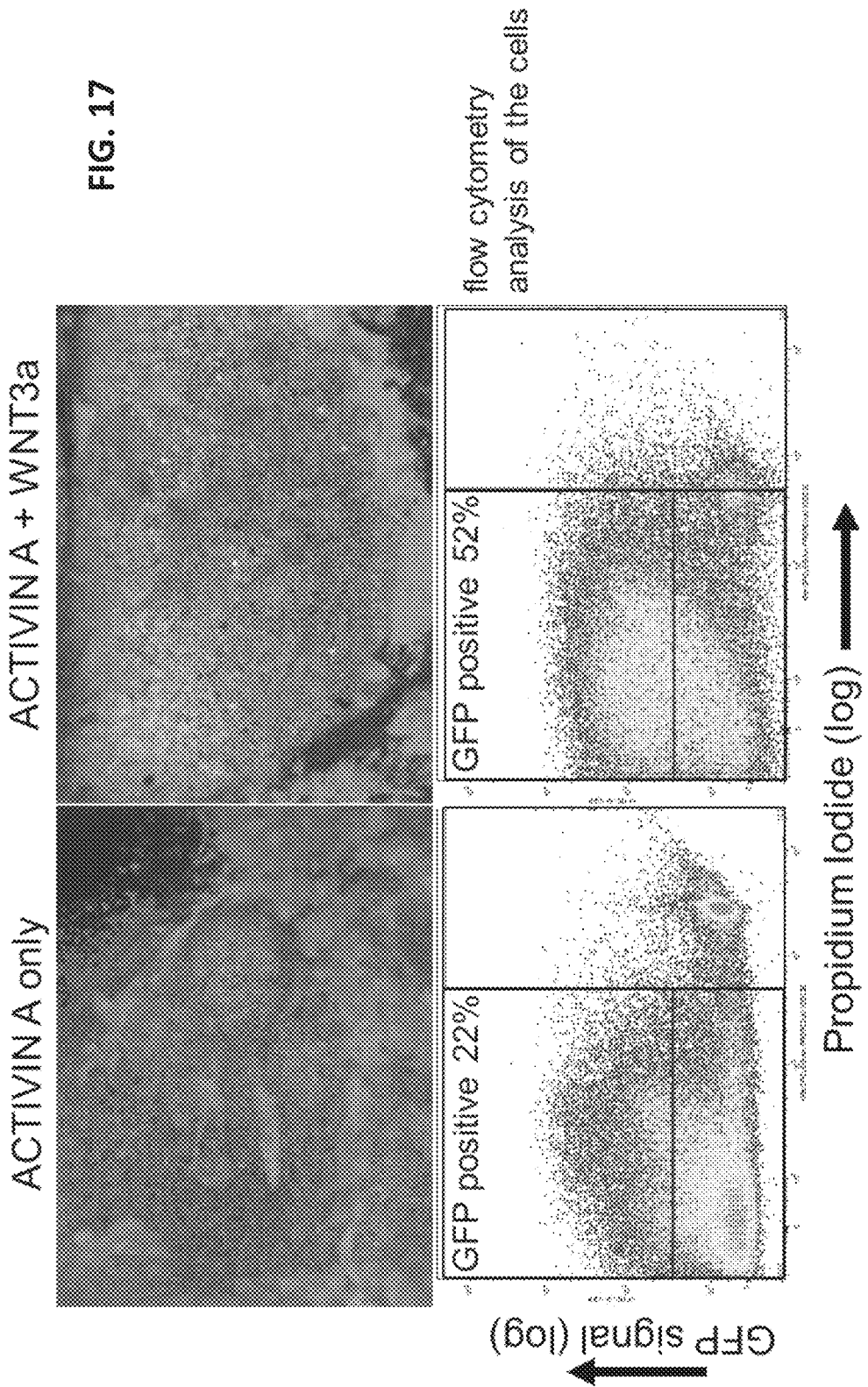

Activin A induces RPE differentiation from ES cells. In animal models, canonical WNT (WNT3a) is important for RPE differentiation. It was hypothesized that a combination of activin A and WNT3a would be effective for the induction of RPE differentiation from iPSCs. A combination of these two factors was tested at the optic vesicle stage. Cells were moved from the RDM medium to medium containing either activin A (NA) only or activin A plus WNT3a (NAW). The addition of WNT3a significantly increased the number of pigmented cells per dish (FIG. 16). Because this differentiation process was started with the reporter iPSC lines, the increase in the number of RPE cell was confirmed by comparing the GFP signal between the two treatments. As compared to NA, NAW increased the number of GFP positive cells in the culture (FIG. 17, top panel). When quantified by FACS analysis, NA treatment produced only 22% GFP positive cells, whereas NAW treatment produced 52% GFP positive cells (FIG. 17, bottom panel). This result showed that WNT signaling synergistically enhances RPE differentiation capacity of TGF-beta (activin) signaling.

Retinal Medium (RM)+Nicotinamide, Activin, and Wnt3a (NAW) (500 ml)

| | |
|---|---|
| DMEM/F12 (1:1) (Invitrogen#11320-033) | 500 ml |
| Knock out Serum Replacement (Invitrogen #10828-028) | 7.5 ml |
| Non-Essential Amino Acids (Gibco#11140) | 5 ml |
| Pen/Strep (Gibco#15140) | 5 ml |
| Sodium Pyruvate (100 mM) (Gibco#11360) | 5 ml |
| N2 Supplement 1x (Gibco#17502-048) | 5 ml |
| B27 Supplement 1x (Gibco#17504-044) | 10 ml |
| Nicotinamide (Sigma#N0636) (1M) | 5 ml |

| | |
|---|---|
| Activin (RD Systems#338-AC) (50 ug/ml) | 1.5 ml |
| Wnt3a (RD Systems#5036-WN) (200 ug/ml) | 250 ul |

Example 6

Maturation of RPE Cells

Figure 18:
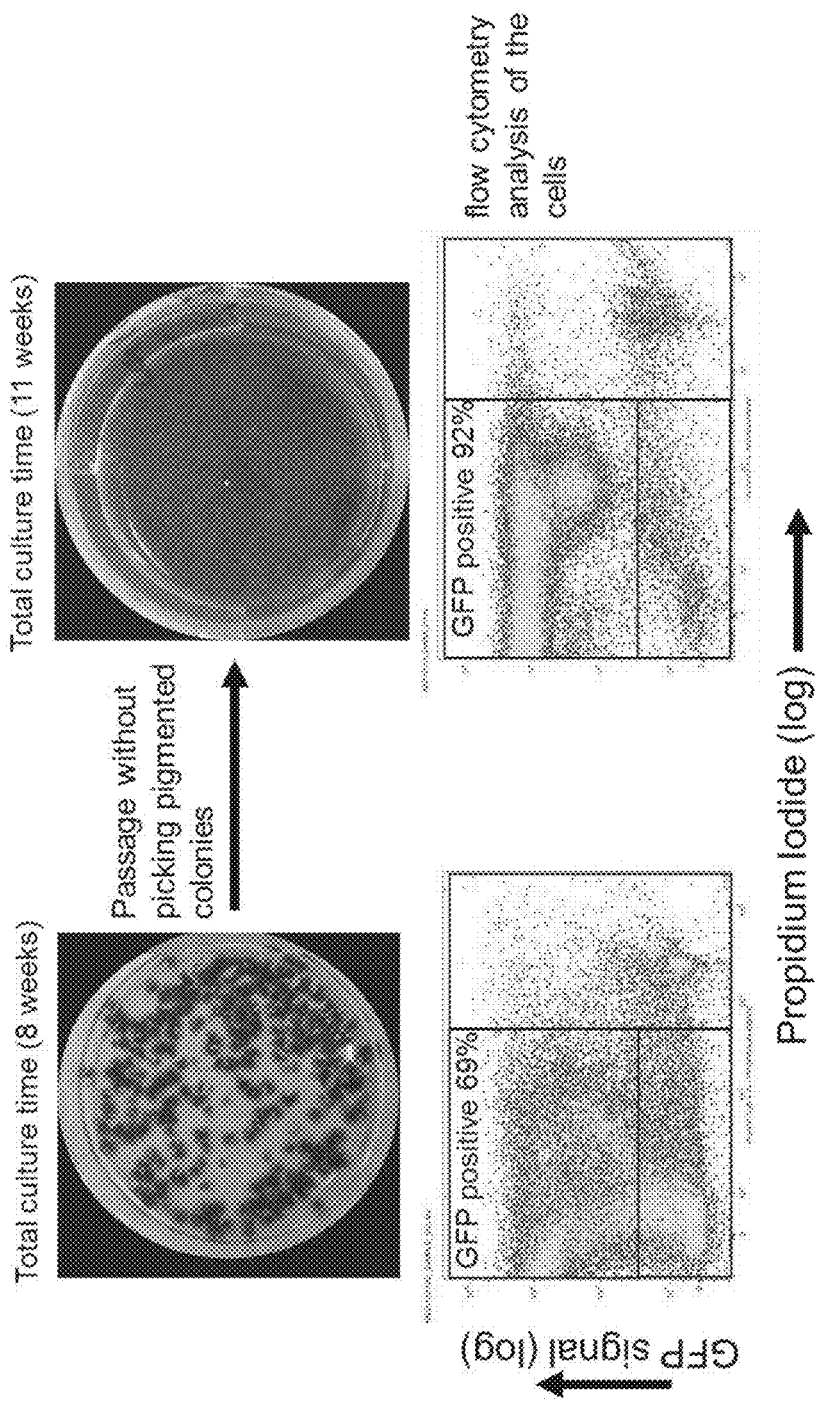
FIG. 18 is a set of digital images and plots showing the use of a GFP reporter to optimize iPSC to RPE Differentiation. Culture in the third medium significantly improved the production of RPE cells, as evidence by GFP expression and production of pigment, after 6 weeks.

To further purify and mature RPE cells, these cells were trypsinized and cultured in 5% RPE medium for 4 weeks on semipermeable transwells. This produced cells which looked quite homogenous in terms of RPE pigment (FIG. 18, top panel). Quantification of the GFP signal by FACS analysis produced up to 92% GFP positive cells in cultures that have grown for 4 weeks. This suggests that the 5% RPE medium enriches for RPE cells. When these cells were cultured for longer durations, NAW treated cells looked more homogenous in terms of RPE pigment, RPE morphology, and GFP expression as compared to NA treated cells (FIG. 19, FIG. 20 only for NAW cells). However, these cells continue to express fetal specific RPE genes such as Pax6, Sox2, Tfec etc.

Differentiating RPE cells start producing canonical WNT that can affect the maturity of RPE cells. Therefore, to generate RPE cells that are fully mature and stop expressing fetal genes, these cultures were treated with inhibitors of canonical WNT pathway. WNT5a and DKK1, which together inhibit canonical WNT pathway and induce non-canonical WNT pathway, were used in these studies. The later has been shown to induce cell polarization and maturity. In addition, inhibitors of FGF (SU54052) and Sonic hedgehog (Cyclopamine) pathways were used to suppress any endogenous FGF and Sonic signaling, which may affect RPE maturity. These inhibitors were used for 2 weeks and the cells were assayed immediately after the treatment. The expression of several fetal RPE and mature RPE specific genes were measured (FIG. 21). Interestingly, these treatments down-regulated the expression of fetal RPE specific genes (Pax6, Sox2, Tfec, Klf4, Snail1/2) and up-regulated the expression of RPE maturity associated genes (TYR, TYRP1, MYRIP, Cadherin 1/3, TRPM1/3).

In conclusion, a protocol was developed that significantly improves iPSC to RPE differentiation and also generates cells that are fully differentiated. This protocol is extremely valuable to produce RPE cells from iPSCs that can serve appropriate disease models and an effective cell-based therapy.

5% Retinal Pigmented Epithelial (RPE) Media

| | |
|---|---|
| MEM_modified (M-4526) | 500 ml |
| N1 supplement (N-6530) | 5 ml |
| Glutamax, Penicillin-streptomycin (G-1146) | 5 ml |
| Non essential amino acids (M-7145) | 5 ml |
| Taurine (T-0625) | 125 mg |
| Hydrocortisone (H-0396) | 10 ug |
| Triiodo-thyronin (T-5516) | 0.0065 ug |
| Fetal bovine serum, heat inactivated | 5% |
| DKK1 (100 ug/ml) (R&D Systems) | 0.5 ml |
| Wnt5a (RD Systems) (100 ug/ml) | 250 ul |
| SU5402 (sigma) (10 uM) | 0.5 ml |
| Cyclopamine (Sigma) (10 uM) | 0.5 ml |

Example 7

Authentication of iPSC-Derived RPE Cells

To authenticate the cells obtained through this protocol, the cells were tested by both molecular and physiological assays. A set of signature genes was selected from a previously published RPE-gene signature (Strunnikova et al. (2010), Hum. Mol. Genet. 19: 2468-2486) and the expression of those genes was compared between primary human RPE and RPE obtained from iPSCs using our protocol. The resulting cells closely resemble the primary human RPE in terms of the expression of RPE-specific genes (FIG. 22).

Similarly, the ability of iPSC-derived RPE to respond to changing $CO_2$ concentrations in the apical and basal baths, and their ability to hyperpolarize in response to changing potassium concentrations in the apical bath was assessed (FIG. 23, 24). In all these assays, iPSC-derived RPE cells behave similar to primary human RPE. Thus, the disclosed protocol produces RPE cells that are fully functional. These molecular and physiological assays are important biomarkers for complete RPE differentiation.

Example 8

Multiplex High Throughput Screening

A multiplex high-throughput screening approach was developed that simultaneously detects endogenous expression of multiple developmental, functional, and disease markers in iPSC-derived retinal pigment epithelium (RPE). Protocols were optimized for differentiation and growth of iPSC-derived RPE for high-throughput screening in 96-well and 384-well formats. As a proof of principle, the endogenous expression of ten genes in iPSCs, iPSC-derived RPE at two differentiation stages, and primary human RPE cells were compared using the multiplex assay. Data obtained from the assay are significantly correlated with standard qRT-PCR based measurements. This assay provides the basis to screen for compounds that improve RPE function, maturation, and target disease pathways thus providing the basis for effective treatments of several retinal degenerative diseases.

Protocols were developed to use fully-authenticated iPSC-derived RPE for a multiplex high-throughput assay. This multiplex gene expression assay reports on six RPE lineage genes, two stem/progenitor cell genes, and two house-keeping genes. Proof of principle data was obtained that 1) the assay can be performed in 96-well and 384-well high-throughput modes, 2) the assay is able to measure even subtle change in gene expression, 3) the data obtained with the multiplex assay is highly correlated with RT-qPCR data. This assay allows identification of small molecules that can further enhance the efficiency of the differentiation protocols toward fully mature RPE cells. In addition, it provides developmental and functional biomarkers that can be tracked in a high-throughput mode. Small molecules that modulate the expression of these functional and disease biomarkers can provide potential therapeutic drugs for RPE-associated retinal degenerative diseases.

A. Materials and Methods iPSC Derivation, Culture, and Differentiation:

Human adult dermal fibroblasts (AG9309, female, 21 years old, toe biopsy) purchased from Coriell (Camden, N.J.) were reprogrammed (15). iPSC were differentiated into three germ layers or into RPE (12, 15-17).

Immunostaining, Electron Microscopy, and qRT-PCR Analysis:

Immunostaining and qRT-PCR analysis was performed (Green et al., *Nature biotechnology* 29(3):267-272, 2011; Bharti et al., *PLoS Genet* 8(7):e1002757, 2012). Following antibodies were used: ALEXAFLUOR® 488-anti Tra-1-60 (1:50, BD Biosciences); ALEXAFLUOR® 488—anti SSEA4 (1:50, BD Biosciences); OCT4 (1:400, Cell Signaling, Danvers, Mass.); NANOG (1:100, R&D Systems); SOX2 (1:100, Santa Cruz, Dallas, Tex.); KLF4 (1:50, Santa Cruz); c-MYC (1:50, Santa Cruz); AFP (1:75, Thermo Scientific, Waltham, Mass.); TUJ1 (1:400, Sigma, St. Louis, Mo., http://www.sigmaaldrich.com); aSMA (1:500, Thermo Scientific); DCT (1:100, Bioworld antibodies, Mt. Airy); PAX6 (1:200, Covance Chantilly, Va.); and ZO1 (1:100 Life Technologies).

Intracellular Calcium Measurements and Electrophysiology:

To assess calcium signaling in the RPE cells: ATP (200 µM; Sigma) and Cyclopiazonic Acid (CPA; 10 µM; EMD Millipore); (see Maminishkis et al., *Invest. Ophthal. Vis. Sci.* 47(8):3612-3624, 2006); Quinn et al., *Invest. Ophthal. Vis. Sci.* 33(13):3513-3527, 1992).

Calomel electrodes in series with Ringer solutions and agar bridges were used to measure the transepithelial potential (TEP). The signals from intracellular microelectrodes were referenced to the basal bath to measure the apical and basal membrane potentials, $V_A$ and $V_B$, where $TEP=V_B-V_A$. The total transepithelial resistance ($R_t$), and the ratio of the apical to basolateral membrane resistance ($R_A/R_B$) were obtained by passing 2-4 µA current pulses (peak to peak) across the tissue and measuring the resultant changes in TEP, $V_A$ and $V_B$. See Maminishkis et al. supra and Quinn et al., supra for details.

Principle of QUANTIGENE PLEX® Technology:

Cells grown in 96-well or 384-well plates are lysed and the lysate transferred to a hybridization plate containing QUANTIGENE PLEX® probe and LUMINEX® beads sets. Each bead type is coated with a different single strand DNA Capture Probe (CP). Other components of the QUANTIGENE® Probe set that are also comprised of ssDNA oligos include Capture Extenders (CE), Label Extenders (LE) and Blocking Probes (BP). Part of CE oligos is complementary to the target mRNA (cover 200-600 bases) and part to CP bound on LUMINEX® beads. This interaction facilitates capture of specific target mRNAs to specific LUMINEX® beads. LE include target mRNA specific sequences and a binding site for the preamplifier, the first component used for signal amplification. BP bind to any sequences on the target mRNA that are not bound by the CE and LE. A typical probe set for a single target mRNA consists of a family of four or more different CE and LE that usually cover about 500 bases within the target mRNA. After washing off excess probes and remaining cell lysate the signal amplification reagents consisting of the Preamplifier (PreAmp), Amplifiers (Amp), and Label Probes (LP) are sequentially hybridized to the mRNAs. The LP also includes a biotin molecule, which in turn is a binding site for the final signal amplification reagent, SAPE (Streptavidin-conjugated R-Phycoerythrin). Each Amplifier binds up to 400 SAPE. The resulting fluorescence signal associated with individual Capture Beads is read on a LUMINEX® instrument. Signal is reported as median fluorescence intensity (MFI) and is proportional to the number of target RNA molecules present in the sample. MFI is calculated by measuring signals on 50-100 beads/gene. MFI values obtained from background blank wells with no target RNA were subtracted from MFI of each target reading.

QUANTIGENE PLEX® 2.0 Reagent System:

96-well Assay Protocol: The QUANTIGENE PLEX® 96-well Assay was done as described in the manufacturer's manual (QUANTIGENE PLEX® 2.0 Assay, Affymetrix, Santa Clara, Calif.). 25,000 and 50,000 cells are seeded per well and cultured for 14 days at 37° C., 5% $CO_2$. Cells were lysed in 200 µL working lysis mixture for 30 minutes at 50° C. 80 µL of cell lysate were transferred to the assay's hybridization plate (96-well clear polypropylene plate Abgene #AB0796, Pittsburgh, Pa.), where each well already contained 20 µL Working Bead Mix (6.6 µL Lysis Mixture, 5.2 µL nuclease free water, 0.2 µL Proteinase K solution, 2 µL Blocking Reagent, 5 µL Probe Set, 1 µL magnetic LUMINEX® beads; QUANTIGENE PLEX® Set-Panel #11828). Hybridization was done for 18-22 hours at 54° C.±1° C., shaking 600 rpm. The hybridization mixtures were then transferred to a 96 well Magnetic Separation Plate (96-well flat bottom microplate Nunc #269620). An Affymetrix Hand Held Magnetic Bead Washer (Affymetrix P/N QP0702) was used to wash the beads, thus removing all unbound materials. 100 µL of 2.0 Pre-Amplifier Working Reagent (3:1000 dilution using PreAmp solution+Amp diluent provided by manufacturer) was added to each assay well. The Magnetic Separation Plate was sealed with adhesive backed foil and incubated for 1 hour at 50° C.±1° C. and 600 rpm. The unbound 2.0 Pre-Amplifier was removed and beads washed 3× with 100 µL Wash Buffer (provided by manufacturer) using the handheld magnetic washer. This was followed by incubation with 2.0 Amplifier Working Reagent, followed by Label Probe Working Reagent, and finally followed by SAPE Working Reagent (all three solutions 100 µL at 3:1000 dilution, manufacturer provided). Incubation and washing were done as described above. Signals from the beads were measured with a LUMINEX® FLEXMAP® 3D instrument (LUMINEX® Corp. Austin, Tex.), after re-suspending the beads in 130 ul SAPE Wash Buffer, using dd gate settings of 5,000-25,000. 50-100 beads per target were measured in a sample volume of 100 ul.

QUANTIGENE PLEX® 384-Well Assay Protocol:

The QUANTIGENE PLEX® 384-well Assay was optimized using technical support from Affymetrix and using the 96-well assay protocol provided by the manufacturer. 6,000 and 12,000 cells were seeded per well of a 384 well plate. Proportional volumes of reagents/well were used for the 384-well plate. Signal was measured as described above.

B. Results

1. Generation of iPSC-Derived RPE

Figure 25A:
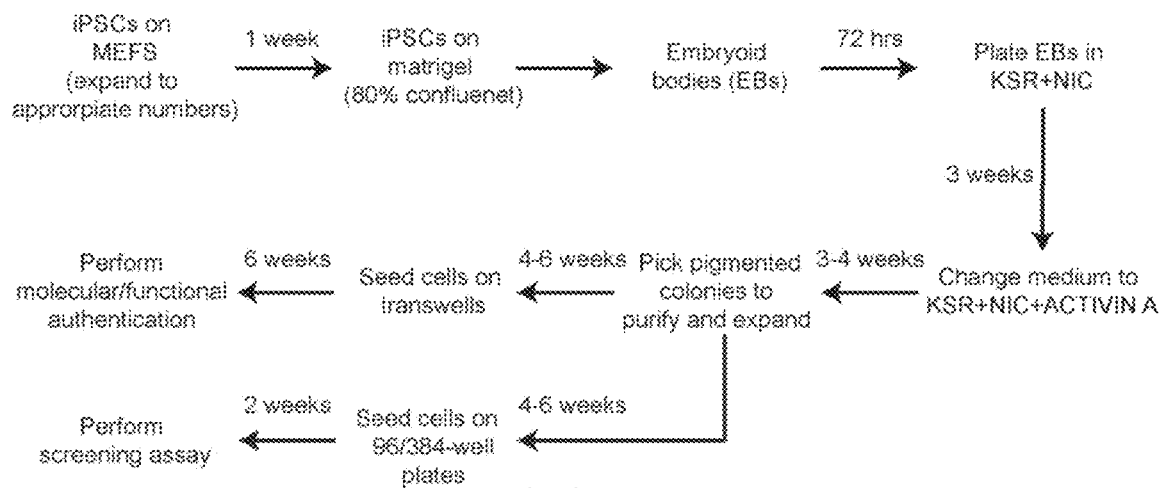
Figure 25B:
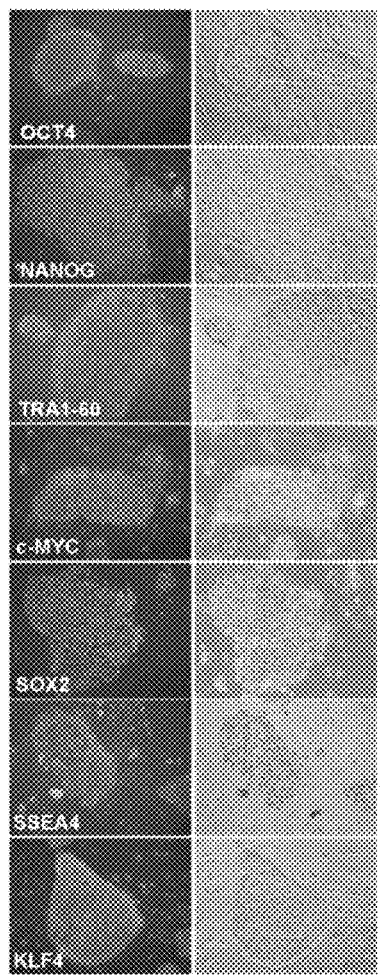
Figure 25C:
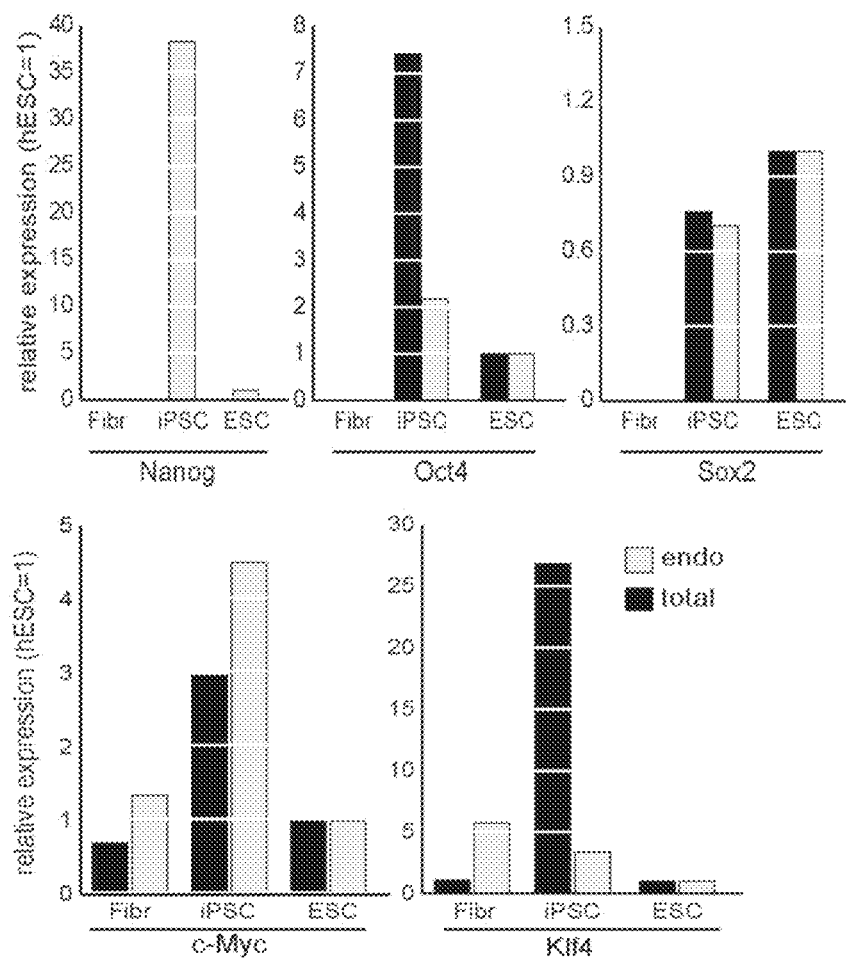
Figure 25D:
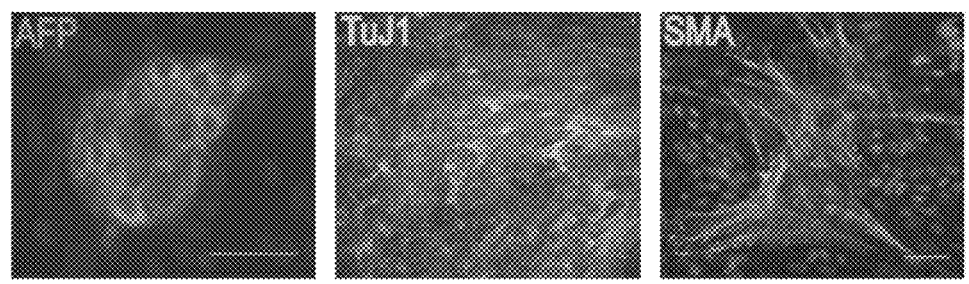
Figure 26A:
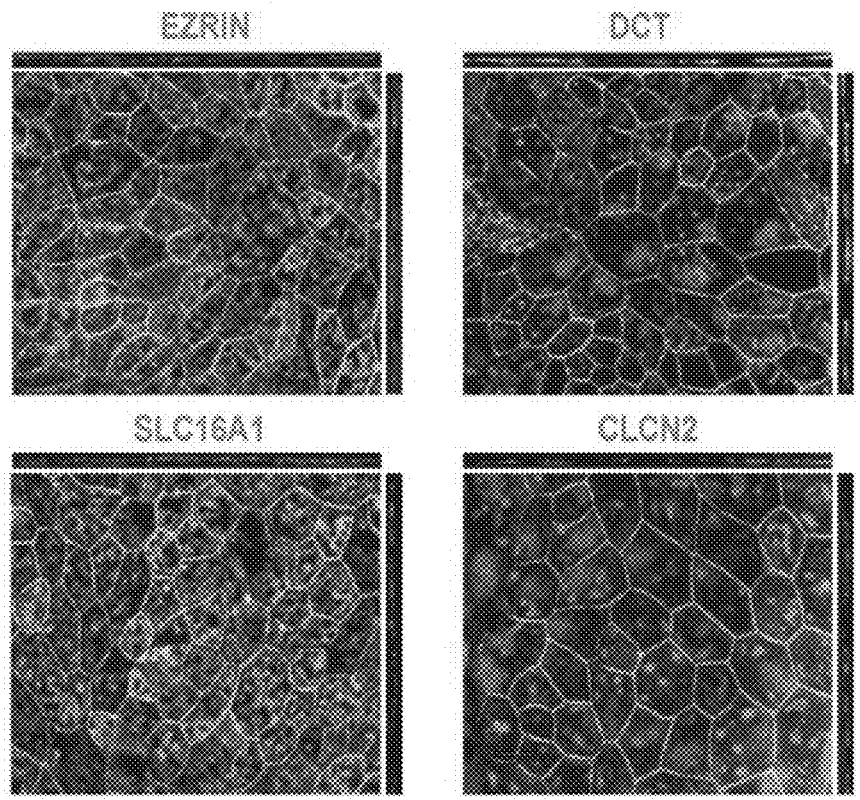
Figure 26B:
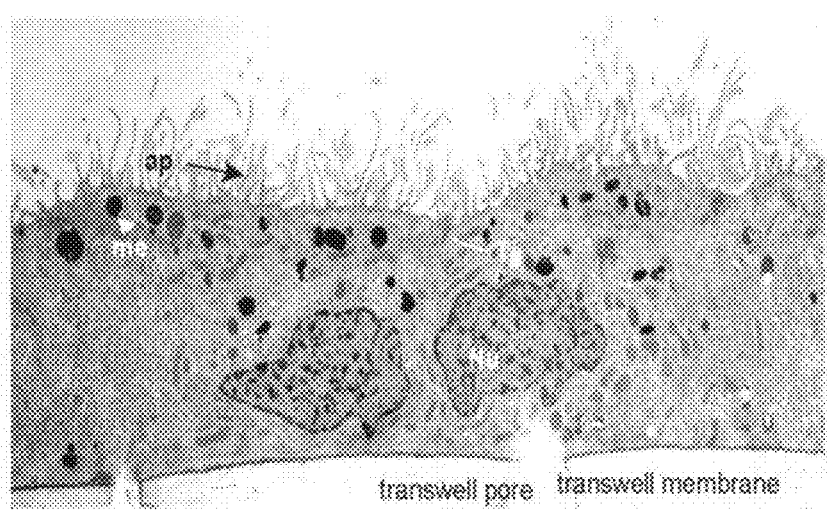

A high content screening assay was developed that simultaneously monitors developmental and functional features of stem cell-derived RPE. FIG. 25A provides an overview of the experimental strategy for obtaining pure cultures of iPSC-derived RPE, the steps required to prepare cells for functional authentication and use in a high-throughput screen. iPSCs were generated from human adult female dermal fibroblasts, using retroviral vectors expressing OCT3/4, c-MYC, SOX2, and KLF4. Pluripotency of selected iPSC colonies was determined using the following three pluripotency validation assays: (I) positive immunostaining for pluripotency markers NANOG, SSEA4, TRA1-60, OCT3/4, c-MYC, SOX2, and KLF4 (FIG. 25B); (II) comparison of mRNA expression of NANOG, OCT3/4, c-MYC, SOX2, and KLF4 to an embryonic stem cell line and to dermal fibroblasts. The transduced viral vector also expressed OCT3/4, c-MYC, SOX2, and KLF4, therefore, specific primer sets were used to distinguish expression from the endogenous locus to the total expression (viral vector+ endogenous) (FIG. 25C). Expression of pluripotency markers from endogenous loci in iPSCs was significantly higher as compared to dermal fibroblasts and comparatively higher or equal to undifferentiated ES cells (FIG. 25C); (III) ability of iPSCs to differentiate into all three germ layers. As shown in FIG. 25D, this iPSC line differentiates into all three germ layers.

iPSCs were differentiated into RPE using the methods disclosed herein. Pigmented cell clusters with RPE-like cobblestone morphology were manually picked and expanded in a T25 flask to obtain pure cultures of RPE cells. Purified RPE cells were re-seeded onto transwell filters to obtain polarized confluent electrically intact RPE monolayers in approximately 6-8 weeks Immunostaining performed at this stage for epithelial marker ZO1 confirmed the typical epithelial morphology of the cells (FIG. 26A). iPSC-derived RPE also expressed EZRIN, an apical process localized protein; DCT, an enzyme important for RPE pigmentation; CLCN2, a chloride channel that is critical for volume regulation of the RPE; and SLC16A1, an apical membrane monocarboxylate transporter that is required for lactate transport across the RPE monolayer and involved in intracellular pH regulation. Analysis of transmission electron microscopy images revealed several typical RPE features in these cells such as cigar and oval shaped melanosomes localized predominantly apically (me, arrowhead), tight junctions (tj) between adjoining cells, and apical processes (arrow) (FIG. 26B).

Figure 26C:
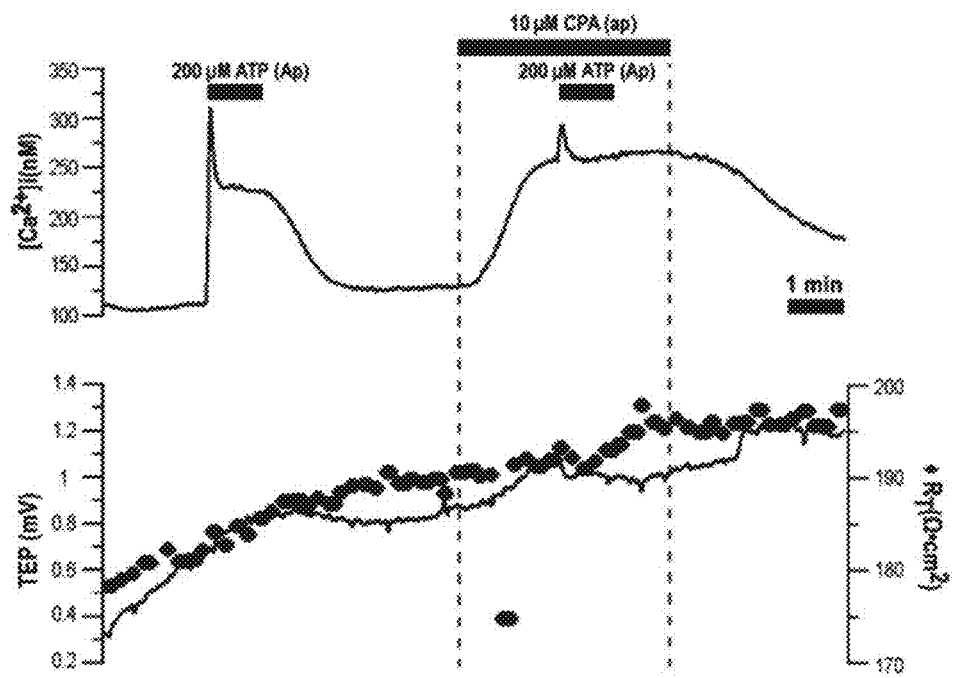
Figure 26D:
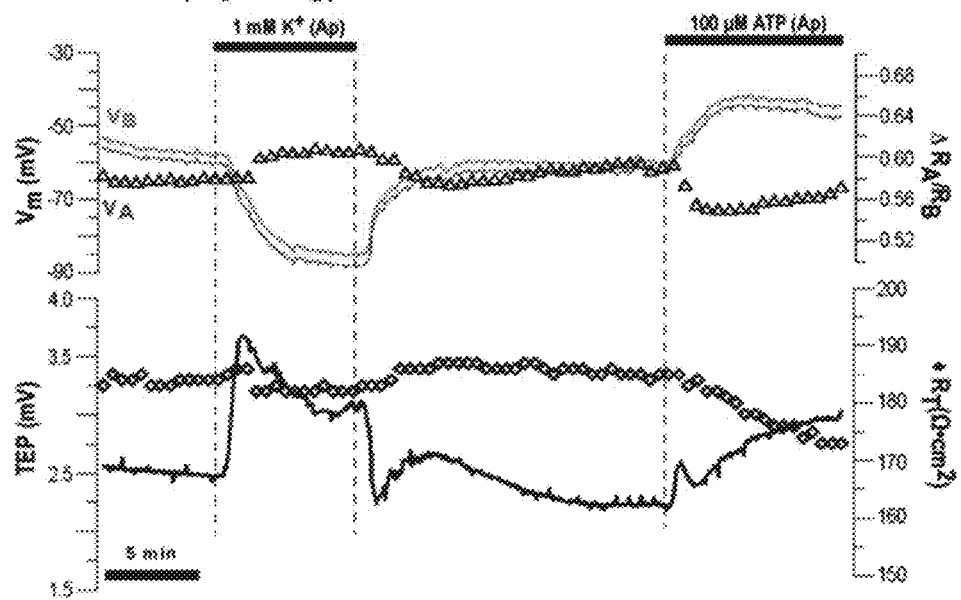

Many characteristic physiological responses of human native and cultured RPE cells can be measured in vitro. iPSC-derived RPE monolayer cultures display several of these features. These cells are electrically intact displaying a transepithelial resistance across the monolayer of 170-200 $\Omega \cdot cm^2$ (FIGS. 26C and 26D) and their steady-state intracellular calcium concentration is 120 nM. Similar to native RPE, in iPSC-derived RPE stimulation of apical membrane P2Y2 receptors by ATP leads to a typical bi-phasic response, the initial response signals the release of intracellular calcium from the endoplasmic reticulum into the cytoplasm, and the second phase is dependent on the presence of extracellular $Ca^{2+}$ (Maminishkis et al., *Investigative ophthalmology & visual science* 47(8):3612-3624, 2006). Application of cyclopiazonic acid blocks sarco/endoplasmic reticulum $Ca^{2+}$ ATPase, an ATP dependent calcium reuptake channel located on the ER membrane leading to steady-state calcium increases and blunts the ATP response (FIG. 26C). Electrophysiologically, the resting membrane potentials of apical and basal membranes are approximately −55 mV (basal side slightly more depolarized as compared to the apical side) leading to a transepithelial potential (TEP) across the monolayer of 2.5 mV, apical side positive (FIG. 26D). Changes in $K^+$ concentration in the apical bath from 5 mM to 1 mM, which mimics the in vivo alterations in subretinal space $K^+$ following dark to light transitions, significantly hyperpolarizes the apical membrane by 10-20 mV, thus leading to a sharp decreases in TEP (17, 20). Application of ATP to the apical membrane significantly depolarizes the basolateral membrane following the release of calcium from intracellular stores and activation of basolateral membrane $Ca^{2+}$—activated Cl⁻ channels (Maminishkis et al., supra; Quinn et al., supra; Steinberg et al., *Documenta ophthalmologica. Advances in ophthalmology* 60(4):327-346, 1985).

The expression of pluripotency and RPE signature genes was compared in undifferentiated iPSCs, iPSC-derived RPE, and primary human fetal RPE using qRT-PCR (Liao et al., *Human molecular genetics* 19(21):4229-4238, 2010; Strunnikova et al., *Human molecular genetics* 19(12):2468-248, 2010). Two major pluripotency genes OCT3/4 (also called POU5F1) and SOX2 are downregulated in iPSC-derived RPE as compared to undifferentiated iPSCs suggesting a loss of the pluripotent state. However, several other RPE-specific transcription factors, pigmentation pathways genes, visual cycle genes, structural proteins, and channels were expressed at significantly higher levels in iPSC-derived RPE as compared to undifferentiated iPSCs and at a lower or at similar levels as compared to the primary RPE (Table A).

TABLE A

Fold difference in gene expression in iPSC-RPE as compared to:

| | iPSCs | Primary RPE |
|---|---|---|
| Pluripotency related transcription factors | | |
| POU5F1 | −25.00 | −1.69 |
| KLF4 | 2.80 | 27.92 |
| SOX2 | −20.00 | 23.05 |
| c-MYC | −1.09 | −1.78 |
| RPE-related and developmental transcription factors | | |
| MITF | undetermined* | −5.88 |
| TFEC | undetermined* | −4.17 |
| PAX6 | 44.00 | 1.00 |
| OTX2 | 4.43 | −4.17 |
| SOX9 | 94.16 | −1.89 |
| SIX3 | 61.01 | −5.00 |
| ROR beta | 5.62 | −3.57 |
| LHX2 | 53.71 | −10.00 |
| CRX | undetermined* | −1.67 |
| GAS1 | 19.60 | −1.64 |
| Pigmentation pathway genes | | |
| GPNMB | 429.94 | −5.56 |
| MYRIP | 57.92 | −2.44 |
| RAB27A | 20.32 | −1.96 |
| OCA2 | 31.23 | −5.56 |
| DCT | undetermined* | −3.22 |
| TYROSINASE | undetermined* | −4.00 |
| TYRP1 | undetermined* | −3.03 |
| PMEL | 38.05 | −10.00 |
| Visual cycle genes | | |
| ALDH1A3 | 27.13 | −2.32 |
| RPE65 | 318.03 | −2.94 |
| RDH5 | 151.60 | 2.08 |
| RLBP1 | 58.73 | −2.86 |
| Membrane proteins and channels | | |
| CDH1 | −33.33 | −25.00 |
| CDH3 | −2.86 | −5.88 |
| CLDN16 | u.d. | −1.23 |
| CLDN19 | 26.78 | −3.44 |
| TRPM1 | undetermined* | −1.19 |
| TRPM3 | 59.88 | −1.43 |
| MERTK | 2.81 | −1.09 |
| BEST1 | 1653.15 | −1.96 |
| COL11A1 | 156.39 | 2.99 |
| CSPG5 | 19.48 | −3.57 |

These results suggest that iPSC-derived RPE, have attained an RPE-like phenotype, are but are not in a completely mature state. It is noteworthy that despite the fact that iPSC-derived RPE express higher levels of fetal or progenitor genes (SOX2 and KLF4, see Table A), physiological response of these cells are not significantly compromised. A Proof-of-Principle High-Throughput Scalable Multiplex Gene Expression Assay Using Authenticated iPSC-derived RPE The goals were to develop a high-throughput screening assay that can simultaneously monitor developmental, functional, and disease markers for RPE and perform proof-of-principle analysis of the assay. In designing the screening assay platform, a multiplex gene expression assay was chosen for two main reasons: (1) it is a high content assay that allows the simultaneous detection of genes involved in RPE development, differentiation, function, and pathology; (2) it is readily amenable for a high-throughput screening using standard screening instrumentation. Genes were selected that measured different cellular processes—RPE development and differentiation (SOX2 and PAX6), RPE function (TYROSINASE, RPE65, RDH5, TRPM1, CSPG5, and BEST1), and RPE pathology (TYROSINASE, RPE65, RDH5, BEST1). FIG. 27A summarizes the outline of the multiplex assay, FIG. 27B shows schematics of the assay principle, and FIG. 27C provides a list of genes used in this multiplex assay, their accession numbers, respective length of their mRNA, and the regions to which Capture Extenders and Label Extenders were hybridized. In brief, mRNA isolated in cell lysate prepared in micro-titer plates is bound to LUMINEX® beads using the anti-sense oligonucleotide technology. Detection probe (biotin-streptavidin-phycoerythrin) is hybridized to specific mRNA also using the anti-sense oligonucleotide technology. mRNA quantification is performed using a flow cytometry based equipment that recognizes the specific fluorescent label on each bead and measures signal intensity per bead.

As a proof-of-principle, the feasibility was demonstrated of a multiplex gene expression assay to simultaneously detect differential levels of multiple genes in a well of a 96-well or 384-well plate between undifferentiated iPSCs, iPSC-derived RPE, and primary human fetal RPE. A total of nine genes were selected for the optimization. HPRT1 and B2M, two housekeeping genes were used for data normalization, because previous work suggested that the expression of these two genes does not differ significantly among the three cell types used in this assay (22). To analyze RPE differentiation, functioning, and pathology the expression of SOX2, PAX6, RPE65, RDH5, CSPG5, TRPM1, and BEST1 was monitored. For in vitro culture, cells seeded at higher density mature faster compared to cells seeded at lower density. Therefore, both iPSC-derived RPE and primary fetal RPE were seeded at two cell densities, 25,000 cells/well or 50,000 cells/well (FIGS. 28B-D). Undifferentiated iPSCs were used as an additional control (FIG. 28A). iPSC-derived RPE and primary RPE were cultured for two weeks to generate confluent pigmented monolayers. To perform the assay at the same time for all cells types, iPSCs were cultured later and reached confluence in only five days. A linear range of detection was calculated for each probe set using purified RNA, and lysates from undifferentiated iPSCs, iPSC-derived RPE (low and high cell density), and primary RPE (low and high cell density) (FIG. 36). All the probes detected signal above the background over a sixteen fold sequential dilution. The linear regression plot generated from this serial dilution generated a coefficient of determination value of more than 0.97 in all cases, indicating that the probes were able to detect a signal over a large range of mRNA concentrations.

Figure 28E:
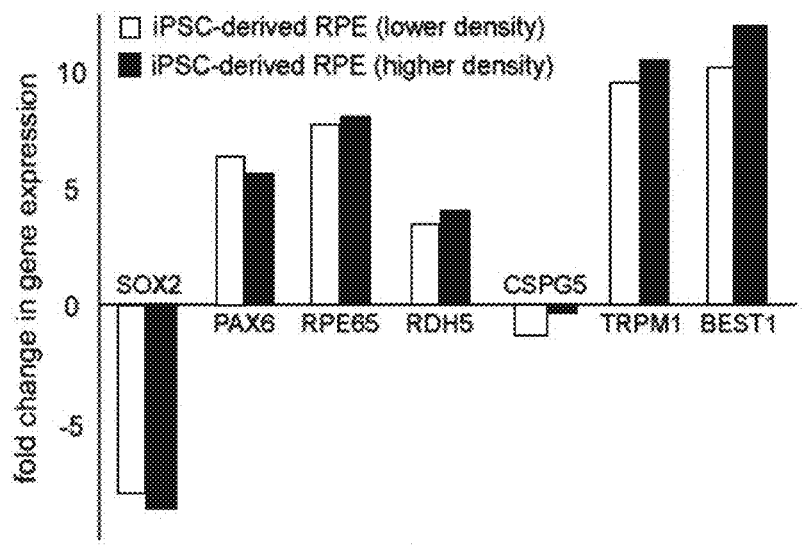
Figure 28F:
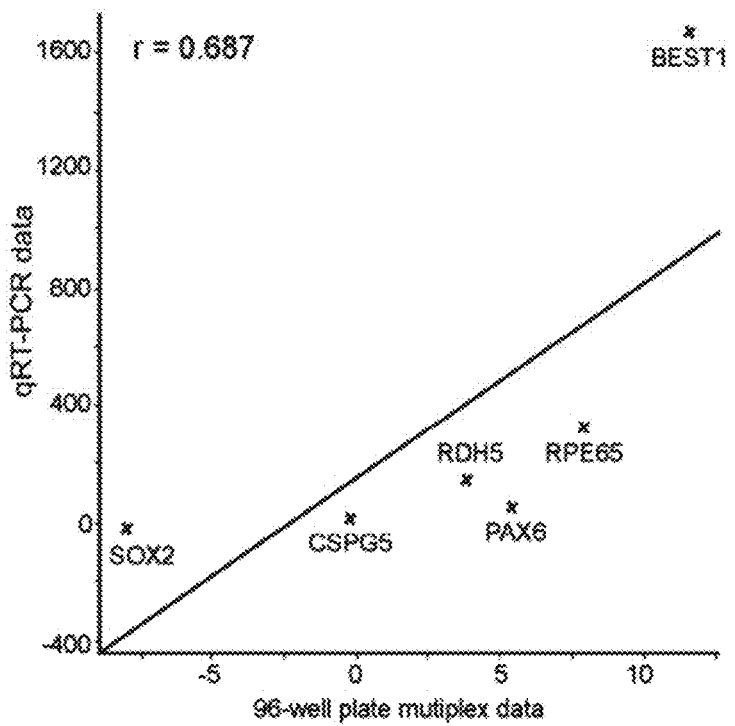
Figure 28G:
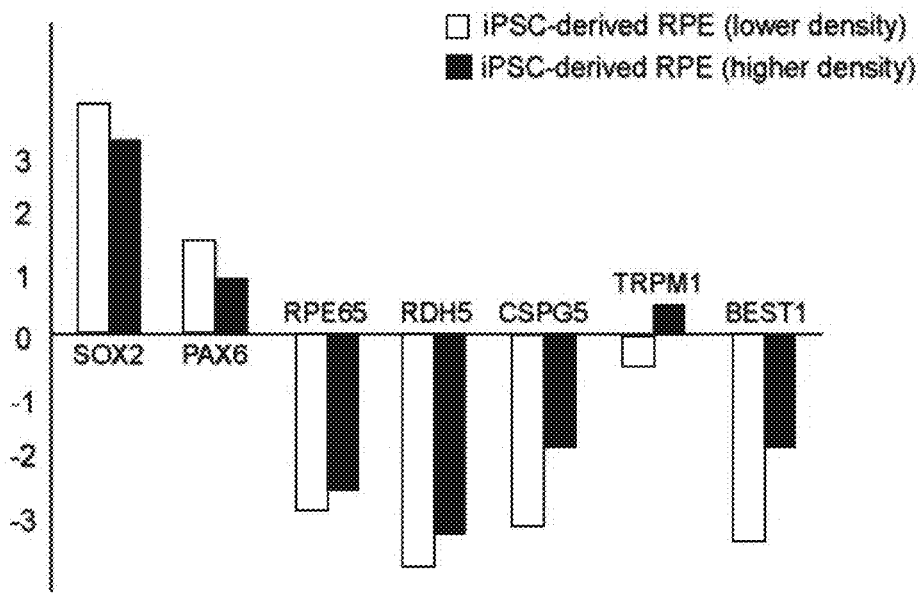
Figure 28H:
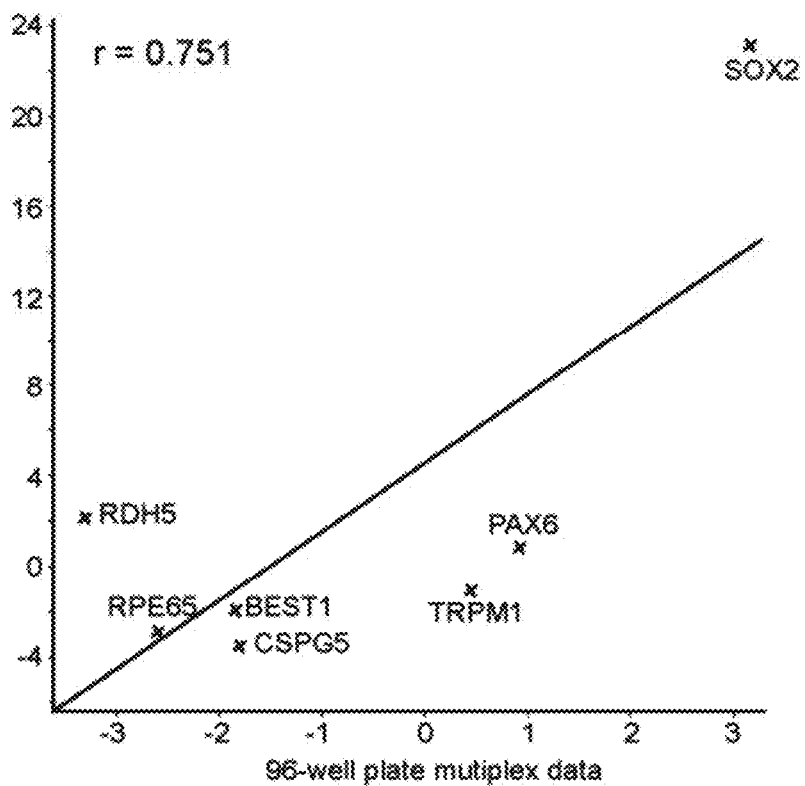

The results of this assay are presented as fold change in gene expression in iPSC-derived RPE at two different cell densities as compared to undifferentiated iPSCs (FIGS. 28E and 28F) and as compared to primary fetal RPE at high cell density (FIGS. 28G and 28H). As expected, compared to undifferentiated iPSC, iPSC-derived RPE expresses lower levels of neural progenitor factor SOX2 and much higher levels of RPE-specific genes PAX6, RPE65, RDH5, TRPM1, and BEST1. CSPG5 an extracellular protein is expressed at similar levels in the two cell types. An important goal of this optimization was to compare results obtained from the multiplex assay to those obtained from a standard qRT-PCR assay (Table A). Therefore, the Pearson's correlation coefficient (r) was determined between fold change in gene expression obtained from the multiplex assay and from the qRT-PCR assay. The results show that the two assays are significantly correlated (r-value=0.69 and 0.75). This provides confidence that the multiplex assay measures relevant gene expression changes and can be used for a high-throughput screen. In conclusion, this high-content gene expression assay can be performed in one and a half days in a high-throughput fashion on undifferentiated iPSCs, iPSC-derived RPE, and primary human RPE. When compared to primary fetal RPE, iPSC-derived RPE express lower levels of differentiation RPE markers (RPE65, RDH5, CSPG5, BEST1) and higher levels of progenitor transcription factors PAX6 and SOX2, suggesting a relatively immature state of these cells. It is, however, important to note that the results obtained by comparison of primary RPE and iPSC-derived RPE in multiplex assay are strongly correlated with the standard qRT-PCR assay presented in Table A.

Evaluating the Limit of Detection and Increasing the Throughput of the Assay

The limit of detection for each transcript in a given assay well was tested, another important aspect of the multiplex assay. The suggested minimal limit of detection for the multiplex gene expression assay is less than or equal to 200 transcripts when analyzing one target per well of a 96-well plate. The following formula was used to calculate the limit of detection (LOD) of our probe set: LOD=Average background value of four wells+3× standard deviation of the average background value (Affymetrix, manufacturer manual). The assay was significantly more sensitive than the described limit, and the following values of detection were obtained: SOX2=41, PAX6=32, RPE65=24, RDH5=10, CSPG5=19, TRPM1=25, BEST1=11, HPRT1=55, and B2M=30. In view of these transcript numbers, the assay was tested in a 384-well format for increased screening throughput and reduce reagent and screening costs.

To test the linearity of the range of signal detection, the assay was performed using two cell densities, 6,000 and 12,000 cells/well in 384-well plate. As expected, after two weeks of culture in 384-well plates, the lower cell density produced less confluent and less pigmented cell layer both for primary fetal RPE cells and for iPSC-derived RPE (FIG. 35A-35D). Two different bead concentrations—700 beads/well per probe, as recommended for a 96-well plate, and 375 beads/well per probe, were tested. An additional probe, TYROSINASE representing RPE maturity was included in this assay. FIG. 35 shows that the assay was successfully optimized in 384-well plate using both bead concentrations. This data support the following three conclusions: (1) results obtained in 384-well plates are similar to those obtained in 96-well plates. For example, when compared to primary RPE, iPSC-derived RPE express higher levels of SOX2 and PAX6 and lower levels of RPE differentiation/functioning genes; (2) the two bead concentrations give almost identical results in the 384-well plate format; (3) the multiplex assay in 384-well plates correlates better (Pearson's correlation coefficient of 0.91 and 0.89 respectively for high and low beads) with the qRT-PCR data as compared to the 96-well plate assay. In conclusion, the present results demonstrate that changes in expression of up to ten different genes can be measured simultaneously using iPSC-derived RPE 384-well plates.

The approach presented here provides a well-defined method for identifying small molecules that downregulate the expression of progenitor genes and upregulate the expression of differentiation genes, thus allowing systematic maturation of pluripotent stem cell-derived RPE in culture. This iPSC-derived RPE can be more effective in therapeutic intervention of macular degenerative diseases and also serve as effective disease model. This screening method also can be used to identify small molecules that alter the activity of putative disease-causing pathways and lead to the discovery of therapeutic drugs.

Example 9

QUANTIGENEPLEX®2.0 Reagent System—96-Well Assay Protocol

The QUANTIGENE PLEX® 96-well Assay was done using following protocol. Cells were seeded per well in 96 well plate and let adjust to the wells for 10 days at 37° C., 5% $CO_2$, with manual media exchanges every other day. Cells from individual wells were then lysed in 200 µL working lysis mixture (Affymetrix) for 30 minutes at 50° C. 80 µL of cell lysate were transferred to the assay's hybridization plate (96-well clear polypropylene plate Abgene #AB0796), where each well already contained 20 µL of Working Bead Mix. Each 20 µL of Working Bead Mix contained 6.6 µL of Lysis Mixture, 5.2 µL of nuclease free water, 0.2 µL of Proteinase K solution, 2 µL of Blocking Reagent, 5 µL of Probe Set, 1 µL of magnetic Luminex beads (1000 beads per gene/well). The Probe Set and Luminex Beads correspond to QuantiGene Plex Set-Panel #11828. The hybridization plate was sealed with the supplied clear, pressure-activated seals and placed in a heating/shaking incubator (LabNet VorTemp 56 P/N S-0256-Q) and incubated for 18-22 hours at 54° C.±1° C. and shaking at 600 rpm. Each of the Magnetic beads used in the multiplex assay have different ssDNA Capture Probes, that work together with the probe set to capture different mRNA targets onto different beads. The overnight hybridization mixtures were then transferred to a 96 well Magnetic Separation Plate (96-well flat bottom microplate Nunc #269620). An Affymetrix Hand Held Magnetic Bead Washer (Affymetrix P/N QP0702) was used to wash the beads, thus removing all unbound materials. 100 µL of 2.0 Pre-Amplifier Working Reagent (3:1000 dilution using PreAmp solution+Amp diluent provided by manufacturer) was added to each assay well. The Magnetic Separation Plate was sealed with adhesive backed foil and incubated for 1 hour at 50° C.±1° C. and 600 rpm. The unbound 2.0 Pre-Amplifier was removed and beads washed 3× with 100 µL of Wash Buffer (provided by manufacturer) using the handheld magnetic plate. 100 µL of 2.0 Amplifier Working Reagent (3:1000 dilution using Amp solution+Amp diluent provided by manufacturer) was added to each assay well. The Magnetic Separation Plate was sealed and incubated for 1 hour at 50° C.±1° C. and 600 rpm. The unbound 2.0 Amplifier was removed and beads washed 3× with 100 µL Wash Buffer using the handheld magnetic bead washer. 100 µL of Label Probe Working Reagent (3:1000 dilution using LabelProbe solution+LabelProbe diluent provided by manufacturer) was added to each assay well. The Magnetic Separation Plate was sealed and incubated for 1 hour at 50° C.±1° C. and 600 rpm. The unbound Label Probe was removed and beads washed 3× with 100 µL Wash Buffer using the handheld magnetic bead washer. 100 µL of SAPE Working Reagent (3:1000 dilution using SAPE solution+SAPE diluent provided by manufacturer) was added to each assay well. The Magnetic Separation Plate was sealed, wrapped in aluminum foil, and incubated for 30 min at RT and 600 rpm. The unbound SAPE Working Reagent was removed and beads washed 3× with 100 µL SAPE diluent using the handheld magnetic bead washer. Signal from beads was measured with a Luminex Flex Map 3D instrument after first re-suspending the beads in 130 µL of SAPE diluent, using DD gate settings between 50-100 beads per message, a sample volume of 50 µL, and a sample timeout of 45 seconds.

Example 10

Aphidicolin

Aphidicolin is a reversible inhibitor of eukaryotic nuclear DNA replication that blocks the cell cycle at early S phase. Its structure is that of a tetracyclic small molecule. Aphidicolin added to iPS cell derived RPE growing on artificial membranes/scaffolds, improves their RPE phenotype. It causes committed RPE cells to further mature and form fully-differentiated and highly polarized tissue monolayers (see FIGS. 30-31). Aphidicolin is dissolved in fourth medium and RPE cells are cultured in it for 6-8 weeks before analysis is done.

Fully-differentiated and polarized RPE tissues on scaffolds will provide more effective therapies for retinal degenerative diseases and will also provide more "natural" models for in vitro disease modeling and for high throughput screenings. Aphidicolin treatment generates tissues with fully mature tight junctions and more mature physiological responses. When combined with a biodegradable scaffold, this compound stimulates RPE monolayer to secrete its own extracellular matrix and attain a real tissue like features.

Example 11

Alginate Coating Enhances Cell Viability and Reduces Cell Detachment

An alginate-enhanced Cryopreservation Protocol is provided below. The results are shown in FIG. 32A-32D.
1. Use 10 mm biopsy punch (ACCU-PUNCH®, USA) to cut out transwell membrane with confluent monolayer of hfRPE.
2. Dip sample into autoclave-sterilized 0.7% sodium alginate (Sigma Aldrich, United Kingdom) dissolved $ddH_2O$ for 0.5 seconds.
3. Dip sample into autoclave-sterilized 2% $CaCl_2$ (Sigma Aldrich, USA) in $ddH_2O$ for 0.5 seconds, to polymerize alginate.
4 Immediately place sample into 2 mL cryovial (Corning, USA) containing either 1 mL CryoStor CS10 (STEMCELL®, Canada) or 10% DMSO cryopreservation media (500 µL 5% RPE, 400 µL FBS, 100 µL DMSO).
5. Place cryovials on ice for 30 minutes.
6. Transfer cryovials to a Mr. Frosty freezing container (Thermo Scientific, USA), pre-cooled to 4° C., and cool to −80° C. at a rate of 1° C./min.
7. Recover cryopreserved tissue by partially melting samples in a 37° C. water bath.
8. Add 1 mL pre-warmed 5% RPE media to cryovial to complete melting.
9. Transfer sample into 1 mL 5% RPE to rinse away cryopreservation media components.
10. Move sample into 1 mL 5% RPE medium.
11. Allow recovery for 3 days, changing media daily.

12. Test cell viability using ethidium homodimer-1 (2.5 µM).

Prepare the SNAPWELL™ (Costar, US) System (FIG. 33A-33E)

1. Manually separate the well top from the well bottom (FIG. 2A)
2. Place the scaffold (Stellenbosch Nanofiber Company (Pty) Ltd., South Africa) into the center of the SNAPWELL™ bottom so that it lays flat (FIG. 2B).
3. Place an O-ring (polytetrafluoroethylene (PTFE), 12 mm×10.25 mm×1.2 mm, Superior Washer and Gasket Corp, US) on top of the scaffold so that it holds the scaffold in place. The O-ring must be previously sterilized by 20-minute treatment in 70% ethanol (FIG. 2C).
4. Place the SNAPWELL™ top on top of the O-ring and gently press into place (FIG. 2D).

Prepare the Scaffold for Cell Seeding

1. Dispense 200 mL of 1×PBS (Life technologies, US) into the SnapWell™ with the scaffold. Leave for two hours at room temperature.
2. Aspirate out the PBS and add 200 mL of human extracellular matrix (ECM)/1×HBSS with phenol red (PR) solution to each SnapWell™ (1 vial ECM: 20 mL HBSS). Human ECM (BD BioSciences, US 1×HBSS with phenol red (Life technologies, US).
3. Place the plate, lid off, under UV light for 2 hours.
4. After 2 hours, turn off UV. To prevent the solution from drying out during cell preparation add 100 mL 1×HBSS without PR (Life technologies, US) to the 200 mL of human ECM/1×HBSS with PR solution.

Seed Cells

1. Aspirate out the 300 mL of human ECM/1×HBSS solution.
2. Dispense 500 mL of cell suspension (in 5% RPE media at a density of 250,000 cells per mL) into each well.

The use of induced pluripotent stem (iPS) cell technology to differentiate RPE provides an autologous or allogeneic cell-based therapy for patients with ocular degeneration. RPE cells derived from stem cells have been injected as a cell suspension into the eyes of patients with retinal degeneration. RPE tissue was generated from iPSC derived RPE grown as a polarized confluent monolayer on a biodegradable scaffold. By transplanting a single monolayer tissue, one can circumnavigate the problems associated with suspensions.

RPE cells were cultured on biocompatible membranes, such as parylene-C and polyimide (Diniz et al, IOVS 2013). These membranes do not degrade overtime, leaving a permanent foreign entity in the eye, which over time will get clogged with proteinaceous material. Disclosed herein is a technique that allows hydrolytic degradation to remove the scaffold as the RPE layer matures and creates its own external environment. Therefore, our method for creating functional and polarized RPE monolayers on scaffolds is a viable tissue engineering strategy that provides therapy for retinal degenerative diseases.

A protocol was produced that utilizes biodegradable scaffolds for culturing RPE cells into a functional tissue that can be translated into in vivo models to combat rental diseases. The main components of this method are a CORNING® COSTAR® SNAPWELL™ plate, a bioinert 0-ring, and a biodegradable scaffold. SNAPWELL™ plates provide the structure and platform for the biodegradable scaffolds. The microporous membrane that creates an apical and basal side is ideal for providing support to the scaffold as well as isolating the distinct sides of the polarized layer of cells. The ability of the SNAPWELL™ insert to detach the membrane allows the support ring of the insert to be used an anchor for the scaffold. However, after combing the support ring and membrane, there is a small void between the bottom lip of the support ring and the porous membrane itself. Therefore, we have utilized a bioinert 0-ring to fit perfectly and fill the void. Now, the support rig can apply pressure uniformly around the outer edge of the membrane to hold the scaffold against the membrane.

First, the SNAPWELL™ apparatus was disassembled, the support ring was removed from the bottom membrane. Next, the biodegradable scaffold, was precut to match the interior dimensions of the SNAPWELL™ membrane, and was placed flat along the bottom of the membrane. The 0-ring was then placed directly into the membrane portion of the SNAPWELL™ insert on top of both the scaffold and the membrane. Then, the SnapWell™ insert was reassembled, ensuring that the support ring presses on the 0-ring so that there is no gap between the support rig and the porous membrane.

Prior to adding any solution to the culturing device, the scaffolds were wetted and sterilized using techniques such as ethanol treatments and ultraviolet light exposure. This scaffold and membrane structure was then suitable for culturing polarized cells by seeding cells on top of scaffold. After the cells were placed onto the scaffold, the culture conditions were maintained including applying additional factors until the tissue is fully develop and functional. The tissue was then ready for use in transplantation to in vivo models or other in vitro studies.

The culturing assembly can be disassembled, detaching the support ring from the membrane and lifting the 0-ring out of the membrane ring. The tissue could also be directly punched or cut out of the device. Since there is nothing chemically holding the tissue to the porous membrane, the tissue lifts off and away from the membrane after being cut. Resulting RPE tissue can be transplanted as a single entity into the subretinal space of patients with retinal degeneration in order to resurrect the degrading areas by preventing photoreceptor death and promoting photoreceptor regeneration.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method for producing human retinal pigment epithelial (RPE) cells, comprising:
   (a) culturing human induced pluripotent stem cells (hiPSCs) in a human embryonic stem cell culture medium comprising human basic fibroblast growth factor (bFGF) and not containing ingredients obtained from non-human animals to produce small embryoid bodies of 200-500 cells;
   (b) culturing the small embryoid bodies from step (a) in a first medium comprising retinal induction medium (RIM) and rock inhibitor (RI), wherein the RIM comprises Wnt inhibitor CKI-7, a Nodal pathway inhibitor, Noggin, and 1 to 3% v/v knockout serum replacement, wherein the Nodal pathway inhibitor is SB-431542 or SB-505124, to form embryoid bodies that have increased efficiency of RPE differentiation;
   (c) culturing the embryoid bodies that have increased efficiency of RPE differentiation from step (b) on a matrigel coated tissue culture substrate-in a second medium comprising a retinal differentiation medium that does not comprise basic fibroblast growth factor (bFGF) and comprises Dickkopf-related protein 1 (DKK1), CKI-7, a bFGF inhibitor, and Noggin, wherein the bFGF inhibitor is PD0325901, PD98059, PD161570, or PD166285, to form differentiating RPE cells that express PAX6 and MITF;
   (d) culturing the differentiating RPE cells from step (C) in a third medium comprising retinal media comprising Activin A and Wnt3a to produce cells that have increased expression of MITF and PAX6 and increased RPE differentiation efficiency; and
   (e) culturing the cells that have increased expression of MITF and PAX6 and increased RPE differentiation efficiency from step (d) in a fourth medium comprising a RPE cell medium comprising a non-canonical Wnt 5a inducer, DKK1, SU5402, and cyclopamine to produce human RPE cells that express TYR, TYRP1, MYRIP, Cadherin 1 or Cadherin 3 and TRPMI 1 or TRPMI 3, thereby producing human RPE cells.

2. The method of claim 1, wherein the first medium comprises 3.5 to 9 mM of CKI-7.

3. The method of claim 1, wherein the Nodal pathway inhibitor is SB-431542.

4. The method of claim 3, wherein the first medium comprises 3.5 to 9 mM of SB-431542.

5. The method of claim 1, wherein the retinal induction medium does not comprise serum.

6. The method of claim 1, wherein the inhibitor of bFGF is PD032590.

7. The method of claim 6, wherein the second medium comprises 0.5 to 2 mM of PD0325901.

8. The method of claim 1, wherein the second medium comprises 3.5 to 9 mM of CK1-7 and 3.5 to 9 mM of SB-431542.

9. The method of claim 1, wherein the first medium comprises 50 ng/ml of Dickkopf-related protein 1 (DKK1).

10. The method of claim 1, wherein the third medium comprises 100 to 200 ng/ml of Activin A.

11. The method of claim 1, wherein the third medium comprises 75 to 150 ng/ml of Wnt3a.

12. The method of claim 1, wherein the second medium comprises 75 to 150 ng/ml of DKK1.

13. The method of claim 1, wherein the fourth medium comprises 75 to 150 ng/ml of WNT5a, 75 to 150 ng/ml of DKK1, 5 μM Cycolopamine and 10 μM of SU5402.

14. The method of claim 1, wherein step (a) comprises culturing the cells in the presence of 1.5% v/v knock out serum replacement.

15. The method of claim 1, wherein the tissue culture substrate is a transwell plate.

16. The method of claim 1, further comprising expressing OCT4, SOX2, LIN28 and Nanog in a human fetal RPE cell to produce the human induced pluripotent stem cells.

17. The method of claim 1, wherein the human induced pluripotent stem cells comprise a nucleic acid encoding a marker operably linked to a RPE cell specific promoter.

18. The method of claim 17, wherein the retinal specific promoter is a tyrosinase promoter.

19. The method of claim 1, wherein the embryoid bodies are cultured in the first medium for 48 hours.

20. The method of claim 1 wherein the embryoid bodies are cultured in the second medium for 18 to 24 days.

21. The method of claim 20, wherein the embryoid bodies are cultured in the second medium for three weeks.

22. The method of claim 1, wherein the differentiating RPE cells are cultured in the third medium for 18 to 24 days.

23. The method of claim 22, wherein the differentiating RPE cells are cultured in the third medium for three weeks.

24. The method of claim 1, wherein the cells are cultured in the fourth medium for 12 to 16 days.

25. The method of claim 24, wherein the cells are cultured in the fourth medium for two weeks.

26. The method of claim 1, further comprising maintaining the RPE cells in the fourth medium and 5% v/v fetal serum.

27. The method of claim 26, comprising maintaining the RPE cells in the fourth medium and 5% v/v fetal serum for six to eight weeks.

* * * * *

SEQUENCE LISTING

<160> NUMBER OF SEQ ID NOS: 2

<210> SEQ ID NO 1
<211> LENGTH: 4721
<212> TYPE: DNA

<213> ORGANISM: Homo sapiens

<400> SEQUENCE: 1

```
ttcttttgcc ctttccttt cataaactga acttcatttt aagcaacaag tctgtgtgaa      60
acagaaatgt cctaatctct ctttgaccaa atgtacccat attcccttat gttaacatgt     120
attttttaca tttaagattg ttaaagtgga acagttttt ttctgccatt atagcacctg     180
tctctacttt tcaaagtata tgaattatga tctttctcat gtggttgtaa gccccatctt     240
tacaagattc acttgatctt tcatattcaa ttatttatgg aacaaaatac ctgtcaattc     300
ttagagtctt ttctacataa tttatttgtg aaagaaaatg ttactggaaa gtgacaaatt     360
agagtcaaaa tataaagact gtggcaggtt atatacctat agtgtgatat gaaagctttt     420
gtaagaagag gtagtggtac taaactggac aaaatccaga taaaagaggc tttgtgaaaa     480
tcaggtaaaa atttacttaa tatacagcaa atactaatag ttgctgttta taaaatacca     540
ttttctgaac attgtttttg cacatataac taaaatgttg aatatacccca agtatgaaaa     600
tttagtgtca tagatattaa gaacattcta ccctttcag gagagtcatt gacagtgatt     660
taagtgactc tgcttacact gcttgtcctc taacactgac tccataatga ttgcagcaaa     720
aaattaaagc tcaaacggtc ttggggatta cctagttcaa tgactttgat ttaacacagt     780
aagtacttga agtagaaaga ggtacattaa caagccaggc aatgatgata tggagggcag     840
tgtgattaga gtacaggatt ctacactcat tctgcattat tggttcatat ttcttctggg     900
gtaactcact tccttccttt ttcatatttt cattgctcta actctagcct tgactttagg     960
aacatctctt cttttccac ctataagata gaattgtttt ctgctgcagg agattaagat    1020
agctggcatt cctttatgct tatttagtca tttcaagcga ttaacttcat cctatcagac    1080
tttgagatta agctgccagt agtgacctca ttaaagtcca cacttctaat aagcttctct    1140
aaaaattgtt gagaaggcat tcttgagttg gtacagggaa agaattgtgg actcagaagc    1200
aaacatagca aagctcattt gttccagtct atggtttaca ggtcaagtga tttgggacca    1260
attgccaaaa tacattggtg aggaaaggca ttaatatcaa ctatgccaag ttactatgct    1320
tattaaactc aaccatgata cagagttata taatgttata atgtattcat tgaatgtttt    1380
ataagaaacc aattgtttat ttgttattta actctgcaaa actacagaaa ggggaaatgg    1440
ttatttaagt gggtaataag ttttaagtat ttatcgttca taataattaa cagagatgtt    1500
acaaaaatgt gactgatttt acttgaaatg ttgccatttt agtaaatgtg gtgccaaagc    1560
aagcatgaaa tgttgccatt ttaaagacat ttattttcta atgctataat atattcatta    1620
catattatta aaataattaa tgtaaaaata cccaaaatgt gaaaataaca cgtaagtcct    1680
attttatgat tttccatatc aaattcagaa actaatactc agatcttatt gtttaaatag    1740
tatttaaaat taaagacaca tagtcaggaa tatatgctaa ataaattttc caaattgaat    1800
aactaacttt cagggttgcc ttactttcaa caagaatatg cctctatttg attactaatt    1860
gtaactttgt tcatagacta cataaggtaa tattacaaac atattcatta ttttgacaca    1920
tacttactta aataataaat aaacattaga aaatatactt actatttata tataaagaat    1980
ttttttgttt cgaaggaact ttaataaatg agattataag gttgttgttc aggtacattg    2040
aacatttttt caggttaata aggtgtctaa aaataagttt agaaagatct aaggtattct    2100
ttttatttg ttttttgtcct tttttatttt tcttttttga actgggtttc ttcttcaatt    2160
agccctggct ggatgtcctg gaactagctc tatatgccat gctgtcttca aactcataga    2220
gatctgccta cctttgcatc ccaagtgctg ggattaaagg tatgaaccac ctcttccacc    2280
```

```
actgccaagt aagaattctt attttacata agtcattatg aaggaagtta tgtgtttact    2340
gtaaacaaga ttaatgactt ggtttgctga ttttctctga aaacatgaaa tctcttcata    2400
tagatcttgc ttctggataa taaaaggccc atggagaaat gttcgtctgt ctagtttcat    2460
attcatatta atgatcctga atcaatttt c ctccattgag acttgcatac ttaagtatta   2520
atgattgctg gagttccatt cataaggatt ctttatgtat tacatgttaa aattttta aa    2580 cctacgacat tttgggatat agtttagtaa aacatcttaa atggtgtaag tggtaccaat    2640
tagtttgaag gcaaaaacaa ttgtttaagt ggattaaggt ctgttcaata ctagggaaca    2700
cctgcttgaa acacttgaca atagaaactt agctaactta cccatgtctg gaaaggtcat    2760
ggactctgaa ggaaaactac ttttaccatt ttcctaaatc aatatagctt ttaactattc    2820
taaacactga tcattatacc catagacagt ttagatcaac cctttccaaa gaagattctg    2880
tttgtagtag ataaggctta atacaaagat cctcaattgg tccaaatcca gagaataggt    2940
aagcctgtgg tgtttaggtg cccaacttag tctaccaata atactaccta tgtacttgag    3000
tactagtgaa caggatacag aaggtggtat caggaagact gtaagaacca gaaaatatga    3060
atacatacat gtgtatattt atgcaagagt aacaattaaa gaagtttatt aatctgagtg    3120
tgtatgtgtt aatgtataaa aatctcagaa aagtatttaa aattattttg cctttggaaa    3180
taaaaataac aagtattgtt caagaaaaag ataattccag gatactagcc aattttgctc    3240
ttaacttaga aatataatta tatttttct tctctttgac tggataaata tgtacgaatg     3300
ttctttgaat atttgcagcc aatttgactc cctaaaaaat ggtatagttt taaatgtgtt    3360
taacatattg cttttgtgaa agacattttt ttagtattag attcaatact ttttaaccat    3420
gtggacatgg ttggtgttat ttttgttcta gaaaggaact gttaaatttc tgctccaact    3480
taggtcatat aagggaaaat gaatctggta ttctacagaa aaatataact gtaaccattt    3540
tgatgatttt tgtgttaatt agcactgttt gtctgttcat atcattgagg cacagaaatg    3600
gtatatttat ataacaccta ccaaacagcc tcataaagaa atagatagat tctggggaat    3660
aaatgatctc catttgatcc tcagttttat taaaatcctt ctgttcctgt ggcatgaatt    3720
catccaaact gagtaatgct ggcaagcagg aagg ggatca aggtcatcca agggatactg    3780
acttggaagg gtctgggcat gcaaccaagt acttccaggg tgaattatta ttaagaaaaa    3840
gaatgttgac aaaaaaatat gtgaaaagga cctatagcta gctattctct tggtgacctg    3900
ggtcttgagg aagttctctg ggaagagtca ctcagcacat ttggtcaaat gaattcacct    3960
attctgaaaa ccaaatgaat atagatttct ggacacctcc caaggattca tgtgtaagat    4020
gaaatgcaga ttgttcacca aaattgtccc tgactcctat acttagacca tttatttttc    4080
tgaaatccca taaactgaga agatgctgtc tgattagaag atacacaagt cgtggataat    4140
aagacaaaag agcccatgaa cctacaaagc tcattgcaaa gtgaacttct gtcttgtaac    4200
agagaaagca gacaaaccaa caaaatcatt tatttcagtg aaaaggaggg gccagaaatg    4260
gaaagattac atttcctaag tctcgtactt gaagacaggt tgggtcctca gaactaatta    4320
agtagtagaa tgcacaatgt gcttcaagaa aaaagaagct atgaaaaaca ggtagtctat    4380
tttatttcaa cctagcaaca gtgagaaaag gatgagctag caaggagatg cagatagtga    4440
agtgtccatt gtggatttac tctggttctg acaggtggaa ttgcttccat tcaaaacaaa    4500
caaaataaac ttctaactca cagtaattca cagtgtcaca ctttgtaaca caggatgtca    4560
aagtttcagg acatacagtc tcaacacata ggtaattaat ttaagtgagg tgatttgagt    4620
```

```
gaatttaaat gcaatggact tgtagatttt gtaaaaagaa gacacgtctt tcaatacgca    4680
cacatatggg aaaatggtat gtaaatatga agttagcact t                       4721

<210> SEQ ID NO 2
<211> LENGTH: 971
<212> TYPE: DNA
<213> ORGANISM: Homo sapiens

<400> SEQUENCE: 2
caggaacatc caaactgagc agccggggtc ccccccaccc cccacccccgc ccctcccggc      60 aactttgagc ctgtgctggg acagagcctc tagttcctaa attagtccat gaggtcagag     120
gcagcactgc cattgtaacg cgattggaga ggatcacgtc accggacacg cccccaggca     180
tctccctggg tctcctaaac ttggcgggga gaagttttag cccttaagtt ttagccttta     240 accccccatat tcagaactgt gcgagttggc gaaaccccac aaatcacaac aaactgtaca    300
caacaccgag ctagaggtga tctttcttgt ccattccaca caggccttag taatgcgtcg     360
ccatagcaac agtgtcacta gtagcaccag cacttcccca caccctcccc ctcaggaatc     420
cgtactctcc agtgaacccc agaaacctct ggagagttct ggacaagggc ggaacccaca     480
actccgatta ctcaagggag gcggggaagc tccaccagac gcgaaactgc tggaagattc     540
ctggccccaa ggcctcctcc ggctcgctga ttggcccagc ggagagtggg cggggccggt     600
gaagactcct taaaggcgca gggcggcgag caggtcacca gacgctgaca gctactcaga    660
accaaatctg gttccatcca gagacaagcg aaagacaaga gaagcagagc gagcggcgcg     720
ttcccgatcc tcggccagga ccagccttcc ccagagcatc cctgccgcgg agcgcaacct     780
tcccaggagc atccctgccg cggagcgcaa cttttcccgg agcatccacg gccgcggagc     840
gcagcctttc cagaagcaga agcgcggcgc caatggctcg cgaatgaatc ccgtcggttt     900
taacaaacgg tcggtgaacc tggggaaaaa cctgcggtta acccaactta aattcgccct     960
ctgggcaaga c                                                          971
```